US010709784B2

(12) United States Patent
Holbein et al.

(10) Patent No.: US 10,709,784 B2
(45) Date of Patent: Jul. 14, 2020

(54) METAL CHELATING COMPOSITIONS AND METHODS FOR CONTROLLING THE GROWTH OR ACTIVITIES OF A LIVING CELL OR ORGANISM

(75) Inventors: Bruce Edward Holbein, Guelph (CA); Minhua Feng, New City, NY (US); Ann Louise Huber, Belwood (CA); Denis Keith Kidby, Belwood (CA); Ann Louise Huber, legal representative, Belwood (CA)

(73) Assignee: CHELATION PARTNERS INCORPORATED, Ontario (CA)

( * ) Notice: Subject to any disclaimer, the term of this patent is extended or adjusted under 35 U.S.C. 154(b) by 593 days.

(21) Appl. No.: 14/124,619

(22) PCT Filed: Jun. 8, 2012

(86) PCT No.: PCT/CA2012/000562
§ 371 (c)(1),
(2), (4) Date: Aug. 24, 2015

(87) PCT Pub. No.: WO2012/167368
PCT Pub. Date: Dec. 13, 2012

(65) Prior Publication Data
US 2016/0038604 A1 Feb. 11, 2016

Related U.S. Application Data

(60) Provisional application No. 61/494,664, filed on Jun. 8, 2011.

(51) Int. Cl.
| | |
|---|---|
| A61K 47/02 | (2006.01) |
| A01N 43/40 | (2006.01) |
| A61K 31/721 | (2006.01) |
| A61K 31/718 | (2006.01) |
| A61K 31/745 | (2006.01) |
| A61K 31/79 | (2006.01) |
| A61K 31/785 | (2006.01) |
| C02F 1/68 | (2006.01) |
| A61K 47/61 | (2017.01) |
| A61K 47/58 | (2017.01) |
| A01N 25/10 | (2006.01) |
| A61K 31/351 | (2006.01) |
| A61K 31/4196 | (2006.01) |
| A61K 31/43 | (2006.01) |
| A61K 31/4412 | (2006.01) |
| A61K 31/496 | (2006.01) |
| A61K 31/513 | (2006.01) |
| A61K 31/565 | (2006.01) |
| A61K 31/65 | (2006.01) |
| A61K 31/7036 | (2006.01) |
| A61K 31/7048 | (2006.01) |
| C02F 101/20 | (2006.01) |

(52) U.S. Cl.
CPC .............. *A61K 47/02* (2013.01); *A01N 25/10* (2013.01); *A01N 43/40* (2013.01); *A61K 31/351* (2013.01); *A61K 31/4196* (2013.01); *A61K 31/43* (2013.01); *A61K 31/4412* (2013.01); *A61K 31/496* (2013.01); *A61K 31/513* (2013.01); *A61K 31/565* (2013.01); *A61K 31/65* (2013.01); *A61K 31/7036* (2013.01); *A61K 31/7048* (2013.01); *A61K 31/718* (2013.01); *A61K 31/721* (2013.01); *A61K 31/745* (2013.01); *A61K 31/785* (2013.01); *A61K 31/79* (2013.01); *A61K 47/58* (2017.08); *A61K 47/61* (2017.08); *C02F 1/683* (2013.01); *C02F 2101/20* (2013.01)

(58) Field of Classification Search
CPC ...................................................... A61K 47/02
See application file for complete search history.

(56) References Cited

U.S. PATENT DOCUMENTS

| | | | | |
|---|---|---|---|---|
| 2,900,305 | A * | 8/1959 | Siggia .................... | A61K 33/18 424/672 |
| 5,217,998 | A | 6/1993 | Hedlund et al. | |
| 2006/0030619 | A1 | 2/2006 | Liu et al. | |
| 2009/0215701 | A1 * | 8/2009 | Theil .................... | A61K 31/155 514/1.1 |

OTHER PUBLICATIONS

Kollidon (Polyvinylpyrrolidone for the pharmaceutical industry, BASF product information, Mar. 1998).*
Mahoney (Journal of Clinical Investigation. Oct. 1989;84(4):1362).*
Mehvar (Journal of Controlled Release 69 (2000) 1-25).*
Corbin (Science Feb. 15, 2008: vol. 319, Issue 5865, pp. 962-965).*
Singh (Nature 417, 552-555 (May 30, 2002)).*
Min-Hua Feng et al., "Iron(III)-Chelating Resins 3. Synthesis, Iron(III)-Chelating Properties, and in Vitro Antibacterial Activity of Compounds Containing 3-Hydroxy-2-methyl-4(1H)-pyridinone Ligands", J. Med. Chem, Jan. 1, 1993, pp. 2822-2827.

(Continued)

*Primary Examiner* — Devang K Thakor
(74) *Attorney, Agent, or Firm* — Foley & Lardner LLP

(57) ABSTRACT

The present invention provides for metal chelating compositions which are soluble in aqueous media. The present invention also provides chelating compositions that possess acceptable iron sequestering strengths and are able to present a physical form that potentially inhibits (e.g. does not permit easy) access of iron sequestered by the compositions to the cells being targeted. Compositions comprising chelating aspects affixed to or incorporated into suitable carrier materials such that the resulting metal chelating composition is soluble in aqueous media are also provided. Disclosed herein are chelating compositions, for chelating one or more essential metals. The chelating compositions being soluble in an aqueous medium and comprising one or more metal binding chemical groups affixed to or incorporated into the structure of a carrier material, such that the resulting chelating composition is able to bind one or more metals, and remains substantially soluble in the aqueous medium with its bound metal or metals.

17 Claims, 29 Drawing Sheets

(56) References Cited

OTHER PUBLICATIONS

Minhua Feng et al., "Iron(III)-Chelating Resins. IX. Antibacterial Activity of a Water-Insoluble Iron(III)-Chelating Resin", J. Med. Chem, Jan. 1, 1994, pp. 924-927.
David Bebbington et al., "Prodrug and Covalent Linker Strategies for the x Solubilization of Dual-Action Antioxidants/Iron Chelators", Bioorganic & Medicinal Chemistry Letters, vol. 12, No. 22. Nov. 1, 2002, pp. 3297-3300.
European Search Report corresponding to Application No. 12797205.7, dated Jul. 6, 2015.
European Search Report corresponding to Application No. 12797205.7, dated Feb. 19, 2015.
Afinogenov, G.E. et al. "Effect of polymer complexons on basis of vinylpyrrolidone copolymers with vinyliminodiacetic acid and metacryloilacetone upon antibiotic susceptibility of antibiotic resistant bacterial strains", Antibiotiki (1978), 23: 419-424.
Feng, M. et al. "Iron removal from milk and other nutrient media with a chelating resin", Journal of Dairy Science (1995), 78:55-61.
Friedman, M. et al. "Review of antimicrobial and anti oxidative activities of chitosans in food" Journal of Food Protection (2010), 73:1737-1761.
Geckeler, K. et al. "Preparation and application of water-soluble polymer-metal complexes", Pure & Applied Chemistry (1980), 52:1883-1905.
Harmatz, P. et al "Phase Ib clinical trial of starch-conjugated deferoxamine (40SD02): a novel long-acting iron chelator", British Journal of Haematology (2007), 138:374-381.
Holbein, B.E. et al. "Effect of trace iron levels and iron withdrawal by chelation on the growth of Candida albicans and Candida vini", FEMS Microbiology Letters (2010), 307:19-24.
International Search Report and Written Opinion dated Oct. 17, 2012 for PCT/CA2012/000562.

Kemp, J.D. et al. "Inhibition of lymphoma growth in vivo by combined treatment with hydroxyethyl starch deferoxamine conjugate and IgG monoclonal antibodies against the transferrin receptor", Cancer Research (1995), 55:3817-3824.
Pizarro, G. et al. "Nonionic water-soluble polymer: preparation, characterization, and application of poly(1-vinyl-2-pyrrolidone-co-hydroxyethylmethacrylate) as a polychelatogen", Journal of Applied Polymer Science (2006), 100:178-185.
Rafikov, R.Z. et al. "Pharmacokinetics of polymer metal complex II", Pharmaceutical Chemistry Journal (1987), 21:185-188.
Rivas, B.L. et al. "Water-soluble copolymers of 1-vinyl-2-pyrrolidone and acrylamide derivatives: synthesis, characterization, and metal binding capability studies by liquid-phase polymer-based retention technique", Journal of Applied Polymer Science (1999), 72:741-750.
Roller, S. et al. "The antifungal properties of chitosan in laboratory media and apple juice" International Journal of Food Microbiology (1999), 47:67-77.
Tsafack, A. et al. "Mode of action of Iron (III) chelators as antimalarials IV. Potentiation of desferal action by benzoyl and isonicotinoyl hydrazone derivatives" Journal of Laboratory and Clinical Medicine (1996), 127:574-582.
Zhou T. et al., "Synthesis and Iron(III)-chelating properties of novel 3-hydroxypyridin-4-one hexadentate ligand-containing copolymers", Biomacromolecules (2008), 9:1372-1380.
Zhou, T. et al. "Design of clinically useful macromolecular iron chelators", Journal of Pharmacy and Pharmacology (2011), 63:893-903.
Simonart, T. et al. "Iron withdrawal strategies fail to prevent the growth of SiHa-induced tumors in mice." Gynecologic Oncology, vol. 90, 2003, pp. 91-95.
Winston, A. et al. "Evaluation of polymeric hydroxamic acid iron chelators for treatment of iron overload." J Pharmacol Exp Ther., vol. 232, No. 3, Mar. 1985, pp. 644-649.

* cited by examiner

A Synthesis of 3-(benzyloxy)-2-methyl-4*H*-pyran-4-one:

B Synthesis of 1-(2-aminoethyl)-3-benzyloxy-2-methyl-4(1*H*)-pyridinone) AHMP:

C Synthesis of 3-Hydroxy-1-(β-methacrylamidoethyl)-2-methyl-4(1H)-pyridinone (MAHMP):

Summary of optimization testing scheme to synthesize soluble chelating compositions comprising an active pyridinone chelating agent co-polymerized in a soluble linear polyvinylpyrolidone polymeric carrier:

METAL CHELATING COMPOSITIONS AND METHODS FOR CONTROLLING THE GROWTH OR ACTIVITIES OF A LIVING CELL OR ORGANISM

CROSS-REFERENCE TO RELATED APPLICATIONS

This application is the National Phase of International Patent Application No. PCT/CA2012/000562, filed Jun. 8, 2012, which claims priority to U.S. Provisional Application No. 61/494,664, filed Jun. 8, 2011. The contents of these applications are herein incorporated by reference in their entirety.

FIELD OF THE INVENTION

The present invention relates to metal chelating compositions which are soluble in aqueous media and uses thereof. More specifically, the present invention relates, at least in part, to compositions comprising chelating aspects affixed to or incorporated into suitable carrier materials such that the resulting metal chelating composition is soluble in aqueous media. The present invention also relates to chelating compositions that possess acceptable iron sequestering strengths and are able to present a physical form that prevents, inhibits or reduces access of iron sequestered by the compositions to cells being targeted.

BACKGROUND

Iron is required and cannot be replaced by other metals, for many essential aspects of a living cell's physiology and metabolism, whether the cell is a spoilage causing microbe in a product intended for use by humans or a pathogenic cell within the body and capable of causing human or animal or fish disease, i.e., such as a microbial pathogen (bacterial, fungal or parasitic) or a pathogenic animal cancer cell. The only known exception to this essential requirement for iron is with certain non-pathogenic Lactobacilli bacteria.

This generally universal iron requirement could therefore be a useful target for new means to interfere with or a stop the growth of cells. To date, only limited advances have been made in affecting iron nutrition of cells due to a lack of suitable chemical compounds that possess the needed characteristics. Bacterial, fungal, parasitic and animal cells normally possess one or more of various Fe uptake mechanisms that operate at the cell membrane/external environment boundary and these cellular mechanisms essentially serve to internalize Fe from the external environment for use within the cell as shown in FIG. 1.

Iron reduction from an enzymatic surface receptor/reduction/transport system (I) is important for making iron that predominates in aerobic environments as insoluble $Fe^{3+}$ into the more soluble $Fe^{2+}$ form, and this mechanism is found in most bacterial, fungal and animal cells. Pathogenic bacteria and yeasts generally possess multiple Fe uptake mechanisms while animal cells do not produce or utilize microbial type siderophores. Siderophores are chelating compounds produced primarily by microbial cells. Rather than using a siderophore, vertebrate animal cells utilize the protein transferrin (II) that is typically produced by liver cells of the animal and which circulates to shuttle iron from the gut through the blood stream and to all other cells of the body. Certain pathogenic microorganisms have developed an ability to bind and utilize transferrin Fe by transferring this to a shuttle carrier in the membrane without taking up the transferrin molecule into the cell (II). Other bacteria and fungi can take up heme, another iron carrying compound produced by microbial and animal cells. Heme can be taken into the cell directly by a receptor/transport system (II) and the cells then use the heme iron internally. Various bacteria and fungi can utilize various heterologous siderophores as produced by other microbes by removing iron from these at the cell surface shuttle system (III). The iron reduction mechanism (I) may potentially play a role in iron removal from heterologous siderophores or transferrin in some cells. Various bacterial and fungal pathogens produce their own autologous siderophores in response to iron need, secrete these into the extracellular environment and then take these back up with iron as chelated from the external environment (IV). Cells of parasitic animals have been studied less but some are known to acquire heme and it is likely that they employ acquisition mechanisms similar to other eukaryotic cells such as the fungi or animal cells. Without wishing to be bound by theory, Table 1 below provides a further comparison of the various iron acquisition mechanisms as diagrammed in FIG. 1 and discussed above.

TABLE 1

Summary of Iron Acquisition Mechanisms of Cells

| Type (see diagram) | Mechanism | Bacteria | Fungi | Animal |
|---|---|---|---|---|
| I | Enzymatic Fe reduction and transport | Assists uptake from various siderophores | For direct Fe uptake and also in conjunction with siderophore uptake | Direct uptake analogous to yeast system |
| II | Receptor/Uptake for Heme or binding of Transferrins for stripping of iron for uptake | Pathogens such as *Staphylococcus aureus* can access heme and transferrins | Heme uptake by pathogenic yeasts such as *Candida albicans* | Normal uptake involves receptors for transferrin |

TABLE 1-continued

Summary of Iron Acquisition Mechanisms of Cells

| Type (see diagram) | Mechanism | Bacteria | Fungi | Animal |
|---|---|---|---|---|
| III | Receptor/Uptake for heterologous siderophores | Can be associated with reduction system; a common shuttle system found in various bacteria | Found in various types including pathogenic yeasts such as *Candida albicans* | Not present but low molecular weight chelators enter cell |
| IV | Production/Release/ Uptake of Autologous Siderophores | Common with an array of hydroxamate and catecholate types produced by different bacteria | Pathogenic *Candida* produce while other non pathogen yeasts do not | Animal cells use animal transferrins analogous to siderophores |

There are variations of the simplified generalized Fe uptake mechanisms as summarized in Table 1 and diagrammed in FIG. 1, as could be found for specific cell species. However, for the purposes of this disclosure, the four generalized mechanisms (I-IV) adequately summarize general Fe nutrition for bacteria, fungi, and animal cells including the cells of man and other animals including parasitic cells. It will be appreciated that there are two unifying features that Fe as needed internally by a cell is either off-loaded from a molecule carrying the Fe after the molecule is intercepted at the cell surface by a receptor/ transport system or, the Fe is taken up directly into the cell along with the molecule carrying the iron.

Conventional metal chelating compounds such as the iron chelators deferoxamine (also called desferrioxamine B or Desferal™ as marketed by Novartis Ltd.) or deferiprone (1,2-dimethyl-3-hydroxy-pyrid-4-one, as marketed by Apotex Pharmaceutical Company) are already used for medical purposes related to treating human iron metabolic disorders. For these disorders, these compounds chelate iron in the body and provide for its excretion as a soluble low molecular weight iron-chelator complex. Their use has also been proposed for the treatment of infection and cancer. Thus, U.S. Pat. No. 5,663,201 disclosed the use of desferrioxamine B salts for the treatment of cancer while U.S. Pat. Nos. 5,256,676 and 6,825,204 disclose the use of 3-hydroxy-pyrid-4-ones, such as deferiprone for the treatment of parasitic infections. Additionally, deferiprone or hydroxamates such as desferal have been proposed in U.S. Pat. No. 5,302,598 as adjuncts to antibiotics for the treatment of *Pneumocystis carni* parasitic infection. Other microbial chelators such as exochelin have been proposed in U.S. Pat. No. 5,837,677 for the treatment of cancer. Various chelators have also been disclosed as adjuncts to antibiotics, preservatives or anti-microbial agents such as those disclosed in U.S. Pat. Nos. 6,793,914; 6,267,979; 5,573,800; 6,165,484 and 6,893,630.

Other N-substituted (U.S. Pat. No. 6,932,960) or cycloalkyl (U.S. Pat. No. 7,410,985) derivatives of 3-hydroxy-4-pyridinones have been described for use as alternate pharmaceuticals to relieve medical conditions of iron overload or to treat parasitic infection or other diseases.

However, all these previously disclosed low molecular weight chelators as mentioned above, (i.e., chelators having a low molecular weight of for example 1500 Daltons or less) suffer from a common problem. The problem is that most cells including pathogenic cells can readily access and use these low molecular weight chelators as sources for their needed iron. Molecules of a size of around 1500 Daltons or less can permeate the cellular membrane of prokaryotic (e.g., bacteria) and eukaryotic (e.g., fungal and animal) cells. Thus, the iron chelates of these conventional low molecular weight compounds and compositions of low molecular weight are potentially exploitable for iron by certain bacterial and other cells that would be desirable to control, i.e., through the use by such cells of one of the iron acquisition mechanisms shown in FIG. 1. This fundamental problem severely limits the potential use of the previously disclosed chelators and compositions for controlling cell growth.

Moreover, inappropriate use of one of these previously disclosed chelators in attempt to control a cell that can utilize the particular chelator employed may be a problem and potentially worsen the situation of preservation, infection control or cancer control. In this regard, deferiprone and similar chelators, such as those disclosed in U.S. Pat. No. 6,767,741, are known to provide iron for animal cells in laboratory culture. Therefore, these chelators can not be expected to be useful for treating animal cancer cells. Citric acid is an example of a chelator that meets the definition of a suitable chelator as was disclosed in U.S. Pat. Nos. 6,165,484 and 6,267,979 but citrate is often used to make iron soluble and available in culture media that is used to grow a variety of cells (Porterfield, J., S. 1978) Similarly, chelators, such as ethylene-diamine-tetra-acetic acid (EDTA) as disclosed in U.S. Pat. No. 6,767,741 for controlling growth of cells is used to supply metals in growth media for plants and other cells (Hughes and Poole. 1989). Thus, known soluble chelators of a low molecular weight of less than approximately 1500 Daltons such as EDTA and the entire chemical family of its related compounds may be problematic as chelators for use in the control of infection, cancer or microbial spoilage, given that many cells can potentially utilize these for iron delivery.

Gram negative bacteria comprise a principal category of infection causing bacteria and these have been shown to possess a generalized Fe uptake mechanism that can utilize deferiprone, desferal and many other chelators such as those disclosed in the prior art cited above (Stintzi, A., C. Barnes, J. Xu, K. N. Raymond. 2000). Pathogenic yeasts and other fungi can also utilize a variety of chelators as have been disclosed in the prior art cited above (Howard, D. H. 1999).

Chelating compositions comprised of a metal binding aspect affixed to an insoluble supporting carrier material have been disclosed previously. The compositions disclosed in U.S. Pat. No. 4,530,963, for example, relate to affixing known metal chelating molecules such as deferoxamine or catechol to an insoluble support material so as to provide an insoluble chelating composition. Such insoluble compositions enable the physical contact and removal of the composition with/from an aqueous medium to be treated. Such previously disclosed chelators are, however, inappropriate for treatment within an animal, including a human, due to their insoluble form. Insoluble compositions would not be suitable for administration into the body, for example into the blood stream.

Bacterial adhesion and biofilm formation are now recognized to be important cellular activities for bacterial and fungal pathogens during disease development (Hentzer M., M. Givskov, 2003). Typical iron chelators, such as desferrioxamine, have been shown to increase twitching motility and restrict biofilm formation in the laboratory (Singh et al, 2002). Appropriate restriction of iron supply during the early stages of bacterial or fungal disease may interfere with a pathogenic cell's activity of establishing a biofilm for example on an epithelial surface of the respiratory or urogenital tracts or on indwelling medical devices such as a urinary catheter. Iron chelators as disclosed in the prior art may suffer the same limitations for use in interfering with the activity of microbial adhesion for pathogens for those pathogens that can utilize these chelators or otherwise obtain iron from these.

There is therefore a need for iron chelating compounds that may be employed for sequestering iron. There is also a need for iron chelating compounds that are not utilizable, or easily utilizable, by the intended target cells. There is a further need for chelating compositions incorporating, for example, the metal binding properties of low molecular weight chelators in a structure where these chelators are affixed to a carrier that results in these being of sufficiently high molecular size so as not to be taken up into cells or be otherwise accessed for their iron by a cell.

SUMMARY

Metal chelating compositions are provided that are at least generally soluble in aqueous media. In addition, in certain embodiments, chelating compositions are provided that possess acceptable iron sequestering strengths and are able to present a physical form that potentially inhibits access to or does not permit easy access, of iron sequestered by the compositions to the cells being targeted. Compositions comprising chelating aspects affixed to or incorporated into suitable carrier materials such that the resulting metal chelating composition is soluble in aqueous media are also provided in various embodiments. In accordance with a further aspect, there is provided soluble compositions which can chelate iron and/or other essential metals (i.e. one or more essential metals) in the external environment of a living cell or organism, such that the chelated metal is potentially no longer readily accessible to the normal metal (e.g. iron) acquisition mechanisms of the cell or organism.

As a result of the use of the chelating compositions, the cells or organisms, so-treated, may be deprived of sufficient quantities of essential iron or other trace essential metal(s) and, as a result, the cells or organisms may be impaired in their activities or growth. Certain of the chelating compositions potentially provide means to limit cell growth and cell activities including activities related to spoilage of products, disease production in animals including man and/or resisting the action of anti-cellular agents such as antibiotics or preservative chemicals. Various chelating compositions are also useful for binding iron or another trace metal and substantially denying its access to microbial cells including fungi and bacteria and also to parasitic organisms and animal cancer cells.

The present invention in accordance with a further aspect provides methods for utilizing embodiments of the metal chelating compositions for treating an animal including fish or a human to improve the course of disease as caused by pathogenic cells or organisms, including those cells and organisms with resistance to anti-cellular agents. The present invention in accordance with an additional aspect allows for and provides the exploitation (i.e. methods) of embodiments of the metal chelating compositions for preserving products from microbial spoilage. The present invention in accordance with yet an additional aspect provides for certain of the metal chelating compositions containing pyrrolidone or starch within their structure where iodine is affixed to the starch or pyrrolidone aspect such that the iodine containing chelating composition possesses two modes of activity, i.e., as related to the iodine content and also from the metal chelating aspect of the chelating composition.

Certain of such compounds may potentially remove or sequester iron away from the cells to be targeted and not themselves be utilizable, or easily utilizable, for iron by the cells these compounds were meant to target. Compounds that bind iron are typically referred to as iron chelators.

Generally, aspects of the present invention provide a substance capable of taking up (e.g. bind) a metal from an aqueous medium, the substance having
- a chelate (forming) aspect
- a (water, i.e. aqueous medium) soluble aspect (at least when alone (i.e. metal free) and, depending on the intended environment of use, also when associated with bound metal or metals); and
- a molecular weight aspect favoring the above mentioned soluble aspect (i.e. in relation to the aqueous medium of intended use)—for example a molecular weight greater than 1500 Daltons in certain embodiments and for example a molecular weight greater than 5000 Daltons in other certain embodiments.

One embodiment of the invention provides for a chelating composition, for chelating one or more essential metals, the chelating composition being substantially soluble in an aqueous medium and comprising one or more metal binding chemical groups affixed to or incorporated into the structure of a carrier material, such that the resulting chelating composition is able to bind one or more metals, and remains soluble in the aqueous medium with its bound metal or metals. The exploitation of such a composition may, for example, be for the purpose such that the metal or metals so-bound to the chelating composition become less available for uptake and use by cells or parasitic organisms, the cells or parasitic organisms requiring such trace metal or metals for their growth and, as a result of the action of the chelating composition, the ability of the cells or parasitic organisms to continue to grow is potentially somewhat reduced.

In a further aspect of the composition(s) outlined above the essential metals are trace essential metals.

In a further aspect of the composition(s) outlined above the suitable metal binding chemical groups are selected from one or more of the carboxyl, hydroxyl, phenolate, catecholate, hydroxamate or hydroxypyridinone chemical types.

In a further aspect of the composition(s) outlined above the chelating composition contains metal binding chemical groups possessing similarity to those of deferoxamine or deferiprone.

In a further aspect of the composition(s) outlined above the chelating composition has a carrier material comprised of vinylpyrrolidone, dextran, starch, styrene or acrylamide.

In a further aspect of the composition(s) outlined above the chelating composition comprises metal binding groups of 3-hydroxy-pyridin-4-one incorporated into a carrier material comprised of a polymer matrix of vinylpyrrolidone, dextran, starch or acrylamide.

In a further aspect of the composition(s) outlined above the chelating composition has a lower molecular weight limit (i.e. as measured prior to the binding of a metal or metals) of 1500 Daltons and a higher molecular weight limit sufficiently low so as to allow the composition to remain soluble (even with bound metal(s)).

In a further aspect of the composition(s) outlined above the trace metals include at least one of iron, manganese, copper, cobalt, magnesium or nickel.

In a further aspect of the composition(s) outlined above the metal chelating composition is used for disease treatment within an animal, including a fish or a human, that has a disease attributable to one or more members of the group comprising a disease causing microbial cell(s), a cancer cell(s) or a parasitic organism(s).

In a further aspect of the composition(s) outlined above the microbial cell is a fungal cell from the Eukaryota fungi kingdom.

In a further aspect of the composition(s) outlined above the fungal cell is *Candida albicans*.

In a further aspect of the composition(s) outlined above the microbial cell is a bacterial cell from the Bacteria domain.

In a further aspect of the composition(s) outlined above the bacterial cell is *Staphylococcus aureus*.

In a further aspect of the composition(s) outlined above the cancer cell has arisen from within the animal to be treated.

In a further aspect of the composition(s) outlined above the parasitic organism is one of the group of parasitic animals capable of causing parasitic infections in man or other animals.

In a further aspect of the composition(s) outlined above the cells are those of the animal itself, the animal having a metal-related disease, the chelating composition chelating a portion of the offending metal related to the metal-related disease and providing improvement in the metal-related disease.

Another embodiment of the invention provides for a treatment method for controlling the growth of a disease causing cell(s) or organism(s) within an animal comprising:

i) administering a chelating composition onto or into an animal including a human or fish suffering from disease as caused from one or more of a pathogenic microbial or cancer cell or a parasitic organism within or with on the animal;

wherein chelating composition comprises suitable metal binding aspect(s) affixed to or incorporated within the structure of a suitable carrier material such that the resulting composition has chelating activity for a metal, optionally essential, and remains soluble in aqueous (metal containing) medium (such as a composition as set forth above);

wherein the chelating composition is administered in a pharmaceutically effective amount so as to bind at least a portion of at least one (trace) metal element in the animal and in the external cellular environment of the pathogenic cell or organism, the trace metal being essential to the pathogenic cell or organism being treated. In accordance with a purpose of the treatment the (trace) metal is potentially able to become at least less accessible to the pathogenic cell or organism as a result of the use of the chelating composition and as a further result the ability of the pathogenic cell or organism to cause disease in the animal is inhibited.

In a further aspect of the method outlined above the pathogenic microbial cell is a fungal cell and member of the Eukaryota fungi kingdom.

In a further aspect of the method outlined above the fungal cell is the fungus *Candida albicans*.

In a further aspect of the method outlined above the pathogenic microbial cell is a bacterial cell and member of the Bacteria domain.

In a further aspect of the method outlined above the bacterial cell is the bacterium *Staphylococcus aureus*.

In a further aspect of the method outlined above the suitable metal binding chemical groups are selected from the carboxyl, hydroxyl, phenolate, catecholate, hydroxamate or hydroxypyridinone chemical groups.

In a further aspect of the method outlined above the chelating composition contains functional metal binding groups similar to those of deferoxamine or deferiprone.

In a further aspect of the method outlined above the chelating composition has a carrier material selected from vinylpyrrolidone, dextran, starch, styrene or acrylamide.

In a further aspect of the method outlined above the chelating composition comprises metal binding groups of 3-hydroxy-pyridin-4-one incorporated into a carrier comprised of vinylpyrrolidone, dextran, starch or acrylamide.

In a further aspect of the method outlined above the chelating composition that remains soluble in aqueous medium has a lower molecular weight limit (as measured prior to the binding of a metal or metals) of 1500 Daltons and a higher molecular weight limit sufficiently low so as to allow the composition to remain soluble.

In a further aspect of the method outlined above the trace metal is iron, manganese, copper, cobalt, magnesium or nickel.

Another embodiment of the invention provides for a chelating composition suitable for chelating one or more essential metals, the chelating composition being soluble in aqueous medium and comprised of one or more suitable metal binding chemical groups affixed to or incorporated into the structure of a suitable carrier material, such that the resulting chelating composition is able to bind one or more metals, remains soluble in aqueous medium with its bound metal or metals and, the metal or metals so-bound to the chelating composition become less available for uptake and use by undesirable cells or by parasitic organisms. This type of composition may, for example, be potentially exploited against undesirable cells or undesirable parasitic organisms requiring such (trace) metal or metals for their growth and the undesirable cells or undesirable parasitic organisms possess a degree of resistance to the action of one or more chemical anti-cellular agents or chemical preservative agents and, the purpose of exploiting the chelating composition is to compromise the ability of the cells or parasitic organisms to grow and resist the action of the chemical anti-cellular agents or chemical preservative agents.

In a further aspect of the composition(s) outlined above the essential metal is a trace essential metal.

In a further aspect of the composition(s) outlined above the suitable metal binding chemical groups are selected from one or more of the carboxyl, hydroxyl, phenolate, catecholate, hydroxamate or hydroxypyridinone chemical types.

In a further aspect of the composition(s) outlined above the chelating composition contains metal binding chemical groups possessing similarity to those of deferoxamine or deferiprone.

In a further aspect of the composition(s) outlined above the chelating composition has a carrier material comprised of vinylpyrrolidone, dextran, starch, styrene or acrylamide.

In a further aspect of the composition(s) outlined above the chelating composition comprises metal binding chemical groups of 3-hydroxy-pyridin-4-one incorporated into a carrier material comprised of vinylpyrrolidone, dextran, starch or acrylamide.

In a further aspect of the composition(s) outlined above the composition has a lower molecular weight limit (as measured prior to the binding of a metal or metals) of 1500 Daltons and a higher molecular weight limit sufficiently low so as to allow the composition to remain soluble.

In a further aspect of the composition(s) outlined above the trace metals include at least one of iron, manganese, copper, cobalt, magnesium or nickel.

In a further aspect of the composition(s) outlined above the metal chelating composition is used for treatment within an animal, including a human or a fish, that has a disease as caused from one or more of a disease causing microbial cell or cancer cell or a parasitic organism, the disease causing microbial cell or cancer cell or a parasitic organism has some degree of resistance to the action of the chemical anti-cellular agent.

In a further aspect of the composition(s) outlined above the microbial cell is a fungal cell from the Eukaryota fungi kingdom.

In a further aspect of the composition(s) outlined above the fungal cell is *Candida albicans*.

In a further aspect of the composition(s) outlined above the microbial cell is a bacterial cell from the Bacteria domain.

In a further aspect of the composition(s) outlined above the bacterial cell is *Staphylococcus aureus*.

In a further aspect of the composition(s) outlined above the cancer cell has arisen from within the animal to be treated.

In a further aspect of the composition(s) outlined above the parasitic organism is one of the group of parasitic animals capable of causing parasitic infection in man or other animals.

In a further aspect of the composition(s) outlined above the aqueous medium is within a commercial product for use by a human or other animal(s) (e.g. mammals, birds, fish, etc.) comprising a chemical preservative, the cells are microbial cells of spoilage causing fungi or bacteria, and, the chelating composition binds one or more of the metals that are required for the growth of the microbial spoilage cells. One potential result of the binding of the (trace) metal or metals by the chelating composition is that the action of the chemical preservative agent for controlling growth of the microbial spoilage cells is potentially enhanced.

In a further aspect of the composition(s) outlined above the preservative agent is a compound that inhibits microbial growth or is a chemical antioxidant.

Another embodiment of the present invention provides for a method for controlling the growth of a disease causing cell or organism within an animal, comprising:

administering an effective amount chelating composition, either before, during or after the administration of at least one anti-cellular agent, to an animal including a human, fish or bird suffering from disease as caused from one or more of a pathogenic microbial or cancer cell or a parasitic organism within the animal, the anti-cellular agent being selected on the basis of its known activity against the pathogenic microbial or cancer cell or a parasitic organism;

wherein the chelating composition comprises suitable metal binding chemical groups affixed to or incorporated within the structure of a suitable carrier material such that the resulting composition has chelating activity for a metal and remains soluble in aqueous containing media, such as a composition as defined above. One purpose of administrating the chelating composition may be to bind (at least) a portion of at least one (trace) metal element in the animal and in the external cellular environment of the pathogenic cell or organism, the trace metal being essential to the pathogenic cell or organism being treated so that the (trace) metal becomes less accessible to the pathogenic cell or organism as a result of the use of the chelating composition so as to enhance the action of the anti-cellular agent due to the trace metal being less available to the pathogenic cell or organism, and as a result the ability of the pathogenic cell or organism to cause disease in the animal is inhibited.

In a further aspect of the method outlined above the pathogenic microbial cell is a fungal cell and member of the Eukaryota fungi kingdom.

In a further aspect of the method outlined above the fungal cell is the fungus *Candida albicans*.

In a further aspect of the method outlined above the pathogenic microbial cell is a bacterial cell and member of the Bacteria domain.

In a further aspect of the method outlined above the bacterial cell is the bacterium *Staphylococcus aureus*.

In a further aspect of the method outlined above the suitable metal binding chemical groups are selected from the carboxyl, hydroxyl, phenolate, catecholate, hydroxamate or hydroxypyridinone chemical groups.

In a further aspect of the method outlined above the chelating composition contains functional metal binding groups similar to those of deferoxamine or deferiprone.

In a further aspect of the method outlined above the chelating composition has a carrier material comprised of vinylpyrrolidone, dextran, starch, styrene or acrylamide.

In a further aspect of the method outlined above the chelating composition comprises metal binding groups of 3-hydroxy-pyridin-4-one incorporated into a carrier comprised of vinylpyrrolidone, dextran, starch or acrylamide.

In a further aspect of the method outlined above the chelating composition that remains soluble in aqueous containing media has a lower molecular weight limit (as measured prior to the binding of a metal or metals) of 1500 Daltons and a higher molecular weight limit sufficiently low so as to allow the composition to remain soluble.

In a further aspect of the method outlined above the trace metal is iron, manganese, copper, cobalt, magnesium or nickel.

In a further aspect of the method outlined above the anti-cellular agent is one or more of an antimicrobial, anti-metabolite, anti-viral, anti-parasitic or anti-cancer agent.

In a further aspect of the method outlined above the antimicrobial, anti-metabolite, anti-viral, anti-parasitic or anti-cancer anti-cellular agent is selected from: penicillins, cephems, cephalosporins, carbapenems, penems, monocyclic ß-lactams, macrolides, ketolides, streptogramins, lincosamines, fluoroquinolones, coumarin antibiotics, glycopeptides, monobactams, lipoglycopeptides, ansamycins, phenicols, nitroimidazoles, fosfomycin, orthosomycins, paldimycin, primycin, benzonaphthyridones, mutilins, oxazolidinones, sulfonamides, nitrofurans, polyenes, benzylpyrimidines, bacitracin, chloramphenicol, tetracyclines, erythromycins, clindamycin, gentamicin, aminoglycosides, mupirocin, fusidic acid, spectinomycin, rifamycins, quinolones, ciprofloxacin, nitrofurantoin, 5-fluorocytosine, trimethoprim, sulfonamides, trimetrexate, imidazoles, triazoles, zidovudine, ganciclovir, vidirabine, acyclovir, amantidines, idoxuridine, foscarnet, trifluridine, ribavirin, penciclovir, stavudine, quinolines, quinoline derivatives, diaminopyrimidines, halofantrine, pyrimethamine, chloroguanide, quinine, atovaquone, diloxanide furoate, eflornithine, melarsoprol, metrondiazole, nitrofurans, pentamidine, other diamidines, sodium stibogluconate, suramin, nitrosourea, fluorouracil bleomycin, anti-microbial peptides, antimicrobial surfactants, halogens, aldehydes or, chemically related compounds and/or derivatives of any of the foregoing.

In a further aspect of the method outlined above the soluble chelator is administered to the animal such that the soluble chelator is within a semi-permeable device, the soluble chelating composition within the device is retained in the device and has the ability to bind iron and/or other trace metals such that the concentration of the iron and/or other trace metal or metals outside of the device and in the external cellular environment of the pathogenic cell or organism becomes lower and less accessible to the pathogenic cell or organism as a result of the use of the chelating composition, the trace metal being essential to the pathogenic cell or organism being treated and the action of the anti-cellular agent is enhanced due to the iron or trace metal being less available to the pathogenic cell or organism and, as a result the ability of the pathogenic cell or organism to cause disease in the animal is somewhat inhibited.

Another embodiment of the present invention provides for a chelating composition, suitable for chelating one or more essential metals, optionally trace essential metals, the chelating composition being soluble in aqueous media and comprised of one or more suitable metal binding chemical groups affixed to or incorporated into the structure of a suitable carrier material, such that the resulting chelating composition binds one or more trace metals and remains soluble in aqueous media with its bound trace metal or metals. One purpose of the exploitation of the composition, is potentially that the (trace) metal or metals so-bound to the chelating composition become less available for uptake and use by cells or parasitic organisms, the cells or parasitic organisms requiring such trace metal or metals for an activity and, as a result of the action of the chelating composition the ability of the cells or parasitic organisms to continue the activity is inhibited.

In a further aspect of the composition(s) outlined above the suitable metal binding chemical groups are selected from one or more of the carboxyl, hydroxyl, phenolate, catecholate, hydroxamate or hydroxypyridinone chemical types.

In a further aspect of the composition(s) outlined above the chelating composition contains metal binding chemical groups possessing similarity to those of deferoxamine or deferiprone.

In a further aspect of the composition(s) outlined above the chelating composition has a carrier material comprised of vinylpyrrolidone, dextran, starch, styrene or acrylamide.

In a further aspect of the composition(s) outlined above the chelating composition comprises metal binding chemical groups of 3-hydroxy-pyridin-4-one incorporated into a carrier material comprised of vinylpyrrolidone, dextran, starch or acrylamide.

In a further aspect of the composition(s) outlined above the composition has a lower molecular weight limit (as measured prior to the binding of a metal or metals) of 1500 Daltons and a higher molecular weight limit sufficiently low so as to allow the composition to remain soluble.

In a further aspect of the composition(s) outlined above the trace metals includes at least one of iron, manganese, copper, cobalt, magnesium or nickel.

In a further aspect of the composition(s) outlined above the aqueous media is within a human or another animal including a bird or a fish.

In a further aspect of the composition(s) outlined above the cell is a fungal cell from the Eukaryota fungi kingdom.

In a further aspect of the composition(s) outlined above the fungal cell is *Candida albicans*.

In a further aspect of the composition(s) outlined above the cell is a bacterial cell from the Bacteria domain.

In a further aspect of the composition(s) outlined above the bacterial cell is *Staphylococcus aureus*.

In a further aspect of the composition(s) outlined above the cell is a cancer cell that has arisen within the animal to be treated.

In a further aspect of the composition(s) outlined above the parasitic organism is one of the group of parasitic animals capable of causing parasitic infection in man or other animals.

In a further aspect of the composition(s) outlined above the activity of the cell or parasitic organism is that of forming a biofilm of growth on a surface of the body of the human or other animal or on a medically implanted device within the body.

In a further aspect of the composition(s) outlined above a portion of the suitable carrier material is part of the medically implanted device.

In a further aspect of the composition(s) outlined above the activity is that of resisting the activity of a chemical anti-cellular agent or chemical preservative agent.

In a further aspect of the composition(s) outlined above the chemical anti-cellular agent is one of: penicillins, cephems, cephalosporins, carbapenems, penems, monocyclic ß-lactams, macrolides, ketolides, streptogramins, lincosamines, fluoroquinolones, coumarin antibiotics, glycopeptides, monobactams, lipoglycopeptides, ansamycins, phenicols, nitroimidazoles, fosfomycin, orthosomycins, paldimycin, primycin, benzonaphthyridones, mutilins, oxazolidinones, sulfonamides, nitrofurans, polyenes, benzylpyrimidines, bacitracin, chloramphenicol, tetracyclines, erythromycins, clindamycin, gentamicin, aminoglycosides, mupirocin, fusidic acid, spectinomycin, rifamycins, quinolones, ciprofloxacin, nitrofurantoin, 5-fluorocytosine, trimethoprim, sulfonamides, trimetrexate, imidazoles, triazoles, zidovudine, ganciclovir, vidirabine, acyclovir, amantidines, idoxuridine, foscarnet, trifluridine, ribavirin, penciclovir, stavudine, quinolines, quinoline derivatives, diaminopyrimidines, halofantrine, pyrimethamine, chloroguanide, quinine, atovaquone, diloxanide furoate, eflornithine, melarsoprol, metrondiazole, nitrofurans, pentamidine, other diamidines, sodium stibogluconate, suramin, nitrosourea, fluorouracil bleomycin, anti-microbial peptides, antimicrobial surfactants, halogens, aldehydes or, chemically related compounds and/or derivatives of any of the foregoing.

In a further aspect of the composition(s) outlined above the chemical preservative agent inhibits microbial growth or is a chemical antioxidant.

Another embodiment of the present invention provides for a method for preserving an aqueous containing product from microbial or oxidative chemical degradation and spoilage comprising:

i) treating the product or at least one aqueous component used to formulate the product in a first step by contacting the product or the aqueous component with an insoluble chelating composition using a suitable contacting means, so as to allow at least a portion of the iron or other metal(s), optionally trace metal(s) in the product or the aqueous component to be bound by the insoluble chelating composition, followed by separation of the insoluble composition from the product or the aqueous component thereby forming a first-treated product or a first-treated aqueous component, so that at least a portion of the iron or other metal(s) is recovered separate with the insoluble chelating composition and, the first-treated product or the first-treated aqueous component of the product is reduced in its content of iron or other metal(s); ii) treating the first-treated product or first-treated aqueous component of the product from step (i) in a second step, either before or after being added to the other product components so as to result in a product formulation with all its components together, with a soluble chelating composition, the soluble chelating composition for binding at least a portion of iron or other metal(s) as still present and not having been removed by the first treatment step. One purpose of binding the iron or other trace metal by the soluble chelating composition in step (ii) is reduce metal accessibility to microbial spoilage organisms or for participation in oxidative chemical reactions causing degradation of the product constituents; lack of metal accessibility to the microbial spoilage organisms is intended to inhibit their growth abilities in the product or become more sensitive to the action of a chemical preservative agent or agents as contained in the treated product, and as a result, the product is enhanced with respect to being better preserved from microbial or oxidative spoilage.

In a further aspect of the method outlined above the insoluble chelating composition is comprised of one or more suitable metal binding chemical groups affixed to or incorporated into the structure of a suitable carrier material, such that the resulting chelating composition is insoluble in aqueous media and has ability to binds one or more (trace) metals.

In a further aspect of the method outlined above the suitable metal binding chemical groups are selected from one or more of the carboxyl, hydroxyl, phenolate, catecholate, hydroxamate or hydroxypyridinone chemical types.

In a further aspect of the method outlined above the metal binding chemical groups possess similarity to those of deferoxamine or deferiprone.

In a further aspect of the method outlined above the suitable carrier material is comprised of vinylpyrrolidone, dextran, starch, styrene, acrylamide or silica, so that the final chelating composition is insoluble in aqueous containing media.

In a further aspect of the method outlined above the insoluble chelating composition comprises metal binding chemical groups of 3-hydroxy-pyridin-4-one incorporated into a carrier material comprised of vinylpyrrolidone, dextran, starch or acrylamide.

In a further aspect of the method outlined above the trace metals includes at least one of iron, manganese, copper, cobalt, magnesium or nickel.

In a further aspect of the method outlined above the soluble chelating composition is comprised of one or more suitable metal binding chemical groups affixed to or incorporated into the structure of a suitable carrier material, such that the resulting chelating composition is soluble in aqueous media and has ability to binds one or more trace metals.

In a further aspect of the method outlined above the soluble chelating composition of step ii is contained within a semi-permeable device added to the first-treated product or first-treated aqueous component of the product such that the chelating composition is of a molecular weight too high so as to allow it to permeate from the device into the bulk of the first-treated product or first-treated aqueous component of the product containing the device while the aqueous media of the first-treated product or first-treated aqueous component of the product can permeate and exchange through the device and thereby contact the soluble chelating composition within the device and, the soluble chelating composition within the device has the ability to bind iron and/or other trace metals contained in the first-treated product or first-treated aqueous component of the product so as to remove at least a portion of the iron or other trace metals from the first-treated product or first-treated aqueous component of the product such that the concentration of the iron and/or other trace metal or metals in the first-treated product or first-treated aqueous component of the product as external to the device is(or are) somewhat lowered.

In a further aspect of the method outlined above the insoluble chelating composition of step i is contained within a permeable device that retains the insoluble chelating composition within the device and does not permit the insoluble chelating composition to physically enter the bulk of the first-treated product other than from being present within the device and, the device containing the insoluble chelating composition is not separated from the first-treated product so that at least a portion(s) of the iron or the other (trace) metal(s) is/are retained in the insoluble chelating composition within the device and, the first-treated product as external to the device is somewhat reduced in its content of iron or other (trace) metal(s).

In a further aspect of the method outlined above the suitable metal binding chemical groups are selected from one or more of the carboxyl, hydroxyl, phenolate, catecholate, hydroxamate or hydroxypyridinone chemical types.

In a further aspect of the method outlined above the metal binding chemical groups possess similarity to those of deferoxamine or deferiprone.

In a further aspect of the method outlined above the suitable carrier material is comprised of vinylpyrrolidone, dextran, starch, styrene or acrylamide that is soluble in aqueous containing media.

In a further aspect of the method outlined above the soluble chelating composition comprises metal binding chemical groups of 3-hydroxy-pyridin-4-one incorporated into a carrier material comprised of vinylpyrrolidone, dextran, starch or acrylamide.

In a further aspect of the method outlined above the chelating composition that remains soluble in aqueous containing media has a lower molecular weight limit (as measured prior to the binding of a metal or metals) of 1500 Daltons and a higher molecular weight limit sufficiently low so as to allow the composition to remain soluble.

In a further aspect of the method outlined above the trace metals includes at least one of iron, manganese, copper, cobalt, magnesium or nickel.

In a further aspect of the method outlined above the microbial spoilage organisms are either fungal or bacterial.

In a further aspect of the method outlined above the fungal or bacterial organisms have a degree of resistance to the chemical preservation agent or agents as mentioned above.

In a further aspect of the method outlined above the chemical preservative agent or agents is selected from: propionic acid and propionates; sorbic acid and sorbates; benzoic acid and benzoates; sodium diacetate; lactic acid; sulfur dioxide, sulfites; sodium nitrite; sodium chloride; aldehyde containing or releasing compounds, mercury containing compounds; antioxidants; detergents such as quaternary ammonium compounds and soluble ion complexing agents such as ethylene-diamine-tetra-acetic acid.

In a further aspect of the method outlined above the other trace metal that is less accessible for participation in oxidative chemical reactions causing degradation of the product constituents is one of copper, manganese, cobalt, or nickel.

Another embodiment of the present invention provides for a method for preserving an aqueous containing product from microbial or oxidative chemical degradation and spoilage wherein the product is treated with a soluble chelating composition, the soluble chelating composition binds (a portion of) iron or other (trace) metal(s) present in the product creating a lowered metal accessibility to the microbial spoilage organisms and inhibits their growth abilities and activities in the product and/or the spoilage organisms become more sensitive to the action of a chemical preservative agent or agents as contained in the product, and as a result, the product is enhanced with respect to being better preserved from microbial or oxidative spoilage.

In a further aspect of the method outlined above the soluble chelating composition is comprised of one or more suitable metal binding chemical groups affixed to or incorporated into the structure of a suitable carrier material, such that the resulting chelating composition is soluble in aqueous media and has ability to binds one or more trace metals.

In a further aspect of the method outlined above the suitable metal binding chemical groups are selected from one or more of the carboxyl, hydroxyl, phenolate, catecholate, hydroxamate or hydroxypyridinone chemical types.

In a further aspect of the method outlined above the metal binding chemical groups possess similarity to those of deferoxamine or deferiprone.

In a further aspect of the method outlined above the suitable carrier material is comprised of vinylpyrrolidone, dextran, starch, styrene or acrylamide that is soluble in aqueous containing media.

In a further aspect of the method outlined above the soluble chelating composition comprises metal binding chemical groups of 3-hydroxy-pyridin-4-one incorporated into a carrier material comprised of vinylpyrrolidone, dextran, starch or acrylamide.

In a further aspect of the method outlined above the chelating composition that remains soluble in aqueous containing media has a lower molecular weight limit (as measured prior to the binding of a metal or metals) of 1500 Daltons and a higher molecular weight limit sufficiently low so as to allow the composition to remain soluble.

In a further aspect of the method outlined above the trace metals includes at least one of iron, manganese, copper, cobalt, magnesium or nickel.

In a further aspect of the method outlined above the microbial spoilage organisms are either fungal or bacterial.

In a further aspect of the method outlined above the fungal or bacterial organisms have a degree of resistance to the chemical preservation agent or agents as mentioned above.

In a further aspect of the method outlined above the chemical preservative agent or agents is selected from: propionic acid and propionates; sorbic acid and sorbates; benzoic acid and benzoates; sodium diacetate; lactic acid; sulfur dioxide, sulfites; sodium nitrite; sodium chloride; aldehyde containing or releasing compounds, mercury containing compounds; antioxidants; detergents such as quaternary ammonium compounds and soluble ion complexing agents such as ethylene-diamine-tetra-acetic acid.

In a further aspect of the method outlined above the other trace metal that is less accessible for participation in oxidative chemical reactions causing degradation of the product constituents is one of copper, manganese, cobalt, or nickel.

In a further aspect of the method outlined above the soluble chelating composition is contained within a semipermeable device added to the product such that the chelating composition is of a molecular weight too high so as to allow it to permeate from the device into the bulk of the product containing the device while the aqueous media of the product can permeate and exchange through the device and thereby contact the soluble chelating composition within the device and, the soluble chelating composition within the device has the ability to bind iron and/or other trace metals contained in the product so as to remove at least a portion of the iron or other trace metals from the product such that the concentration of the iron and/or other trace metal or metals of the product as external to the device is(or are) somewhat lowered.

Another embodiment of the present invention provides for a chelating composition suitable for chelating one or more essential metals, optionally trace metals, the chelating composition being soluble in aqueous media and comprised of one or more suitable metal binding chemical groups affixed to or incorporated into the structure of a suitable carrier material, such that the resulting chelating composition binds one or more metals and remains soluble in aqueous media with its bound trace metal or metals and, wherein the metal binding chemical group is a portion of a monomer group comprising a metal binding monomer, the metal binding monomer is mixed with a second monomer group and, the two monomer groups are polymerized so that the resulting co-polymer remains soluble in aqueous solution and has metal chelating activity.

In a further aspect of the composition(s) outlined above the metal binding chemical group is selected from the phenolate/catecholate, hydroxamate or hydroxypyridinone chemical classes.

In a further aspect of the composition(s) outlined above the metal binding chemical group is similar to the metal binding chemical groups of clinically used desferal or deferiprone.

In a further aspect of the composition(s) outlined above the second monomer group is selected from the acrylamide, styrene or pyrrolidone chemical classes.

In a further aspect of the composition(s) outlined above the metal chelating activity is for iron, manganese, copper, cobalt, magnesium or nickel.

In a further aspect of the composition(s) outlined above the composition has a molecular weight of between $1.5 \times 10^3$ and $10^7$ Daltons prior to the binding of metal.

In a further aspect of the composition(s) outlined above the metal binding monomer is 3-hydroxy-1-(β-methacrylamidoethyl)-2-methyl-4(1H)-pyridinone, the second monomer is 1-vinyl-2-pyrrolidone and the final chelating composition is a linear soluble co-polymer of the two monomer groups.

In a further aspect of the composition(s) outlined above the metal binding monomer is 3-hydroxy-1-(β-methacrylamidoethyl)-2-methyl-4(1H)-pyridinone, the second monomer is N,N-dimethyl-acrylamide and the final chelating composition is a linear soluble co-polymer of the two monomer groups In a further aspect of the composition(s) outlined above the composition either being insoluble or soluble wherein pyrrolidone, polyvinylpyrrolidone or starch is an aspect of the composition or co-polymer, these aspects are capable of binding iodine and the composition is treated with iodine such that iodine is chemically bound to the pyrrolidone, polyvinylpyrrolidone or starch containing aspects of the composition or co-polymer and the resultant iodine-containing chelating composition has anti-cellular properties contributed by the iodine in addition to the metal chelating aspect of the metal chelating composition.

DETAILED DESCRIPTION

Figure 1:
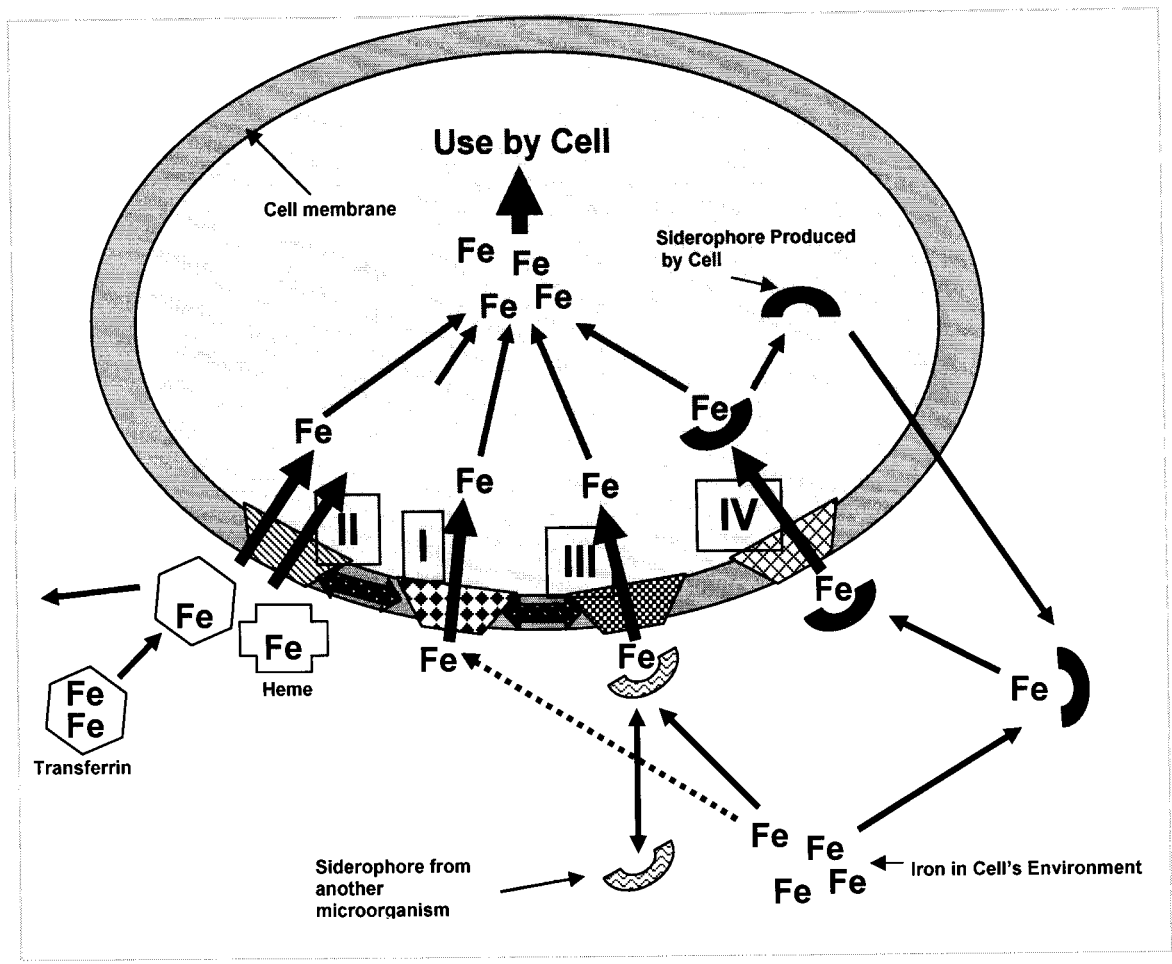
FIG. 1 is a schematic illustrative of a typical iron uptake mechanism.

The following is an illustrative description of embodiments of the invention and are not intended to be limiting but merely illustrative of the invention and aspects thereof. It will be appreciated that theory discussed below is non-limiting and is not intended to be binding. Chelating compositions and methods of iron sequestering are illustrative and not limiting.

It will be appreciated that all of the Fe acquisition mechanisms of cells have key aspects that are located in the cell membrane at or near the cell's surface and function to acquire Fe from the cell's external environment. Chelating compositions including certain of those described herein that are either too large in molecular size (formula weight) to be internalized directly by the cell and/or that are too large or bulky to be physically accessed by the cell surface receptor/transport Fe systems, would be less available as Fe sources for bacteria, fungal or animal cells. Such non- or less-accessible chelators, if also of acceptable or higher Fe binding strength relative to the Fe binding affinities of other conventional chelators, siderophores or transferrins, may potentially provide a harder-to-access sink for iron in the external environment of the cell, therefore making Fe much less available to the cell.

Somewhat similar aspects exist for other trace essential metals including copper, manganese, nickel, cobalt and magnesium. These other metals are required to varying degrees by cells and, for a cell requiring one of these metals, the cell must also acquire the metal from the cell's external environment. It has therefore been determined that chelating compositions that bind one of these other trace metals in the external environment of a cell that requires the metal and binds this metal in a form that is less accessible for uptake by the cell may also result in reduced availability of that metal for the cell.

Targeting spoilage or pathogenic cells on the basis of denying them iron or other growth-essential metal(s) provides an innovative approach to product preservation and/or disease control. Thus, interference of the offending cell's growth through metal deprivation may potentially prevent microbial spoilage or sensitize a spoilage microbe to the action of other chemical preservatives. As well, interference of a pathogenic cell's growth through Fe deprivation might increase the efficiency of normal host defence mechanisms against the pathogen or alternatively, sensitize the pathogenic cell to the activities a range of other anti-cellular agents, such as conventionally used antibiotic or cancer chemotherapy agents. It should be noted that for the purposes of this disclosure, growth of a cell can be distinguished from an activity of a cell, the later possibly not necessarily requiring growth. Thus, a non-growing cell may still be alive and carry out an activity such as degrading an anti-cellular agent, etc.

Other activities of cells that may be affected by certain compositions disclosed herein include production of secondary metabolites from microbes, i.e. those that are influenced in their production by the amount of iron or other metals available to the cell, for example flavin production in yeast such as *Candida* species or antibiotic production in *Actinomycetes* species. The chelating compositions exemplified herein have been found to be useful or potentially useful for restricting iron to cells so as to promote production of secondary metabolites such as flavin in *Candida albicans*.

Yet another activity of cells that may potentially be affected by chelating compositions is the general inflammatory response that is caused by the combined activities of various cells in the bodies of humans or other animals. The chelating activity of certain of the chelating compositions reducing or easing the inflammation response through sequestering iron or other metals that in part participate in aspects of the inflammatory response.

Certain of the chelating compositions have been found useful or potentially useful for interfering with cell growth, i.e. cell replication, on one hand and cell activity on the other hand.

Without wishing to be bound by theory, it has been determined that a common problem restricts the use of previously disclosed chelators for controlling growth and activities of cells. This problem is related not to the soluble nature of these compounds but to the relatively small molecular size of these chelator compounds such that these compounds can be taken up into cells and/or be accessed for their iron at the surface of a cell, i.e. through use of the mechanisms shown in FIG. 1 and Table 1. It has also been determined that this problem may be overcome by providing higher molecular weight chelating compositions that incorporate acceptable metal binding properties (e.g. properties as efficient as or better than those of existing chelators) in compositional structures which are nevertheless still soluble in aqueous medium. For example, a chelating composition may have chelator aspect(s) affixed to a carrier material such that the resulting chelating composition is sufficiently large in molecular size so as not to be taken up readily into cells or be readily accessed for its iron by cells but yet still sufficiently low in molecular size so to remain soluble in the aqueous environment surrounding the cell to be treated. In this regard, one form of the chelating compositions includes chemical chelating aspects incorporated into compositions with other carrier constituents or in copolymer matrices, so as to provide water soluble chelating compositions of a molecular size sufficiently low so as to remain soluble in the aqueous environment surrounding the cell to be treated but yet sufficiently high in molecular size so as to no longer have the chelating composition or its associated metal (e.g. iron) accessible to the uptake mechanisms of the cells being treated.

The co-polymerization of metal chelating molecules within a co-polymer including compositions containing 3-hydroxy-pyridin-4-one to obtain an insoluble chelating composition have been reported (Feng, M, 1996). However, such previously disclosed chelating compositions also relate to compositions which are insoluble in aqueous media and such prior art does not teach, suggest or provide any incentive with respect to soluble chelating compositions disclosed herein.

One embodiment provides for the production of a chelating composition containing a chelating activity, including activity provided by 3-hydroxy-pyridin-4-one or other related hydroxypyridinones or other types of chelating groups such as hydroxyl, carboxyl, phenolate or hydroxamate, in a form that is soluble in aqueous media, such that the composition with any associated iron is not accessible as an iron source to the cell being treated with the chelating composition.

Bacterial adhesion and biofilm formation are now recognized to be important cellular activities for bacterial and fungal pathogens during disease development (Hentzer M., M. Givskov, 2003). Iron chelators such as desferrioxamine have been shown to increase twitching motility and restrict biofilm formation in the laboratory (Singh et al, 2002). Appropriate restriction of iron supply during the early stages of bacterial or fungal disease could interfere with a pathogenic cell's activity of establishing a biofilm for example on an epithelial surface of the respiratory or urogenital tracts or on indwelling medical devices such as a urinary catheter. Iron chelators as disclosed in the prior art would suffer the same limitations for use in interfering with the activity of microbial adhesion for pathogens for those pathogens that can utilize these chelators or otherwise obtain iron from these. As outlined above, it would be advantageous to have available, chelating compositions incorporating, for example, the metal binding properties of low molecular weight chelators in a structure where these chelators are affixed to a carrier that results in these being of sufficiently high molecular size so as not to be taken up into cells or be otherwise accessed for their iron by a cell. The use of such chelating compositions could thus interfere with the microbial activity of biofilm formation during pathogenesis and therefore interfere with the pathogenic process providing a basis for treating or preventing infection. Such chelating compositions may potentially also interfere with the microbial activity of biofilm formation and provide means for controlling biofilm growth in industrial systems handling food, beverages or water that are known to be prone to problems of biofilm growth and contamination. Here again, a preferred form of the chelating compositions of the present invention includes, for example, known chemical chelating aspects incorporated into compositions with other carrier constituents or in copolymer matrices, so as to provide water soluble chelating compositions of a molecular size sufficiently low so as to remain soluble in the aqueous environment surrounding the cell to be treated but sufficiently high in molecular size so as to no longer have the chelating composition or its associated iron accessible to the uptake mechanisms of the cells being treated.

Antibiotic resistance as a cellular activity of medically important bacteria such as *Staphylococcus aureus* or *Clostridium difficile* has now become a major problem in medicine (Martinez, J. L., and F. Baquero. 2002). Similar problems have arisen for fungal pathogens such as *Candida albicans* (Prasad, R. and K. Kapoor. 2005). These so-called 'super-bugs' can be highly resistant to a range of antibiotics and are a major disease threat. Conventional antibiotics, such as the penicillins, are anti-cellular agents and they target various cellular functions. Resistance to anti-cellular agents arises through cellular activities that can inactivate or exclude the antibiotic employed. Restriction of iron to bacteria in the laboratory has been shown to increase the sensitivity of for example *Actinobacillus actinoycetemcomitans* to minocycline (Grenier, D., M.-P. Huot, D. Mayrand. 2000) or for *Pseudomonas aeruginosa* to tobramycin (Singh P. K., M. R. Parsek, E. P. Greenberg, M. J. Welsh. 2002) and for fungi such as for example *Candida albicans*. Therefore, iron withholding through use of appropriate chelators might target pathogens with normal antibiotic sensitivities as well as antibiotic resistant strains causing infection in animals including humans. Iron chelators as disclosed in the prior art would again suffer the same limitations for use in augmenting the action of antibiotics in animals as these can be used by some pathogens as a source of iron. Once again, it would be advantageous to provide chelating compositions incorporating, for example, the metal binding properties of low molecular weight chelators in a structure where these chelators are affixed to a carrier that results in these being of sufficiently high enough molecular size (formula weight) so as not to be taken up into cells or otherwise accessed for their iron by a cell. The use of such chelating compositions could interfere with the problematic microbial activity of the pathogenic cell overcoming the effects of an antibiotic as used to control it. Thus, chelating compositions could enhance the action of antibiotics. Yet again, one form of the chelating compositions includes, for example, known chemical chelating aspects incorporated into compositions with other carrier constituents or within copolymer matrices, so as to provide water soluble chelating compositions of a molecular size sufficiently low so as to remain soluble in the aqueous environment surrounding the cell to be treated but yet sufficiently high in molecular size so as to no longer have the chelating composition or its associated iron accessible to the uptake mechanisms of the cells being treated. Here the soluble chelating composition interferes with the cell's ability to obtain iron and thus allow improved action of an antibiotic for controlling the cell's pathogenesis.

Parasites also have requirements for iron and the availability of iron during infection with *Trypanosoma cruzi* has been shown to be a determinant in disease outcome (Lalonde and Holbein, 1984). *Plasmodium falciparum* from chloroquine resistant malarial infection has been shown to be sensitive in vitro to the cycline antibiotics (tetracycline, minocycline, etc) and quinolones (norfloxacin, oxfloxacin). The activities of these antibiotics were decreased when excess iron was provided suggesting their activity was partly related to iron metabolism of the parasite (Pradines et al, 2001). Thus, appropriate restriction of iron supply during parasitic disease could interfere with the parasitic organism's growth or activity in relation to susceptibility to anti-parasitic agents. However, once again, the iron chelators as disclosed in the prior art such as in U.S. Pat. Nos. 5,256,676 and 6,825,204, suffer the same limitations as discussed above for their use in interfering with the growth or activity of parasitic pathogens. The parasites could still obtain iron in the presence of the previously disclosed chelating substances. Yet again, one form of the chelating compositions includes, for example, chemical chelating aspects incorporated into compositions with other carrier constituents or within copolymer matrices, so as to provide water soluble chelating compositions of a molecular size sufficiently low so as to remain soluble in the aqueous environment surrounding the cell to be treated but yet sufficiently high in molecular size so as to no longer have the chelating composition or its associated iron accessible to the uptake mechanisms of the parasitic organism or cells being treated.

Transferrin (and related lactoferrin) is part of a natural class of proteins produced by vertebrate animals for iron transport and defence and the transferrin proteins are of a molecular weight size greater than 1500 Daltons, However, the transferrins are accessible to many microbial pathogens, cancer cells and most animal cells because most vertebrate animal cells and various microbial pathogens possess surface receptors that effectively recognize and bind these iron proteins as part of their normal iron nutrition mechanisms, i.e., for obtaining iron as carried by the transferrin proteins (see FIG. 1 and Table 1). Transferrin or lactoferrin (or portions of these molecules) have been proposed for anti-microbial therapeutic purposes (U.S. Pat. Nos. 7,446,089 and 5,656,591), However, they have limited utilities because they are exploitable by a variety of bacterial and fungal pathogens as sources of iron. A further form of the chelating compositions disclosed herein includes chemical chelating aspects incorporated into compositions with other carrier constituents or in copolymer matrices, so as to provide water soluble chelating compositions of a molecular size sufficiently low so as to remain soluble in the aqueous environment surrounding the cell to be treated but yet sufficiently high in molecular size so as to no longer have the chelating composition or its associated metal (e.g. iron) accessible to the cell surface receptor or other iron uptake mechanisms of the cells being treated. One form of the chelating compositions include water soluble polymeric chelating compositional structures with a molecular size similar to that of the transferrin proteins, i.e., approximately 100 kDa, and with a greater number of iron binding sites than the two available in the transferrins. Additionally, these iron binding sites have higher efficiency such that the chelating composition binds iron more strongly than the transferrins and is also not recognizable or accessible by/at the cell surface receptors that exist to bind the transferrins and to remove iron from the transferrins. In accordance with a particular aspect, soluble chelating compositions may be administered to an animal, for example to the eye or vagina as a component of eye drops or vaginal medications, where these soluble chelating compositions bind a metal or metals, example a trace metal, adding to the natural defence mechanisms as for example provided by lactoferrin at these locations in the body.

The prospects for using iron chelation for cancer therapy have been reviewed (Buss et al, 2003). However, the use of conventional chelators in the treatment of cancer have produced ineffective results (Buss et al, 2003) possibly because the medical chelators utilized were developed originally for relieving excess iron from patients, pathologically overloaded with iron and these chelators may not have the needed efficiencies (i.e. sufficiently high molecular weight or iron binding strengths) to effectively deal with the iron acquisition mechanisms of cancer cells. These findings point to the need for chelating compositions with effective affinity for iron coupled with physical forms of chelating compositions that cannot be accessed by cancer cells. Cancer cells like non-cancerous cells of the body utilize transferrin as a source of iron as needed for their growth and possess surface receptors to dock transferrin and unload its iron to the interior of the cell for use. Chelating compositions with effective affinity for iron (i.e., exceeding those of the normal animal iron carrier protein, transferrin or lactoferrin for example) and as presented in the external aqueous environment of a cancer cell and that are not accessible by the cell receptors or transportable into the cancer cell could provide the basis of new therapies that could suppress cancer cell growth or alter cancer cell activity so as to sensitize cancer cells to other anti-cellular agents (chemical and radiation).

Iron chelators and chelating compositions as disclosed in the prior art such as in U.S. Pat. No. 5,663,201, would suffer the same limitations as discussed above for use in interfering with the growth or activity of cancer cells. Here again, it is potentially advantageous to provide chelating compositions incorporating the metal binding properties, for example, of low molecular weight chelators into a structure where these chelators are affixed to a carrier that results in these being of sufficiently high enough molecular size so as not to be taken up into cancer cells or otherwise recognizable and accessed for their iron by a cancer cell but yet of sufficiently low molecular size so as to facilitate their introduction into a patient and have these provide iron removal in the aqueous environment immediately surrounding the cancer cell to be treated. The use of such chelating compositions could thus interfere with the cancer cell's growth and activity during pathogenesis and also improve the action of other anti-cancer agents, at least on the basis of intercepting Fe as would be delivered by transferrin.

In one embodiment, soluble chelating compositions may, for example, comprise a suitable chemical chelating aspect attached to a suitable soluble carrier material so as to provide a water soluble chelating composition. Suitable chelating aspects include but are not limited to a carboxyl, hydroxyl, phenolate, catecholate, hydroxamate or hydroxypyridinone chemical group. Suitable carrier materials include but are not limited to starch, dextran, styrene, acrylamide or pyrrolidone. A specific embodiment includes compositions comprised of a suitable chemical chelating group incorporated as a chelating monomer group in a copolymer matrix with a suitable polymer forming monomer group such as, for example, pyrrolidone, styrene or acrylamide.

It has been previously disclosed in U.S. Pat. No. 4,530,963 that the removal of iron from a growth medium, utilizing insoluble chelating compositions that are used to treat the medium and then physically removed from the medium with their sequestered iron, is useful for achieving the inhibition of microbial growth in a treated medium. Similar relationships might be expected to hold for other essential metals to varying degrees since metals such as copper, manganese, cobalt, nickel, magnesium, zinc etc. play important roles in growth of cells including pathogenic microbes and cancer cells (see for example; Huber et al. 1990). However, in the case of utilizing insoluble chelating compositions to sequester iron in a vertebrate host it is not practical to physically add or remove the chelator with its sequestered iron. Chelating compositions capable of being administered into a vertebrate host and sequestering iron within the host must be in a form that can be administered to the host, i.e., ideally in a form that leaves these soluble in the host's fluids. Additionally, soluble chelating compositions, owing to their solubilities in aqueous environments in which they are utilized, as opposed to insoluble chelating compositions, can better penetrate the reaches of the aqueous environment in terms of better accessing the iron in the treatment environment and, soluble chelating compositions therefore possess improved iron chelating gathering characteristics for the iron in the environment being treated. Chelating compositions of a soluble nature for use in vertebrate hosts are aspects of the present invention. Here, one form of the chelating compositions, may, for example, include chemical chelating aspects (such as for example taught in U.S. Pat. No. 4,530,963, the entire contents of which is incorporated herein by reference) incorporated into compositions with other carrier constituents or in copolymer matrices, so as to provide water soluble chelating compositions of a molecular size sufficiently low so as to remain soluble in the aqueous environment surrounding the cell to be treated but sufficiently high in molecular size so as to no longer have the chelating composition or its associated iron accessible to the uptake mechanisms of the cells being treated. In this regard, a soluble chelating composition may have a molecular size which is generally sufficiently large so as not to be readily taken up into a bacterial, fungal, parasitic or cancer cell or readily recognized and bound by cell surface receptors that could facilitate Fe removal from the composition to deliver iron to the internal aspects of the cell. On the other hand, there is no limit to the upper molecular size (i.e. weight) limit, provided only that the upper size is sufficiently low so as to still permit the chelating composition to remain soluble in aqueous containing media and environments of intended use; the molecular size may for example be >1500 Daltons (e.g. at least 5,000 up to 3,000,000 Daltons). The soluble chelating composition even when provided as a low molecular weight composition would not be recognized by the cells receptor and uptake mechanisms.

Another problem associated with the use of insoluble chelating compositions as used to physically remove iron from an aqueous medium is that residual iron left behind in the treated medium after use of the insoluble chelating composition may still be present at sufficient concentrations to allow some growth of certain microorganisms. The use of soluble chelating compositions that bind iron in a form not accessible to cells may be a means to overcome this problem and could be utilized to preserve media on their own or preserve media that had been treated in a first step with an insoluble chelating composition.

A further embodiment provides a soluble chelating composition of sufficient molecular size so as not to be significantly permeable into the target cell and not accessible to surface associated iron acquisition mechanisms of a target cell but yet can sequester metals in the aqueous environment surrounding the target cell being treated. As a result of this action the cell being treated becomes somewhat deficient in iron and as a result of this iron deficiency the action of various other anti-cellular chemical compounds that exert their action within the target cell is enhanced.

Conventional chemical therapies for microbial and parasitic diseases and cancer employ a range of anti-cellular chemical compounds (apart from radiation therapy) and these agents generally permeate and enter various internal aspects of the target cell and there, target various aspects of the cellular growth and respiration machinery of the pathogenic cell. These agents can be broadly summarized into classes as below:

a) those antimicrobials that inhibit bacterial or fungal cell wall synthesis such as antibacterial penicillins, cephalosporins, carbapenems, cycloserine, vancomycin, bacitracin, imidazoles, and ethambutol and antifungal agents such as cilofungin and pradimicins;

b) those antimicrobials that cause bacterial or fungal cell membrane damage, for example detergents such as polymixins and colistemethate and antifungal agents such as nystatin and amphotericin B;

c) those antimicrobials that inhibit lipid synthesis such as the antifungal agents as the azole class of compounds represented by fluconazole;

d) those antimicrobials that inhibit bacterial protein synthesis such as chloramphenicol, tetracyclines, erythromycins, clindamycin, gentamicin, aminoglycosides, mupirocin, fusidic acid, and spectinomycin;

e) those antimicrobials that inhibit nucleic acid synthesis or metabolism such as rifamycins, quinolones, ciprofloxacin, nitrofurantoin and the antifungal 5-fluorocytosine;

f) the anti-metabolites such as trimethoprim, sulfonamides, trimetrexate, imidazoles, and triazoles;

g) the antiviral agents such as zidovudine, ganciclovir, vidirabine, acyclovir, amantidines, idoxuridine, foscarnet, trifluridine, ribavirin, penciclovir, and stavudine;

h) the anti-parasitic agents such as chloroquine, other quinolines, quinoline derivatives, diaminopyrimidines, halofantrine, pyrimethamine, chloroguanide, quinine, atovaquone, diloxanide furoate, eflornithine, melarsoprol, metrondiazole, nitrofurans, pentamidine, other diamidines, sodium stibogluconate, and suramin;

i) the anticancer agents including irradiation or chemical agents such as alkylating agents such as nitrosourea, and lomustine antimetabolites such as the pyrimidine analog fluorouracil, and antibiotics such as bleomycin.

For the purposes of the present disclosure the above agents are referred to as anti-cellular agents. These anti-cellular agents generally permeate into the target cell and then injure and ultimately kill the target cell, be it a pathogenic fungal, bacterial, parasite or cancer cell. Pathogenic cells of all types are known to develop resistance mechanisms to anti-cellular agents through various mechanisms including: neutralization (degradation of agent), exclusion (prevention of agent's permeation into the cell) and/or use of repair mechanisms that repair damage inflicted from the anti-cellular agent. These resistance mechanisms can result in the loss of efficacy of a specific anti-cellular agent or result in the requirement for very high or more prolonged dosages of the agent to control the pathogenic cell. It should be appreciated that such resistance mechanisms would be more avid and responsive in target cells that have sufficient quantities of essential nutrients for unrestricted growth. A specific embodiment provides for creating stress on a pathogenic cell through restricting its supply of essential metals, such as iron. As a result of this iron or metal deprivation stress, the pathogenic cell's abilities to grow or carry out the activities associated with resisting anti-cellular agents may be impaired. The result of utilizing a chelating composition, such as those disclosed herein, with the anti-cellular agent may provide an alternative ability of controlling the growth or activity of the cell treated or an enhanced cell killing effect from the anti-cellular agent.

Chelating compositions which are the subject of the present disclosure may be utilized either alone or in conjunction with other anti-cellular agents for the control of growth or activities of pathogenic cells or the killing of these cells. The chelating compositions may be administered into the body, for example by injection or, be applied onto the body for example onto epithelial surfaces. Chelating compositions may also be combined into wound dressing materials to help control microbial growth at wound sites or with the polymeric materials utilized to manufacture indwelling medical devices so as to interfere with microbial growth on such devices. The applications of chelating compositions disclosed herein within wound dressing materials such as hydrogels, sutures, bandages, etc, or as coatings or incorporated within the polymer materials used to manufacture catheters, shunts and other indwelling medical devices is also considered. Here owing to the solubility of the chelating compositions in aqueous media these can diffuse into wound sites or from medical devices to bind metal and restrict its availability to pathogenic cells. The soluble chelating compositions may for example be mixed with an anti-cellular agent or anti-cellular agents, the soluble chelating composition serving as an excipient component in the admixture and thereby serving to maintain or enhance the bioavailability or activity of the anti-cellular agent.

In another aspect, the metal binding chemical groups can be incorporated into a medical device by direct use of one of the component material of the device itself as a carrier material for incorporating metal binding chemical groups.

In yet another aspect the soluble chelating composition is presented for use within a semi-permeable device which permits iron or other metals in the aqueous environment surrounding the device to permeate and enter the device and there to become bound by the chelating composition while the soluble chelating composition itself is retained within the device along with any of the metal it has bound, thus leaving the metal or metals as external to the device unavailable in the aqueous environment of the cell to be treated.

The problems of resistance to anti-cellular agents in pathogenic cells, whether microbes or cancer cells, are important health issues and are growing in their severity. Another aspect thus relates to an approach to chemical therapy for microbial diseases and cancer. This approach provides means for taking advantage of the roles that trace essential metals play in cellular activities, growth and replication and how the interference in cellular respiration, growth and repair can complement and augment the actions of other anti-cellular agents that permeate into and inflict cellular injury inside targeted cells. In particular, the inventors have determined that application of a chelating composition, that is not permeable to the pathogenic cell and sequesters iron from the extracellular environment of the pathogenic cell in the presence of anti-cellular antibiotic agents, renders pathogenic antibiotic-resistant clinically isolated *Staphylococcus aureus* or *Candia albicans* cells more susceptible to anti-cellular agents to which they had previously developed significant resistance. This method applies to other pathogenic bacterial, fungal or cancer cells as well as to parasitic organisms.

In addition, certain of the compositions and the methods for employing these applies to controlling spoilage or fouling microorganisms, wherein iron or other metal removal or sequestration provides assistance to other preservative chemicals.

Conventional chemical preservative agents are added to various health and consumer products to preserve these for use. Spoilage of such products can represent health and safety issues. These products are susceptible to microbial spoilage from organisms that gain entry to the products and grow because of the product's aqueous composition and content of nutrients that allow growth of the spoilage organisms. Such nutrients include trace essential metals that are needed for the growth of spoilage organisms.

Conventional chemical preservatives include but are not restricted to; propionic acid and propionates; sorbic acid and sorbates; benzoic acid and benzoates; sodium diacetate; lactic acid; sulfur dioxide, sulfites; sodium nitrite; sodium chloride; aldehyde containing or releasing compounds, mercury containing compounds; antioxidants; detergents such as quaternary ammonium compounds and soluble ion complexing agents such as ethylene-diamine-tetra-acetic acid. Chelating compositions are also provided that take up a portion of a trace metal that is required for a spoilage microorganism and, as a result of making the supply of a trace metal less available, the sensitivity of the spoilage microorganism to one or more of the conventional preservative agents is increased.

In an aspect the present invention thus relates to a (in vivo and/or in vitro) metal loving or binding (i.e. metal (ion) sequestering, metal (ion) quarantining or metal (ion) camouflaging) composition or substance, (i.e. a metal chelating composition or substance) for inhibiting (e.g. denying) cellular uptake (i.e. through the cell wall or cell membrane) and/or use (within the cell) of one or more (biologically) essential metals, said metal loving or binding composition or substance being soluble (as described herein) in an aqueous medium (e.g. water, fruit preservation syrup, blood plasma, nutrient, etc.), said metal loving or binding composition or substance having a molecular weight of from 1500 to $10^7$ Daltons (e.g. 10,000 Daltons, 3,000,000 Daltons, 5,000-10,000 Daltons, 150,000-2,500,000 Daltons, etc.).

The metal loving or binding composition or substance may comprise one or more (suitable or desired) metal binding ligand (e.g. (known—see prior art incorporated herein) organic chelating) groups. The metal loving or binding (i.e. sequestering, quarantining or camouflaging) composition or substance may, for example, comprise a metal binding ligand component (moiety or portion) which is covalently fixed to or which is covalently incorporated into (e.g. as a monomer segment(s) of) a (suitable or desired) substrate component. The substrate component (e.g. known polymeric type substrate) may be present in any desired or necessary proportion which is sufficient to provide the composition or substance (along with the ligand component) with the desired or necessary molecular weight and solubility (i.e. the necessary or desired solubility both alone (i.e. metal free) and, as desired or necessary, when associated with bound metal or metals). A metal binding ligand moiety (portion or component) may for example be able to preferentially bind one or more essential metals relative to the metal uptake mechanism of a cell. If iron is the essential metal, the metal binding ligand moiety (portion or component) may for example be provided by one or more (known)

siderophoric or chelating groups or compounds (e.g. material mentioned in the patents referred to herein the entire contents of which are incorporated herein by reference).

The present invention in accordance with various aspects provides a method for inhibiting microbial growth in an aqueous medium (e.g. water, fruit preservation syrup, blood plasma, nutrient medium, etc.) containing Fe (or other essential metal(s) ions) by lowering the Fe (or other essential metal(s)) content as available to a cell or organism for its use thereof to less than 0.1 µM characterized in that said medium is contacted with a siderophoric (or metal loving or binding) composition soluble in said aqueous medium, said soluble siderophoric or metal loving or binding) composition having a molecular weight of from 1500 to $10^7$ Daltons.

A (soluble) chelator substance may be added or incorporated into an aqueous medium to be treated in any suitable or effective amount keeping in mind its intended purpose as described herein, i.e. in an amount so as to provide the desired or necessary control of cell growth or affect a cell activity. The amount of chelator substance to associate with an aqueous medium will depend, for example, on the type of aqueous system to be treated (in vitro or in vivo), the contained amount of iron (and/or other essential metal) to be bound up by the chelator substance, the type of cell to be targeted (bacteria, yeast, parasite or cancer cell) and the desired outcome, i.e. be this to prevent growth or to affect a particular cell activity. For example, addition of only 25 µg/ml of soluble chelator has been shown to increase (by more than ten-fold) the sensitivity of *Candida albicans* in vitro to the anti-cellular agent fluconazole (as shown in example 19). It should be understood that higher amounts of soluble chelator would be expected to be required to control growth of *C. albicans*, i.e., when control of growth is the desired outcome and when not in conjunction with addition of an anti-cellular agent. Thus, complete control of growth of this same yeast for 48 hours required a soluble chelator dosage of 500 µg/ml as shown in example 18. It should be appreciated that administration of soluble chelator to a human or other animal would require sufficient dosage of administration so as to achieve effective concentrations at the site in the host where the soluble chelator is to function (example in the blood or vaginal fluid). Generally, sufficient soluble chelator would be added or administered so as to achieve an excess (for example, a two to five fold excess) of iron (and/or other essential metal) chelating capacity over the amount of iron (and/or other metal) concentration present in the aqueous environment (at the site) to be treated when control of growth is the desired outcome and when used without a anti-cellular agent. It should be appreciated that smaller effective dosages would be expected if the soluble chelator is administered in conjunction with an anti-cellular agent for the purpose of lowering the resistance of the cell to the anti-cellular agent.

Iodine is a well known antimicrobial agent and is often used as a disinfectant in the form of iodine solution (tincture) or as iodine bound to polyvinylpyrrolidone (iodine povidone solution). Iodine binding to starch is also well known. The antimicrobial activity of iodine is chemically distinct and different from the activities of the metal chelating compositions disclosed herein. It has been determined that certain of the metal chelating compositions and, in particular, those containing a structural aspect of pyrrolidone or starch, can also bind iodine and retain the iodine such that the resulting iodine-containing soluble or insoluble chelating compositions as disclosed retain their metal binding activities and also include an iodine associated antimicrobial activity, i.e., in addition to their metal binding activities.

It is of course to be understood herein that the various components of the above described substance (able to take up metal) are to be chosen keeping in mind the environment of intended use thereof; i.e. the components are to be selected such that the substance works in an acceptable fashion in the environment of intended use. For example, in the context of pharmaceutical or food applications of the present invention, the various components of the above described substance are to be chosen so as to provide a pharmaceutically acceptable substance (able to take up metal), an acceptable food additive (e.g., preservative) substance (able to take up metal), or the like. A substance as described herein may, for example, have applications in relation to cosmetics (i.e. as a preservative type material) and would thus have to be acceptable in the context of this type of application.

It is to be understood that the certain compositions of the present invention may be used to treat diseases of man and other animals including fish, including microbial infections caused by bacteria, fungi and parasites (and including strains of these microbes with a degree of resistance as acquired by them to conventional anti-cellular agents as used to treat the disease) and cancers arising within man and other animals including fish.

There is considerable evidence that iron also plays an important role in the overall inflammatory responses of man and other animals (De Domenico et al 2010), the iron participating in production of reactive oxidation mechanisms that are part of the inflammatory response as produced by certain cells of the animal body, this inflammation occurring for example during infection or cancer or on its own. It is to be understood that certain of the compositions may be used control the activity of inflammatory cells so as to treat the inflammation that may occur on its own, i.e., as an inflammatory condition or disease, or inflammation that accompanies other diseases of man and other animals including fish, including microbial infections caused by bacteria, fungi and parasites.

There is also evidence that production of certain secondary metabolites as desirable natural products from microorganisms for medicinal (e.g., antibiotic compounds) or industrial use (e.g. citric acid or flavins, see for example Hsu, et al, 2011) can be an activity of cells that is influenced by iron, for example such that their production can be enhanced under conditions of low iron availability to microorganisms. It would also be potentially useful to place additional new desirable genes coding for desired products within known genetic operons that are regulated by iron in order to provide a means for regulating and enhancing production of such genetically engineered gene products. A potential benefit here is that production of a secondary metabolite or an iron regulated product can be triggered into production by the producing cell by low iron supply or by iron withdrawal under conditions when adequate supplies of C, N, S etc are still available for incorporation into the desired product. It is to be understood that the compositions of the present invention can be used control the activity of secondary metabolite production in microorganisms by their binding of iron, i.e., where such secondary metabolite production activity is influenced by available iron supply in the environment of the producing microorganism.

It is to be understood herein that the expression "metal loving or binding composition or substance", or any derivative thereof, in relation to an aqueous medium, is a reference to a chelating composition or substance having the ability to bind, in an aqueous environment, one or more essential metals so as to inhibit (and/or deny) cell access to the essential metal(s).

It is to be understood herein that the reference to "essential metals" is a reference to the metal(s) needed by a cell for growth and/or maintenance.

It is further to be understood herein, that if a "group of substances", "group of substituents", "range" of a particular characteristic (e.g. molecular weight, temperature, concentration, time and the like) or the like is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example,

- with respect to the number of carbon atoms, the mention of the range of 1 to 10 carbon atoms is to be understood herein as incorporating each and every individual number of carbon atoms as well as sub-ranges such as, for example, 1 carbon atoms, 3 carbon atoms, 4 to 6 carbon atoms, etc.;
- with respect to a molecular weight (e.g. avg. molecular weight) greater than 1500 Daltons, it is to be understood herein that (subject to the solubility requirement mentioned herein) the molecular weight may be far ranging e.g. a molecular weight greater than 5000 Daltons, a molecular weight greater than 1500 Daltons, a molecular weight of 1500 to 10,000,000 Daltons, a molecular weight of 15,000 to 10,000,000 Daltons, a molecular weight of 1500 to 3,000,000 Daltons, a molecular weight of 1500 to 2,000,000 Daltons, a molecular weight of 10,000 Daltons, a molecular weight of 80,000 Daltons, a molecular weight of 100,000 Daltons, etc.
- with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;
- and similarly with respect to other parameters such as concentrations, elements, etc.

It is thus to be understood herein for example that a reference to an alkyl group comprising from 1 to 10 carbon atoms includes and specifically refers to an octyl, a straight chain alkyl group of 6 to 10 carbon atoms (e.g. $C_{6-10}$), to a "straight alkyl group of 1 to 6 carbon atoms", namely, for example, methyl, ethyl, propyl, butyl, pentyl, and hexyl; and so on.

It is further to be understood herein for example that a reference to an alkyl group comprising from 1 to 10 carbon atoms includes and specifically refers to a "branched alkyl group of 3 to 6 carbon atoms"; that a reference to a "branched alkyl group of 3 to 6 carbon atoms" includes for example, without limitation, iso-butyl, tert-butyl, 2-pentyl (i.e. 2-methyl-butyl), 3-pentyl (i.e. 3-methyl-butyl; isopentyl), neopentyl, tert-pentyl, etc; and so on.

It is in particular to be understood herein for example classes or sub-classes are inherently defined herein in every and any possible manner whatsoever. It is thus for example to be understood that the definitions herein with respect to any class, sub-class or individual include both positive as well as negative or exclusionary definitions i.e. the definitions herein incorporate any and all definitions that may be worded as positively including particular individual compounds, classes or sub-classes and/or as excluding particular individual compounds, classes or sub-classes or combinations thereof; for example an exclusionary definition for the definition of a compound formula may read as follows: "provided that when one of $R_1$ and $R_2$ is methyl and the other is H, $R_8$ may not occupy the 2 position".

EXAMPLES

The following non-restrictive examples are provided to illustrate various aspects of the present invention while not in any way being intended to limit the scope of the invention.

Example 1; Synthesis of 1-aminoethyl-3-hydroxy-2-methyl-4(1H)-pyridinone (AHMP) Chelator Intermediate Useful for Preparation of Chelating Compositions The synthesis of this chelator intermediate has been described elsewhere (Feng et al, 1993). The following procedure was employed for this example:

To a one liter flask were added: 0.35 mole 3-hydroxy-2-methyl-4-pyrone, 450 ml methanol, 0.4 mole benzyl chloride and a solution of 0.37 mole sodium hydroxide in 50 ml water. The mixture was refluxed for six hours and then stirred at room temperature overnight. The methanol was then evaporated using vacuum and the residue was mixed with 200 ml water and then extracted using three separate 100 ml aliquots of methylene chloride. The three methylene chloride extracts were pooled and washed with three changes of 50 ml 5% NaOH and then three changes of 50 ml water. The extract was then dried over solid $MgSO_4$. Following filtration to remove the $MgSO_4$ and evaporation of the solvent, 76.6 gram of crude 3-benzyloxy-2-methyl-4-pyrone was recovered. This material was then mixed in a one-liter flask with 500 ml ethanol, 1.65 mole ethylenediamine and 2 ml water and stirred overnight at room temperature. The solvent and excess ethylenediamine were removed under reduced pressure to yield a yellow-brown oily liquid that was triturated with 400 ml water to yield 65.5 g yellow 1-(2-aminoethyl)-3-benzyloxy-2-methyl-4-(1H)-pyridinone. This product was dissolved in 500 ml 6 M HCl and the solution was stirred at room temperature overnight. A pale yellow product solid was recovered after evaporation to dryness in vacuum. This was re-dissolved in 500 ml 6 M HCl and stirred at room temperature for four days and evaporated to dryness again. The solid residue was washed with approximately 50 ml acetone to obtain the crude product. Because this was difficult to filter, 150 ml 4 M HCl and 70 ml ethanol were added and the mixture was refluxed until the solids had dissolved. The product was then re-crystallized by storage in a refrigerator, washed with acetone dried and weighed. The final AHMP product was yellow.

Example 2; Synthesis of Soluble Chelating Composition Comprising Hydroxyethyl Starch or Dextran with 3-hydroxy-pyridin-4-one Active Chelating Groups Provided by AHMP Soluble hydroxyethyl starch or dextran samples at 10% (wt/vol) aqueous solution were oxidized separately with 0.1 M sodium metaperiodate to yield reactive aldehyde groups on the polymers. After removal of low molecular weight substances (<10,000 Dalton material) by dialysis, the activated soluble polysaccharides were reacted with a 0.1 M solution of AHMP, 1-aminoethyl-3-hydroxy-2-methyl-4 (1H)-pyridinone, prepared as in example 1, at neutral to slightly alkaline pH. The Schiff bases formed between the amino groups of the chelating agent and the aldehyde groups on the polymers were then reduced with excess sodium cyanoborohydride so as to stabilize the linkage, while any remaining un-reacted aldehyde groups on the starch or dextran were reduced with the excess sodium borohydride. The soluble chelating polymer composition product was purified by dialysis in a Visking dialysis bag against water over 48 hours with 5 changes of the dialysis water. The molecular weight cut-off size for the dialysis tubing used was 10,000 Daltons and thus the final soluble chelating composition products retained in the dialysis bags had a molecular weight of ≥10,000 Daltons. The iron-binding ability of the resultant chelating compositions was confirmed by addition of excess iron-citrate solution to a test portion of the chelating composition. The tested portion turned red indicating binding of iron to the chelator pyridinone groups within the polymers. It should be appreciated that no steps other than to dialyze away materials of a size less than 10,000 Daltons were taken with these sample preparations. It should be noted that further steps to provide more refined, i.e. lower molecular weight (e.g. greater than 1500 Daltons) product or smaller product size distributions could be taken using conventional known methods such as ultrafiltration and/or chromatographic purification, i.e., in relation to obtaining a more refined product of a given molecular weight distribution. The final chelating compositions were obtained by lyophilization so as to remove the suspending water and the dry products were found to be freely soluble in water for use.

Example 3; Synthesis of 3-hydroxy-1-(β-methacrylamidoethyl)-2-methyl-4(1H)-pyridinone (MAHMP) Chelating Monomer Useful for Preparation of Chelating Compositions The synthesis of this chelating monomer intermediate has been previously described elsewhere (Feng et al. 1993). The following procedure was employed for this example:

To a 250 ml flask fitted with a magnetic stirrer and a dropping funnel, 12.1 g AHMP prepared as in example 1 was dissolved in 50 ml water. Thereafter, 0.18 mole triethylamine (ET3N) and 100 ml $CH_3CN$ (acetonitrile) were added and the mixture was placed on an ice bath. Acryloyl chloride ($C_3H_3ClO$), 0.06 mole, was then added drop-wise over 1.5 hr while the mixture was kept in the ice bath. Following this addition, stirring was continued for two hours at room temperature. The mixture was then evaporated to dryness to remove solvents and the solid residue was washed with 250 ml hot acetone, filtered and the filtrate was evaporate to remove approximately 100 ml of the acetone and then it was stored in a refrigerator overnight. An initial needle crystal of triethyl-ammonium chloride, if formed, was removed by filtration and the filtrate was returned to the refrigerator where a solid formed. The solid was filtered and washed with 10 ml chloroform ($CHCl_3$) and then dissolved in 1:1 methanol:ethanol; a total of 12 ml added drop-wise to the flask at 80° C. in a water bath. The final MAHMP was obtained by re-crystallization at 4° C. from the alcohol mixture.

Example 4; Synthesis of a Soluble Chelating, Composition Comprising an Active Pyridinone Chelating Agent Co-Polymerized in a Soluble Linear Polyvinylpyrolidone Polymeric Carrier MAHMP, 3-hydroxy-1-(β-methacrylamidoethyl)-2-methyl-4(1H)-pyridinone (2.5 mmole, 0.59 g), prepared as in example 3, was dissolved in 50 ml water in a 250 ml flask with a mechanical stirrer at 50° C. to provide a first monomer (chelating monomer). A second monomer, 1-vinyl-2-pyrrolidone (54 mmole), was added while stirring and the mixture was cooled to room temperature. Ammonium persulfate (0.057 g) was added and after the flask was flushed with nitrogen for 20 minutes, N,N,N',N'-tetramethylethylenediamine (0.1 ml) was added and the polymerization was carried out for 2 hours at 40° C. The co-polymer solution was enclosed in a Visking dialysis bag and dialyzed against distilled water for 48 hour with five changes of fresh water. The molecular weight cut-off size for the particular dialysis tubing used was approximately 10,000 Daltons and thus the final product retained in the dialysis bag had a molecular weight of ≥10,000 Daltons. The final chelating composition product was obtained by lyophilization and was found to be freely soluble in water. Three separate sample preparations as made by the above procedure were tested for their average molecular weights using X-Ray diffraction. These tests for molecular weight were performed independently at the Commonwealth Scientific and Industrial Research Organisation (CSIRO) laboratories in Perth Western Australia. The three samples of soluble chelating compositions had the following measured molecular weights: $1.73 \times 10^5$ Daltons; $3.32 \times 10^5$ Daltons and $8.2 \times 10^4$ Daltons. These results illustrate the repeatability of the synthesis procedure to prepare soluble chelating compositions and the relative uniformity of the molecular size of the soluble composition produced; the three trials resulted in soluble composition of average molecular weights of between 80,000 to 330,000 Daltons. It should be appreciated that no steps other than to dialyze away materials of a size less than 10,000 Daltons were taken with these sample preparations. Further steps to provide a more refined, i.e. lower molecular weight or smaller product size distribution could be taken using conventional known methods such as ultrafiltration and/or chromatographic purification, i.e., in relation to obtaining a more refined product of a given desired molecular weight distribution.

Example 5; Synthesis of an Insoluble Chelating Composition Comprising an Active Chelating Agent Co-Polymerized in a Cross-Linked Insoluble Polyacrylamide Polymeric Carrier The procedure provided was to achieve an acrylamide polymer containing active chelating groups (of 3-hydroxy-4(1H)-pyridinone group functionality) interspersed with dimethyl-acrylamide monomer groups and with 2% chain cross-linking with bis-acrylamide groups. It is noted that varying degrees of ligand density and cross-linking can be achieved through appropriate adjustments of the proportions used of monomer and cross-linking groups. MAHMP, 3-hydroxy-1-(β-methacrylamidoethyl)-2-methyl-4(1H)-pyridinone (3.0 mmole, 0.715 g), prepared as in example 3, was dissolved in 50 ml water in a 250 ml flask with a mechanical stirrer at 50° C. N,N-dimethyl-acrylamide (54 mmole, 5.6 ml) and N,N'-methylene-bis-acrylamide (3.0 mmole, 0.505 g) was added while stirring and the mixture was cooled to room temperature. Ammonium persulfate (0.137 g), n-hexane (100 ml), carbon tetrachloride (25 ml) and sorbitan monostearate (100 mg) were added and the mixture was flushed with $N_2$ for 20 min. Then, N,N,N',N'-tetramethylethylenediamine (0.2 ml) was added and the polymerization reaction was carried out for 2 hours. The resulting polymer was filtered, washed with water (150 ml), 2-propanol (50 ml), and acetone (50 ml). The acetone-washed product was dried in a vacuum oven at 60° C. overnight. This insoluble chelating composition provided for comparison testing with the soluble version as from Example 6.

Example 6; Synthesis of a Soluble Chelating Composition Comprising an Active Chelating Agent Co-Polymerized in a Linear Soluble Polyacrylamide Polymeric Carrier The procedure provided was to achieve a soluble acrylamide polymer containing active chelating groups of 3-hydroxy-4(1H)-pyridinone group functionality, interspersed with dimethyl-acrylamide monomer groups as in example 5 but with no chain cross-linking. MAHMP, 3-hydroxy-1-(β-methacrylamidoethyl)-2-methyl-4(1H)-pyridinone (2.5 mmole, 0.59 g), prepared as in example 3, was dissolved in 50 ml water in a 250 ml flask with a mechanical stirrer at 50° C. N,N-dimethyl-acrylamide (54 mmole, 5.6 ml) was added while stirring and the mixture was cooled to room temperature. Ammonium persulfate (0.057 g) was added and after the flask was flushed with nitrogen for 20 minutes, N,N,N', N'-tetramethylethylenediamine (0.1 ml) was added and the polymerization was carried out for 2 hours at 40° C. The polymer solution was enclosed in a Visking dialysis bag and dialyzed against distilled water for 48 hour with five changes of fresh water. The molecular weight cut-off size for the dialysis tubing used was approximately 10,000 Daltons and thus the final product retained in the dialysis bag had a molecular weight of ≥10,000 Daltons. The final product was obtained by lyophilization and was found to be freely soluble in water. It should be appreciated that no steps other than to dialyze away materials of a size less than 10,000 Daltons were taken with this sample preparation. Further steps to provide a more refined, i.e. lower molecular weight or smaller product size distribution could be taken using conventional known methods such as ultrafiltration and/or chromatographic purification, i.e., in relation to obtaining a more refined product of a given molecular weight distribution.

This soluble version of the chelating composition differed from the composition of Example 5 only through the absence of polymer cross-linking and thus comparison testing of these was useful to establish characteristics and benefits of the soluble version vs. the insoluble version.

Example 7; Comparative Physical Properties of Insoluble and Soluble Chelating Compositions Physical properties of the insoluble and soluble chelating compositions, as prepared in Examples 5 and Example 6, respectively, were characterized for typical samples, with results as follows:
Insoluble chelating composition from Example 5:
(1) Appearance: Yellow spherical beads (metal unloaded), Red spherical beads (iron loaded)
(2) Particle size: beads of diameter 129 μm (unloaded, dry), diameter 121 μm (iron loaded, dry)
(3) Solubility in water: none, insoluble suspension of particle beads
(4) Density of active chelating agent: 842 μmoles/g of chelating composition (as determined from iron binding capacity tests).
Soluble chelating composition from Example 6:
(1) Appearance: Yellow fibers; straw colored solution (no added iron); clear red solution (added iron)
(2) Molecular weight: $(4.32\pm0.2)\times10^6$ Dalton as determined by X-Ray diffraction
(3) Solubility in water: 36 mg/ml
(4) Density of active chelating agent: 862 μmoles/g of chelating composition (as determined from iron binding capacity tests).

These results showed that both the soluble and insoluble chelating polymeric compositions from the above examples had similar capacities for chelation, i.e., the density of incorporated chelating activity per unit of mass of polymer carrier was similar but these compositions had different physical properties. The soluble version had a molecular weight of approx. 4,000,000 Daltons but remained soluble in water. Other samples of the soluble chelating composition had molecular weights of as low as 80,000 Daltons.

Example 8; Stability of Chelating Group Incorporation in Chelating Compositions

Figure 2:
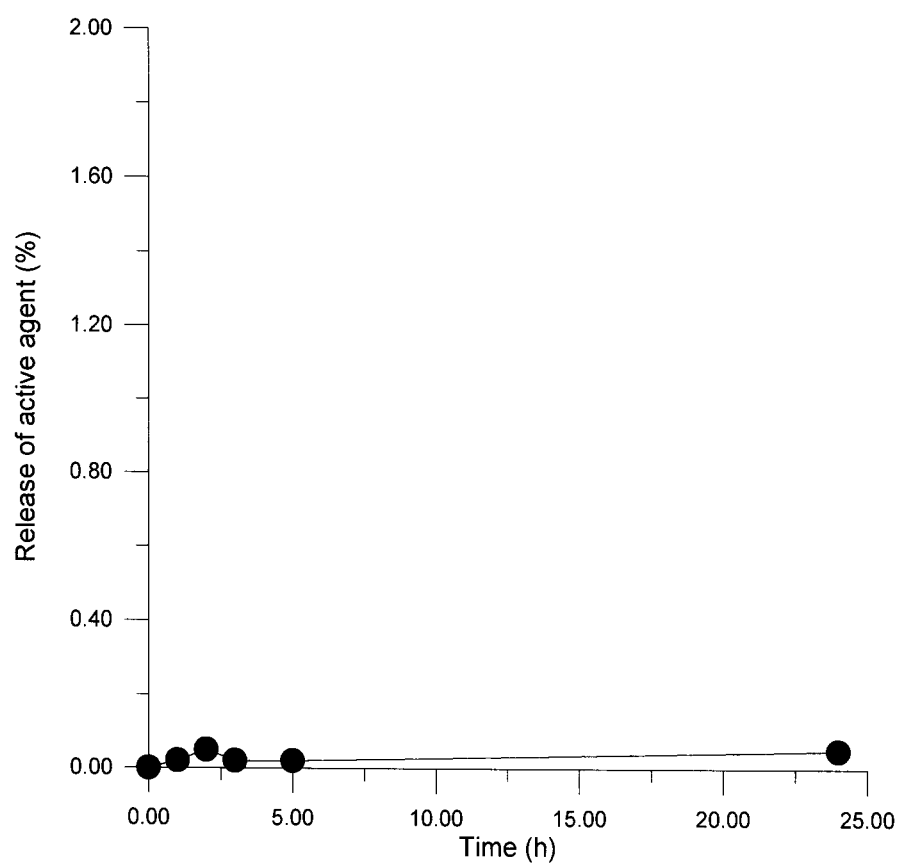
FIG. 2 is a graph of the data obtained from Example 8.

The insoluble chelating composition, 0.5 g, as prepared in example 5, was suspended in 50 ml of phosphate buffer (10 mM, pH 7.0) in a round bottom three-neck flask. The flask, open to the air, was rotated on a rotavapor in a water bath with the temperature held at 37° C. At various times, 3.0 ml of the supernatant fluid was removed to measure the absorbance of the supernatant at 282 nm. The release of the active agent (% of total active chelating agent initially bound) was calculated based on its extinction coefficient at 282 nm. The results shown in FIG. 2 indicate only very slight release of chelating group activity from the carried-chelator indicating the high degree of chemical stability of the carried-chelator composition. This chemical stability test was facilitated by the insoluble nature of the chelating composition, i.e., test for release of soluble chelating activity. It is to be noted that the soluble version of the chelating composition as from example 6 would be expected to also have a similarly high stability and not release its metal binding ligand as it differs only with respect to chain cross-linking, i.e., the polymer chains are of similar chemical composition as is the chemical linkage of the metal binding aspect to the remainder of the chelating monomer.

Example 9; Iron Chelating Kinetics of a Soluble Chelating Composition

Figure 3:
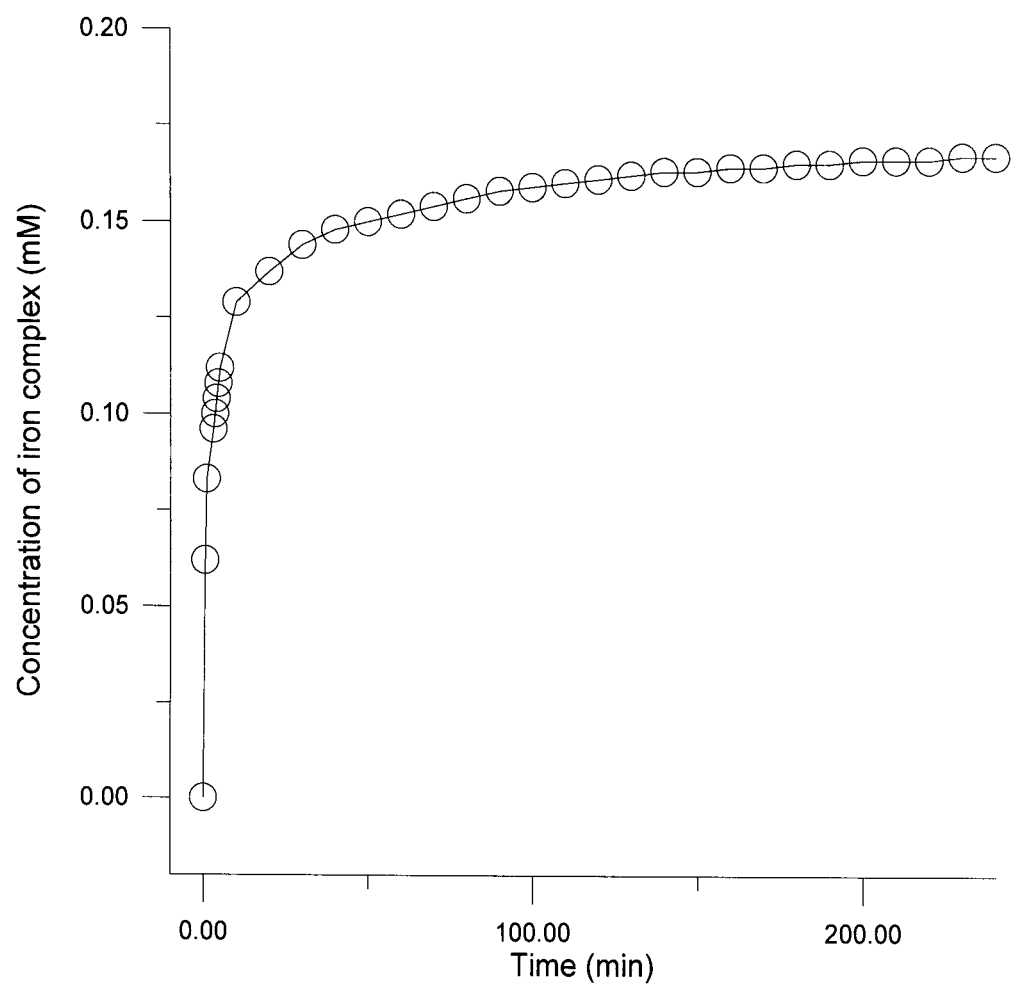
FIG. 3 is a graph of the data obtained from Example 9.

A sample of soluble chelating composition, as prepared in Example 6, consisting of 1.5 ml of a 0.116% (wt/vol) solution (in 10 mM phosphate buffer, pH 7.0) was mixed with 2.5 ml of 0.3 mM iron (III) citrate solution (dissolved in 10 mM phosphate buffer, pH 7.0) and stirred in a flask at 25° C. The absorbance of the solution at 456 nm was measured at various times following the initial mixing of the chelating composition with the iron solution. The increase in concentration of the iron-chelating composition complex over time was determined from the absorption of the reaction mixture at 456 nm with use of the extinction coefficient for the iron complex, so as to determine the concentration of iron bound. The results shown in the graph of FIG. 3 indicate a very rapid uptake of iron from citrate to the soluble chelating composition with Fe uptake nearly complete within a few minutes.

Figure 4:
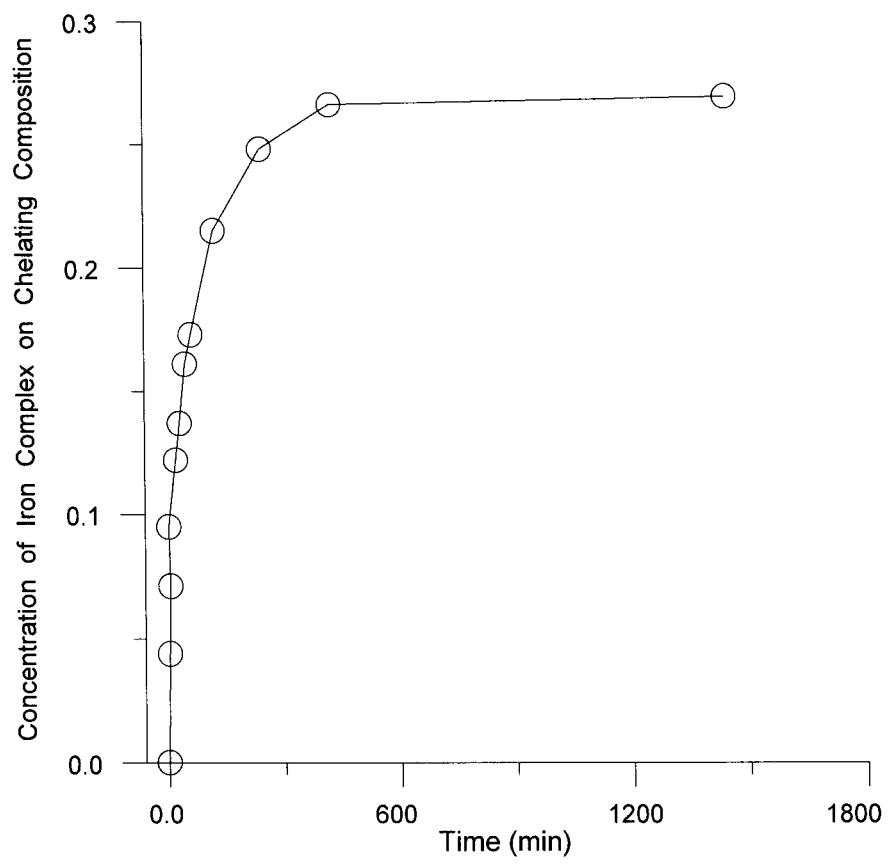
FIG. 4 is a graph of the data obtained from Example 10.

Example 10; Comparative Iron Chelating Kinetics of an Insoluble Chelating Composition This example, along with example 9, provides a comparison of metal binding for insoluble versus soluble chelating compositions. A 118.8 mg sample of insoluble chelating composition, as prepared in Example 5, was swollen in a three neck round bottom flask with 3.0 ml of water for 0.5 hours, and then 97 ml of 0.3 mM iron (III) citrate solution in phosphate buffer (10 mM, pH 7.0) was added. The flask was rotated open to the atmosphere on a rotavapor in a water bath at 25° C. At various times after adding the iron solution, 1.5 ml of the supernatant was removed without removal of the insoluble chelating composition solids so as to measure the iron concentration remaining in solution. The concentrations of the iron complex on the insoluble chelating composition over time were then calculated by difference. The results graphed in FIG. 4 show uptake of iron onto the insoluble chelating composition. By comparing relative rates of iron binding (i.e., example 9 vs. example 10) it can be appreciated that the soluble chelating composition binds iron much more rapidly than the insoluble chelating composition, i.e., approximately 80% Fe bound in less than 10 minutes for the soluble composition (from graph of data from example 9) vs 80% Fe bound by the insoluble version only after 3 hours shown in FIG. 4. This result illustrates an important unexpected advantage provided by the soluble chelating compositions of the present invention, i.e., a Fe binding rate much higher than that obtainable with insoluble chelating compositions.

Example 11; Iron Binding Strengths of Polymeric Chelating Compositions Versus Non-Polymeric Free Chelators Measurement of the Fe binding strengths can be measured and compared for different chelating materials. The overall Fe binding or association constants for iron binding of the free chelator, 1,2-dimethyl-3-hydroxy-pyridin-4-one (known as deferiprone), the soluble chelating composition possessing the functionally similar chelating group to deferiprone (prepared as in Example 6) and the insoluble chelating composition possessing the functionally similar chelating group to deferiprone (i.e., prepared as in Example 5) were determined for Fe (III) with results as shown in the table below. The association constant for another widely used free chelator ethylene-diamine-tetra-acetic acid or EDTA, typical of the chelators disclosed in U.S. Pat. No. 6,165,484, was also determined for comparison purposes.

| Chelator or Chelating Composition | Log $_{10}$ K$_{(assoc)}$ |
| --- | --- |
| EDTA, free chelator | 25 |
| Deferiprone, free chelator | 36 |
| Soluble chelating composition from Example 6 | 38 |
| Insoluble chelating composition from Example 5 | 38 |

These results show the high and improved binding strengths for iron of the chelating compositions of the present invention in comparison to free chelating groups, especially those disclosed in U.S. Pat. No. 6,165,484. The chelating compositions of the present invention showed a 100-fold increased iron binding efficiency over deferiprone. The superiority of the chelating compositions of the present invention as compared to the soluble free chelator EDTA can also be appreciated from these results.

Example 12; Stripping of Iron from Deferoxamine by Soluble Chelating Compositions 20 ml of soluble chelating composition prepared as in example 4, or soluble composition as prepared as in example 6, both with similar chelating capacity for Fe, and suspended in Phosphate Buffered Saline (PBS) at pH 7, were placed in separate dialysis bags and separately dialyzed against 20 ml of 2.0 mM deferoxamine (Desferal as obtained from Novartis Ltd.) containing 1.3 mM Fe (III) in PBS, for 24 hr at room temperature. Iron loss from the deferoxamine solution as external to the dialysis bags containing the chelating compositions was measured.

The soluble chelator as from example 4 was found to contain 71% of the total iron leaving only 29% bound by the deferoxamine B after the 12 hr incubation period.

The soluble chelator from example 6 was found to have removed 67% of the Fe from the deferoxamine by the end of the incubation period.

This example illustrates that soluble chelating compositions prepared on either polyvinylpyrolidone or polyacrylamide carrier materials had similar iron binding abilities and both soluble compositions were able to remove iron from the clinically used deferoxamine (Desferal) chelator, i.e., the strength of the soluble chelating compositions for Fe exceeded the binding strength provided by deferoxamine (Desferal).

Example 13; Antibacterial Activity of Soluble and Insoluble Chelating Compositions for *Staphylococcus aureus*

Figure 5:
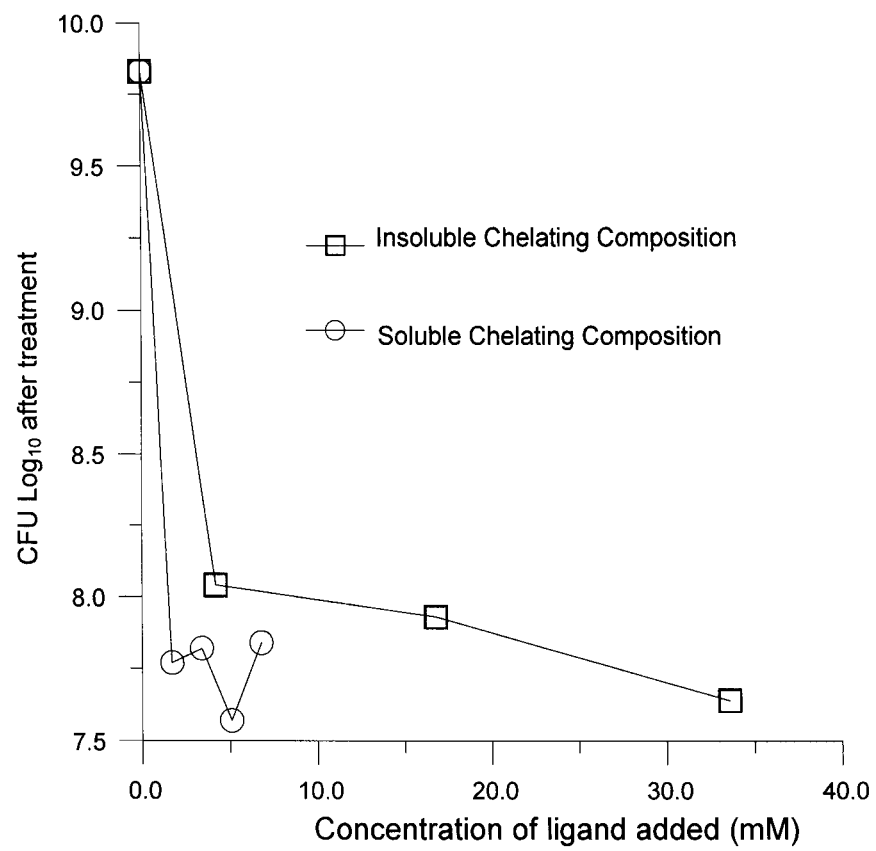
FIG. 5 is a graph of the data obtained from Example 13.

Soluble and insoluble chelating compositions, as prepared in examples 6 and example 5, respectively were tested in vitro for their abilities to suppress growth of *Staphylococcus aureus* strain Y67N. This strain was obtained and is available from the culture collection of Professor Warren Grubb, Curtin University, Perth Australia. Various amounts of the chelating compositions, as normalized for addition on the basis of the amount of iron binding capacity (metal binding ligand concentration equivalence) were added to samples of sterile trypticase soy broth medium contained in test tubes. An actively growing bacterial culture was used to inoculate the samples and these were then incubated for 24 hours at 37° C. Plate counts for bacterial colony forming units (CFU), a method which quantitates viable bacterial cells in a liquid sample, were then determined for each sample as shown in the graph of FIG. 5. The results show that addition of chelating compositions to the growth medium interfered with growth of the bacterial cells in a manner that showed dose-dependence for the amount of added chelating composition (expressed as amount of iron-binding chelator ligand added). The results also illustrate a higher and more pronounced activity for the soluble chelating composition vs. the insoluble composition, i.e., smaller amounts of Fe binding capacity added for the soluble chelating composition produced more killing of bacteria or inhibition of bacterial growth than for larger quantities of the analogous insoluble version of the chelating composition.

Example 14; Antibacterial Activity of Soluble Chelating Composition in Comparison to the Conventional Chelator Deferiprone for Clinical Isolates of *Staphylococcus aureus*

Clinical isolates of *Staphylococcus aureus* as obtained from human infections were obtained and are obtainable from the culture collection of Warren Grubb, Curtin University, Perth, Australia. It should be noted that the clinical isolates as obtained from patients at the Royal Perth Hospital in Perth Australia can be expected to have strong similarities to other clinical isolates of this bacterium as obtained elsewhere in the world as the genetic determinants of antibiotic resistance characteristics in *Staphylococcus aureus* are now generally understood. Thus, similar results to those shown in examples 14-17 can be expected with other clinical isolates as obtained elsewhere and having similar antibiotic resistance patterns to those tested for these examples.

A total of 9 clinical strains were tested for their sensitivities to either deferiprone or the soluble chelating composition prepared as in Example 6 as follows: Strains WBG525, WBG8860, WBG248, WBG8701, WBG7913X1876, WBG4530 and WBG541 for sensitivity to deferiprone and Strains WBG525, WBG8860, WBG4330 and WBG1320 for sensitivity to the soluble chelating composition prepared as in Example 6. Thus, for this series of tests a total of seven strains were tested for their sensitivities to deferiprone and four strains were tested for their sensitivities to the soluble chelating composition. Two of the strains, WBG525 and WBG8860 were tested for their sensitivities to both deferiprone and the soluble chelating composition. Four to six individual bacterial colonies of each strain as obtained from their growth on blood agar were harvested into Mueller-Hinton broth (MHB) and incubated at 37° C. until they reached an optical density equal to or exceeding a 0.5 McFarland standard. The culture was diluted with MHB to equal 0.5 McFarland standard. Dilutions ($10^{-1}$) of these standards were used for test inocula. It should be appreciated that growing the bacterial strains on blood agar and then in MHB ensured the bacterial inoculum was not restricted for iron prior to the test but rather the bacterial cells were ensured to possess an ample endogenous iron supply. MHB media also is known to exceed the iron requirements of test microorganisms and supplies ample available Fe in the external environment of growing cells.

Figure 6:
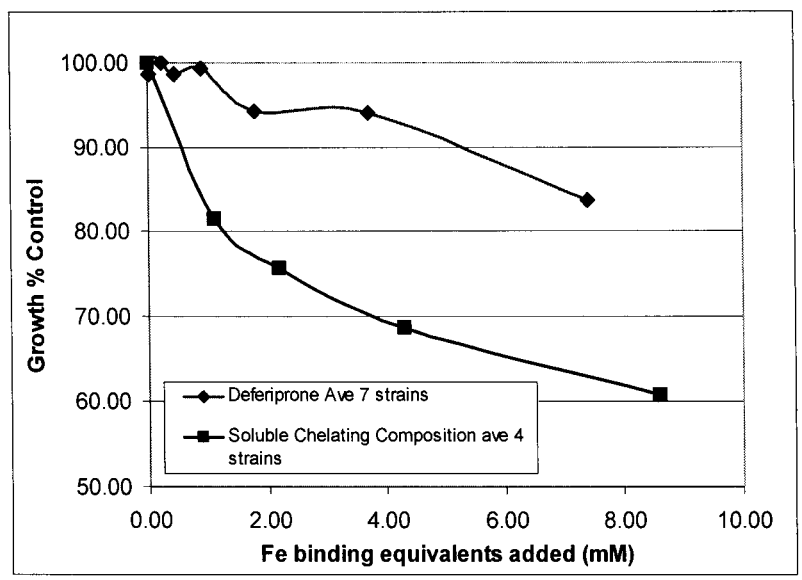
FIG. 6 is a graph of the data obtained from Example 14.

A range of dilutions of the deferiprone or soluble chelating composition was prepared in MHB in test tubes so as to provide a range of added iron chelating capacity as measured in Fe binding equivalents. The final volume per test tube was 500 µl. Bacterial inoculum, 25 µl of the $10^{-1}$ dilutions of the appropriate *S. aureus* strain was added to each tube. The tubes were incubated at an angle on a reciprocating shaker at 37° C. overnight and the growth results were scored as a percentage of growth based on measured turbidity at a wavelength of 600 nm with a spectrophotometer of the test sample, as compared to a control samples that had received no added deferiprone or soluble chelating composition. The results are shown in the graph of FIG. 6. Deferiprone showed only modest inhibition of growth and even when added at a high concentration of over 7 mM Fe binding equivalents it resulted in only about 15% inhibition of growth. In comparison, the soluble chelating composition resulted in significant inhibition of growth at much lower concentration with only 2 mM Fe binding equivalents added resulting in about 25% inhibition of growth. These results demonstrate that Fe binding provided by 3-hydroxy-pyridin(4)one are relatively ineffective when provided on the low molecular weight deferiprone (<700 Daltons) but much more effective when present on the soluble chelating composition in terms of inhibiting growth of clinical *Staphylococcus aureus* strains. The soluble chelating composition tested for this example had a molecular weight of between 80,000 Daltons and 300,000 Daltons. This soluble chelating composition would be too large in molecular weight to be taken up into the cells of these bacterial strains while deferiprone would be expected to be taken up by the cells.

Example 15; Soluble Chelating Composition Increases the Sensitivity of Clinical Isolates of *Staphylococcus aureus* to the Anti-Cellular Agent Streptomycin More Effectively than Either the Related Insoluble Composition or the Related Free Chelating Molecule The antibiotic sensitivity tests for this example and also for Examples 16 and 17 were carried out according to a NCCLS (now Clinical and Laboratory Standards Institute) method for Minimum Inhibitory Concentration (MIC) determination of antibiotic sensitivity with a slight modification. Sensitive or antibiotic resistant strains of *Staphylococcus aureus* (*S. aureus*) were grown on blood agar plates overnight at 37° C. Four to six individual colonies of each strain were harvested into Mueller-Hinton broth (MHB) and incubated at 37° C. until they reached an optical density equal to or exceeding a 0.5 McFarland standard. The culture was diluted with MHB to equal 0.5 McFarland standard. Dilutions ($10^{-1}$) of these standards were used for inocula. Various stains of antibiotic resistant *Staphylococcus aureus* were used for these tests as shown in the results below. It should be appreciated that growing the bacterial strains on blood agar and then in MHB ensured the inoculum was not restricted for iron prior to the test but rather the bacterial cells were with ample endogenous iron supply.

A range of two-fold dilutions of a test antibiotic was prepared in MHB. The final desired concentrations ranged from 2.5 to 1280 µg/ml. Soluble and insoluble chelating compositions, as prepared in Example 6 or Example 5, or the free iron chelating agent deferiprone were added to the antibiotic containing tubes at known concentrations of iron binding capacity (referred to as iron binding equivalents) to allow direct comparison of the different compositions or free chelator. The final volume per tube was 500 µl. Bacterial inoculum, 25 µl of the $10^{-1}$ dilutions of the appropriate *S. aureus* strain was added to each tube. The tubes were incubated at an angle on a reciprocating shaker at 37° C. overnight and results were scored as growth based on turbidity or no growth (lack of turbidity). The Minimum Inhibitory Concentration (MIC) for the antibiotic was determined from the growth results.

Comparative testing of the sensitivities of strain WBG525, as obtained from the culture collection of Warren Grubb, Curtin University, Perth, Australia, to streptomycin in the presence of the soluble free clinical chelator deferiprone, the insoluble chelating composition (prepared as in Example 5) and the soluble chelating composition (prepared as in Example 6) produced the results shown in the table below.

| Chelator or Chelating Composition Added | Chelating Capacity Added in Fe binding equivalents mM | MIC Streptomycin µg/ml |
|---|---|---|
| None (Control) | 0 | >640 |
| Deferiprone | 7.4 | >640* |
| Insoluble Chelating Composition as from Example 5 | 4.3 | 640 |
| Soluble Chelating Composition as from Example 6 | 2.2 | 160 |

*slight growth <5% of control turbidity at 640 µg/ml observed

These results show the high degree of resistance of this clinical strain to streptomycin as seen in the control test, i.e., a concentration of 640 µg/ml streptomycin was not sufficient to reach the MIC concentration. The clinically utilized chelator deferiprone was not useful for increasing the sensitivity of the bacteria to streptomycin even when supplied at 7.4 mM Fe binding equivalents, i.e., growth was slightly reduced but the MIC was not reached. The binding capacity of 7.4 mM added as deferiprone represents the amount of chelating capacity needed to bind 7.4 mM Fe or approximately 0.4 mg Fe/ml of medium. MHB is known to contain iron at approximately 0.3 µg/ml or a concentration of approximately 5 µM. Tests at higher concentrations (not shown in the table) showed that deferiprone even at 15 mM Fe binding equivalents still allowed slight growth of the bacterial cells when tested at a concentration of 640 µg/ml streptomycin. The insoluble chelating composition prepared as in Example 5 at a concentration of 4.3 mM Fe binding equivalents was also not effective in increasing the sensitivity of the bacteria to streptomycin. Tests at higher concentrations for the insoluble chelating composition (not shown in table of results) did show that an addition of 8.6 mM Fe binding equivalents lowered the MIC to 320 µg/ml, thus showing it was more effective than the free chelator deferiprone. Addition of the soluble chelating composition provided a dramatic increase in the sensitivity of the bacteria to streptomycin. An addition of only 2.2 mM Fe binding equivalents of the soluble chelating composition lowered the MIC for streptomycin to just 160 µg/ml. These results show the unexpected and dramatic improvements provided by the soluble chelating compositions of the present invention in relation to increasing the sensitivity of a bacterial pathogenic cell to an anti-cellular agent.

Example 16; Soluble Chelating Composition Increases the Sensitivity of Clinically Isolated *Staphylococcus aureus* to Various Anti-Cellular Antibiotic Agents A series of tests was set up as in Example 15 with various antibiotic anti-cellular agents. The clinically isolated strains were obtained from the culture collection of Warren Grubb, Curtin University, Perth, Australia. The effects of adding soluble chelating polymer, prepared as in Example 6, at two concentrations of added Fe binding equivalents on the MIC values for various antibiotics in comparison to MIC values with no added soluble chelating composition were examined with results as shown in the table below.

| | | | MIC (100% inhibition) µg/ml antibiotic | |
|---|---|---|---|---|
| Antibiotic Tested | Bacterial Strain Tested | No Chelator Added (control) | Soluble Chelating Composition mM Fe binding equivalents added | |
| | | | 1.1 mM | 2.2 mM |
| Kanamycin | WBG525 | 320 | 20 | 20 |
| Streptomycin | WBG525 | >640 | 640* | 160* |
| Gentamcin | WBG1320 | 320* | 40* | 20* |
| Neomycin | WBG4340 | 1280 | 160 | 80 |
| Tetracycline | WBG4340 | 40 | 20 | 10 |
| Ciprofloxacin | WBG8860 | 20 | 10 | 10 |

*slight growth <5% of control growth observed

These results show that the soluble chelating composition increased the sensitivities of various clinically isolated antibiotic resistant *Staphylococcus aureus* strains to various antibiotic anti-cellular agents. As well, the addition of the soluble chelating composition displayed increased effectiveness at a higher added concentration, i.e., the effect was dose dependent.

These above results show the potential for increasing the effectiveness of a range of conventionally used antibiotics for various bacteria, including highly resistant pathogenic *Staphylococcus aureus* by including chelating compositions with the antibiotics.

It should also be appreciated that this type of test is relatively crude and insensitive, as results are scores, based solely on macroscopic growth or no growth in a series of tubes each containing 100% more or less of the antibiotic agent than its neighboring tubes in the dilution series. The pre-growth of the strains on blood agar would also provide conservative results as such growth conditions would ensure the bacterial cells tested were fully satisfied for iron prior to testing. In a clinical context within a vertebrate animal host it is likely that bacteria would be in an iron-limiting environment when encountering an antibiotic, a situation that could dramatically increase the effect of supply of carried-chelator composition. It would be expected that a similar series of tests conducted with bacteria that were grown under iron-limiting or minimal iron sufficiency conditions, e.g., on chemically defined medium with controlled iron content vs. growth on blood agar that is rich in iron or in MHB that contains excess iron, would demonstrate further enhanced sensitivity of the bacterial strains to the synergistic effects of chelating composition with antibiotic. This aspect is very significant as it is now widely known that iron is available at only very low concentrations to microorganisms when these are growing in an animal host such as a human. On this basis, the positive influence of increasing the susceptibility of a clinical infection causing microorganism to an anti-cellular agent such as an antibiotic might be expected to be more pronounced in vivo.

Example 17; Iron Neutralization of the Enhancing Effects of a Soluble Chelating Composition with Respect to the Sensitivity of *Staphylococcus aureus* to Antibiotic Anti-Cellular Agents A series of antibiotic sensitivity tests was set up as in example 16 utilizing the soluble chelating compositions as prepared in Example 6. Separate test series with different clinically isolated *Staphylococcus aureus* strains, as obtained from the culture collection of Warren Grubb, Curtin University, Perth, Australia, and various antibiotics were employed but for each series a control test comprising addition of iron sufficient to supply two times the chelating capacity of the supplied chelating composition was also included. The results provided below, show that the soluble chelating composition lowers the antibiotic resistance of the bacteria to penicillin, tetracycline and ciprofloxacin for antibiotic resistant *Staphylococcus aureus* and that the enhancing effects of the chelating compositions were related to iron, as iron addition with the soluble chelating composition negated the enhancing effects of chelating compositions.

a) Strain WBG8701 with Penicillin:
  The MIC for this strain with penicillin was 640 µg/ml indicating its very high resistance to penicillin. Addition of 4.4 mM Fe binding equivalents of a soluble chelating composition, prepared as in example 6, lowered the MIC to 320 µg/ml. However, the iron-loaded chelating composition did not lower the MIC.

b) Strain WBG8516×541 with Tetracycline:

The MIC for tetracycline of this strain was 160 µg/ml and the MIC was lowered to 80 µg/ml through addition of the soluble chelating compositions similar as for (a). Addition of iron-saturated chelating composition resulted in an MIC of 160 µg/ml demonstrating that the enhancement by the chelating compositions was related to the iron binding ability of the soluble chelating composition.

It should be noted again as for Examples 15 and 16 that this type of test is relatively insensitive, as the obtained results are scores, based solely on macroscopic growth or no growth in a series of tubes each containing two-fold differences in antibiotic concentrations from one tube to the next in the test series. As well the standard MIC protocol requires scoring of the lowest concentration resulting in no growth. In these tests partially reduced growth was observed at concentrations below the reported MIC. This aspect could have important implications as partial inhibitions at even lower concentrations of both antibiotic and chelating composition could have practical clinical significance. Also the pre-growth of these bacterial strains on blood agar would also provide conservative results as such growth conditions would ensure the bacterial cells tested were fully satisfied for iron prior to testing and would have entered the test with iron reserves. In a clinical context within a vertebrate host it is more likely that bacteria would be in an iron-limiting environment when encountering an antibiotic, a situation that could dramatically increase the enhancing effects of chelating composition. It would be expected that a similar series of tests conducted with bacterial cells that were grown under iron-limiting or minimal iron sufficiency conditions, e.g., on chemically defined medium with controlled iron content instead of blood agar and MHB, would demonstrate further enhanced sensitivity of the bacterial strains as provided by the chelating compositions.

Example 18; Inhibition of Growth of *Candida albicans* by a Soluble Chelating Composition

*Candida albicans* is a fungal yeast pathogen capable of causing disease in humans. This yeast was tested for its growth in low and high iron containing cultivation media in the laboratory and for the effects of the addition of various concentrations of the soluble chelating composition prepared as in Example 4. A chemically defined medium as suitable for aerobic growth but made without addition of inorganic iron components was used so as to provide a fully defined medium with only its residual iron content, i.e., as contributed by contaminant iron present in the other medium components. This medium, GPP, is described elsewhere (Dumitru, R., J. M. Hornby, and K. W. Nickerson. 2004). This medium was then contacted with 2 g/liter of a sample of insoluble chelating, prepared as in example 5, during shaking at room temperature for 4 hours, followed by filtration to separate the insoluble chelating composition from the extracted medium. This procedure provided a basal medium with partially removed Fe, i.e., to a low residual concentration. The extracted medium was measured for its iron content and was found to contain <0.08 µM Fe. This extracted medium represented the low iron condition for growth and this was compared to extracted medium but with Fe re-added to achieve either 0.5 µM Fe or 5.0 µM Fe. The source of the yeast strain tested was the American Type Culture Collection, strain ATCC 10231. The extents of growth in various samples of the three media both without and with various concentrations of the soluble chelator (range of concentrations tested was 0.02 to 1 mg/ml) were followed using spectrophotometric readings for optical density (OD) at a wavelength of 600 nm, at various times during incubation of the samples at 30° C., following their inoculation with actively growing cells of *Candida albicans*.

The results in the Table below show that the soluble chelating composition inhibited growth of the yeast for over three weeks when the initial Fe content of the growth medium was low. At high Fe levels in the growth medium, inhibition by the soluble chelator was reduced. These results demonstrate the inhibition of the growth of pathogenic yeast by reducing and restricting the supply of Fe available for growth of the yeast.

| Iron Test Condition | MIC Soluble Chelating Composition (mg/ml) Measured at: | | | | |
|---|---|---|---|---|---|
| | 2 d | 4 d | 10 d | 14 d | 21 d |
| <0.08 µM Fe | <0.02 | <0.02 | 0.03 | 0.50 | 0.5 |
| 0.5 µM Fe | 0.03 | 0.03 | 0.25 | 1.0 | >1 |
| 5.0 µM Fe | 0.25 | 0.25 | >1 | >1 | >1 |

Example 19; Soluble Chelating Composition Increases the Sensitivity of *Candida albicans* to the Anti-Cellular Agent Fluconazole

*Candida albicans* ATCC 10231, yeast cells, as grown in defined medium with no additional added Fe as in example 18, were tested in the same media for their sensitivities to fluconazole, an anti-cellular agent as proto-typical of the azole class of antibiotics that are commonly used to control fungal growth and pathogenesis in humans and with fluconazole plus the soluble chelating composition, as prepared in Example 4. Fluconazole as a typical member of the azole class of anti-fungal antibiotics that function by inhibiting sterol synthesis.

The standard NCCLS MIC procedure as utilized in Example 15 was utilized and MIC concentrations providing 80% growth inhibition were determined after different lengths of contact (4 days, 10 days, and 42 days) with the agents. The results, shown in the table below, demonstrate that the yeast was much more susceptible to fluconazole when in the presence of the soluble chelator, the soluble chelator provided a dose-dependent improvement to the sensitivity to the fluconazole and, the soluble chelator enhancing effect was due to its Fe binding activity, as a sample of the Fe-saturated soluble chelator did not alter fluconazole sensitivity. It is important to note that only a low amount of the soluble chelating composition was added for these tests and this low amount of soluble chelator addition alone did not markedly affect growth of the yeast, i.e., when no antibiotic was added. This example demonstrates the enhancement of the anti-cellular activity of a conventional anti-fungal antibiotic (fluconazole) with one of the soluble chelating compositions as disclosed in this invention.

| Agent | Fluconazole MIC µg/ml | | |
|---|---|---|---|
| | 4 d | 10 d | 42 d |
| Fluconazole alone | >6.0 | >6.0 | >6.0 |
| Fluconazole plus 12.5 µg/ml soluble chelator | <0.05 | 0.05 | 0.19 |
| Fluconazole plus 25 µg/ml Soluble chelator | <0.05 | <0.05 | <0.05 |
| Fluconazole plus Fe-saturated soluble chelator | >6.0 | >6.0 | >6.0 |

These results show that the addition of even a small amount of a soluble chelating composition increases the sensitivity of the yeast to the anti-cellular agent fluconazole and that the affect of the chelating composition is directly related to its iron binding activity, i.e., addition of Fe with the soluble chelating composition negated its enhancement affect. These results also show the difference between controlling growth and controlling an activity of a cell. The small amount of soluble chelating composition chosen for this test was insufficient on its own to cause inhibition of growth, yet it was sufficient to affect the yeast activity of resisting the action of the anti-cellular agent fluconazole.

Figure 7:
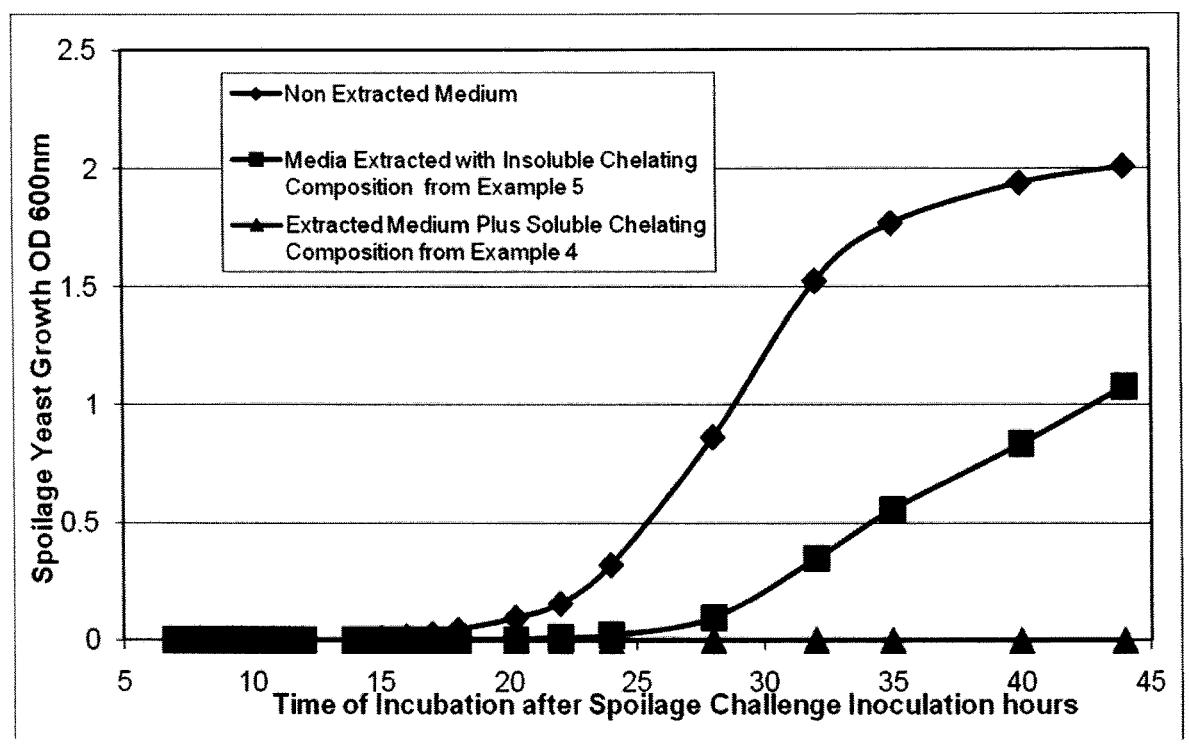
FIG. 7 is a graph of the data obtained from Example 20.

Example 20; Demonstration of Microbial Preservation of a Product Through First Removing Excess Iron from an Aqueous Product Followed by Chelation of the Remaining Portion of Fe with a Soluble Chelating Composition A spoilage test to assess the ability of iron extraction by an insoluble chelating composition in conjunction with addition of a soluble chelating composition to an aqueous medium that is highly susceptible to growth of spoilage microorganisms was set up as follows. GPP medium as used for Example 18 containing 0.5 uM Fe was inoculated with Candida vini, a spoilage yeast obtained as American Type Culture Collection strain ATCC 20217, to represent the untreated control. As can be seen in the graph of FIG. 7 the spoilage yeast grew quickly in the control non extracted medium. A sample of GPP medium was also extracted with the insoluble chelating composition prepared as in Example 5. A 5 g sample of insoluble chelating composition was hydrated in deionized water, washed two times in deionized water on a Buchner filtration apparatus and harvested onto filter paper (VWR Corporation). A one liter sample of GPP complete medium was batch-contacted with the washed insoluble chelating composition in a flask with shaking at 200 rpm (reciprocating shaker) at 20° C. for 2 hr to achieve partial removal of its contained iron. The extracted medium was recovered by removal of the insoluble chelating composition onto filter paper and the extracted medium was filter-sterilized (0.22 µm Millipore Corporation) and used for challenge tests by inoculation with Candida vini as had been performed for the non-extracted medium. The residual Fe concentration in the extracted medium as determined by atomic absorption spectrophotometry was <4 ppb.

The results obtained with extracted medium show that the insoluble chelating composition was highly efficient for removing Fe from the GPP, lowering the Fe content from 0.5 µM (28 ppb) to <0.08 µM (4 ppb), the lower detection limit for the measurement equipment utilized for this test. The results showed that removal of Fe to this low level provided some preservation of the medium, in that growth of the yeast was delayed by around 10 hours and the extent of growth was substantially less than had been obtained with the control non extracted medium. However, it can be seen that some growth did eventually occur and thus preservation was improved but not complete in the extracted medium. Note, that no other chemical preservation agents had been added to these tests with any preservation observed being solely attributable to removal of iron. Addition of the soluble chelating composition as prepared in Example 4 at a concentration of 0.25 mg/ml to the medium that had been first extracted with the insoluble composition, completely prevented growth of the spoilage Candida vini yeast. Separate tests showed that lower concentrations of the soluble chelating composition were also effective in providing this high degree of preservation and that addition of Fe to saturate the soluble chelating composition allowed the spoilage yeast to grow, thereby reversing the preservation that had been achieved. These results indicate that the soluble chelating composition is capable of binding Fe in a form not accessible by the spoilage yeast Candida vini as the chelating composition and the low amount of iron remained present in the treated medium yet the yeast could not grow unless the soluble chelating composition was saturated for its iron binding capacity. This example shows the ability to achieve preservation from microbial spoilage by first extracting the majority of the iron from the aqueous medium with an insoluble chelating composition and then adding a soluble chelating composition to render the remaining iron in the medium non-accessible to spoilage microorganisms.

The slower and reduced growth seen with Fe removal indicated the yeast cells were deprived for iron. On this basis and given other supporting results in the various other examples provided, it should be appreciated that such preservation treatment in relation to removing or making Fe less available to microbial cells would be expected to increase the susceptibility of the spoilage yeast and other microorganisms to any added chemical preservation agents, i.e., the combination of lessened availability of iron would increase the efficacy of action of other chemical preservative agents.

Example 21; Demonstration of the Preservation of a Product Through Addition of a Soluble Chelating Composition in Conjunction with a Conventionally Used Preservation Agent Candida albicans ATCC 10231, yeast cells, as grown in defined medium as for Example 18 with no additional added iron (i.e., the only but adequate Fe available for the yeast was contributed from being present along with the other added medium components) was tested for its sensitivities to preservative agents in a challenge test series of tests where Minimum Inhibitory Concentrations (MIC) were determined for potassium sorbate and methyl paraben (two widely used chemical preservative agents) in tests with the preservative agents alone and in other tests where either 12.5 or 25 µg/ml soluble chelating composition prepared as in Example 4 was included with the preservative agents. MIC values (achieving 80% inhibition of growth) for the various tests were determined following 2 days and 10 days of challenge incubation at 30° C. with results as shown in the table below. These results demonstrate the substantially lowered MICs for these preservative agents (reduced by 4-10×), i.e., greatly increased potency of the preservative agents) when utilized in the presence of one of the soluble chelating composition of this invention. Additional tests using added Fe, with Fe addition sufficient so as to satisfy (saturate) the Fe chelating activity of the soluble chelating composition, demonstrated the enhanced preservative agent activity in the presence of the soluble chelating composition was directly attributable to the Fe chelating activity of the soluble chelating composition.

| Preservative Agent | Sorbate or Paraben MIC mg/ml | |
|---|---|---|
| | 2 days | 10 days |
| Sorbate alone | 0.12 | 0.25 |
| Sorbate plus soluble chelating composition 12.5 µg/ml | <0.02 | <0.02 |
| Sorbate plus soluble chelating composition 25 µg/ml | <0.02 | 0.03 |
| Paraben alone | 0.50 | 1.0 |
| Paraben plus soluble chelating composition 12.5 µg/ml | <0.02 | 0.25 |
| Paraben plus soluble chelating composition 25 µg/ml | <0.02 | 0.25 |

Example 22; Demonstration of the Importance of Molecular Weight of a Soluble Chelating Composition in Relation to Restricting Iron to Microbes and Interfering with Microbial Growth

Figure 8:
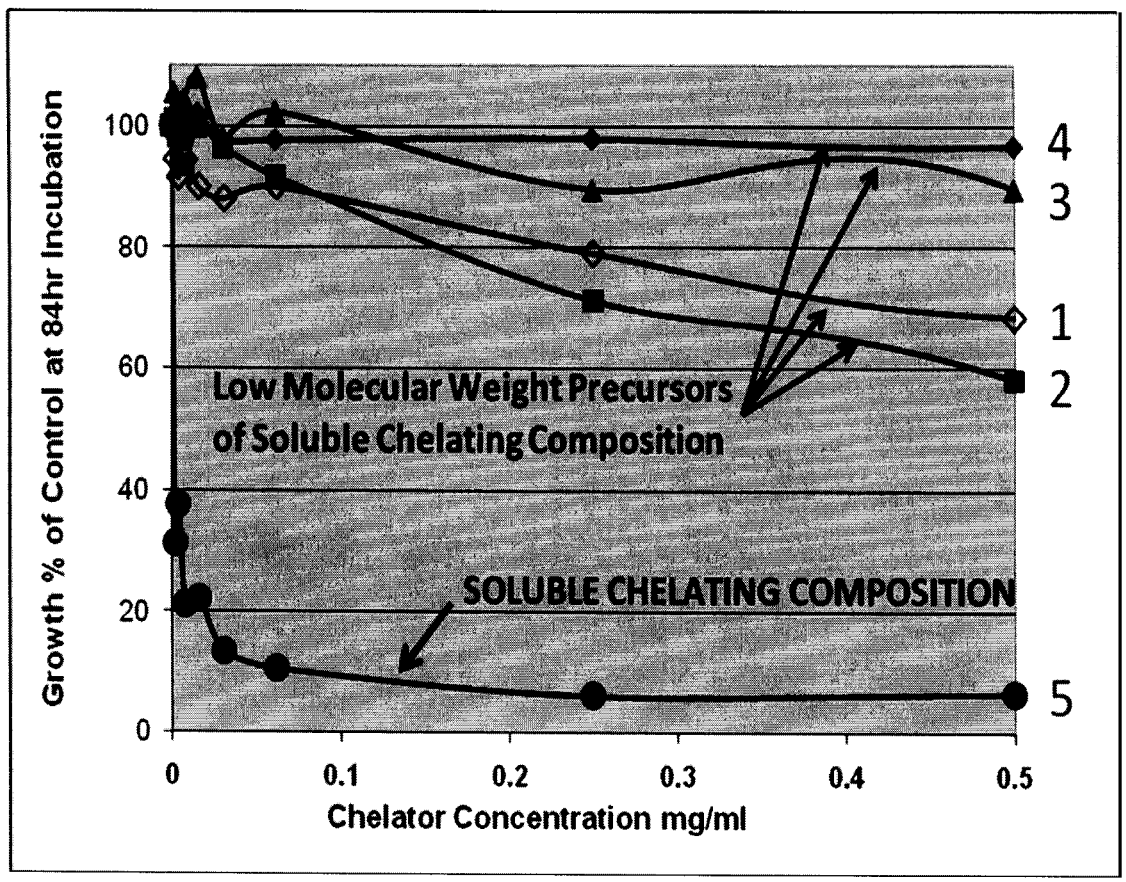
FIG. 8 is a graph of the data obtained from Example 21.

*Candida albicans* ATCC 10231 was tested for its sensitivities to: the medical chelator deferiprone (#1 in the graph of FIG. 8) (a product of Apotex Pharmaceuticals); the precursor chemicals used for the preparation of soluble chelating compositions of the present invention, including 3-hydroxy-2-methyl-4-pyrone (#2 in the graph of FIG. 8), AHMP as from Example 1 (#3 in the graph of FIG. 8) and MAHMP as from Example 2 (#4 in the graph of FIG. 8) and also the soluble chelating composition as from Example 4 (#5 in the graph of FIG. 8). The yeast was grown in defined medium as for Example 18 with no additional added iron (i.e., the only but adequate Fe available for the yeast was contributed from being present along with the other added medium components). Growth of the yeast in the defined media with added test chelating materials was compared to control samples that had not received any of the chelating materials following 84 hours of incubation and growth at 30° C. The results in the graphs of FIG. 8 show that a group of chelating chemicals and the corresponding soluble chelating composition all which possess hydroxypyridinone metal coordinating aspects differ as to their abilities to restrict iron to the yeast. Specifically, chemicals #1, #2, #3 and #4 did not substantially restrict growth and each of these are of a molecular size below 1500 Daltons, i.e., a molecular size sufficiently low so that these molecules can be internalized by the yeast cells. These chelators being internalized by the yeast were incapable of restricting iron supply to the yeast cells. In contrast, the soluble chelating composition as of Example 4 which had been synthesized from these same chelating chemical precursors, i.e., specifically from precursors #2, #3 and #4, inhibited growth of the yeast even at a low concentration and this soluble chelating composition was of a molecular size greater than 10,000 Daltons. Thus, low molecular weight chelators such as deferiprone and similar compounds permitted growth while the soluble chelating composition that contained functional groups similar to deferiprone but was a molecular weight higher than 1500 Daltons restricted growth, eventhough the various compounds tested were each capable of binding iron through their pyridinone functionality.

Therefore, these results demonstrate the importance and utility of having a soluble chelating composition of a molecular size large enough so that it cannot be readily internalized by the microbial cells or accessed for its iron at the external surface of the cell by way of receptors for iron carrying molecules and, such that the soluble chelating composition binds iron and retains this iron in the external environment of the yeast cell from where the iron is not as readily available to the cells, these cells requiring the iron inside their cells for use by the cell.

Figure 9:
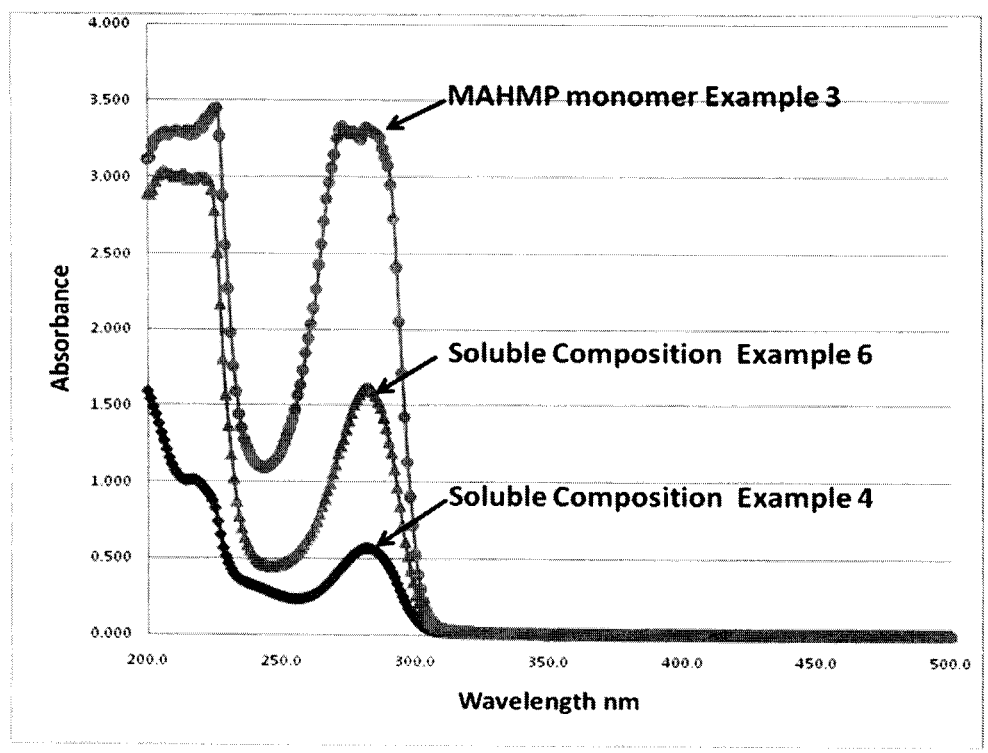
FIGS. 9 and 10 are graphs of data obtained from Example 22.

Example 22; Demonstration of Incorporation of Active Fe-Binding Monomer MAHMP into Co-Polymer Soluble Chelating Compositions Absorption spectra for the monomer MAHMP prepared as in Example 3, the soluble chelating composition prepared as in Example 4 and the soluble chelating composition prepared as in Example 6 were compared as to their absorption spectra between 200 and 500 nm as shown in the graph of FIG. 9. Samples were dissolved in water and scanned with the reference cell containing water. The results demonstrate that MAHMP absorbs in the ultra-violet range with maximum at around 275 nm and had little absorption above 300 nm. Absorption similar to MAHMP was also detected within the chelating composition polymers in the case of co-polymers made with either pyrrolidone (i.e., as in Example 4) or acrylamide (i.e., as in Example 6).

Figure 10:
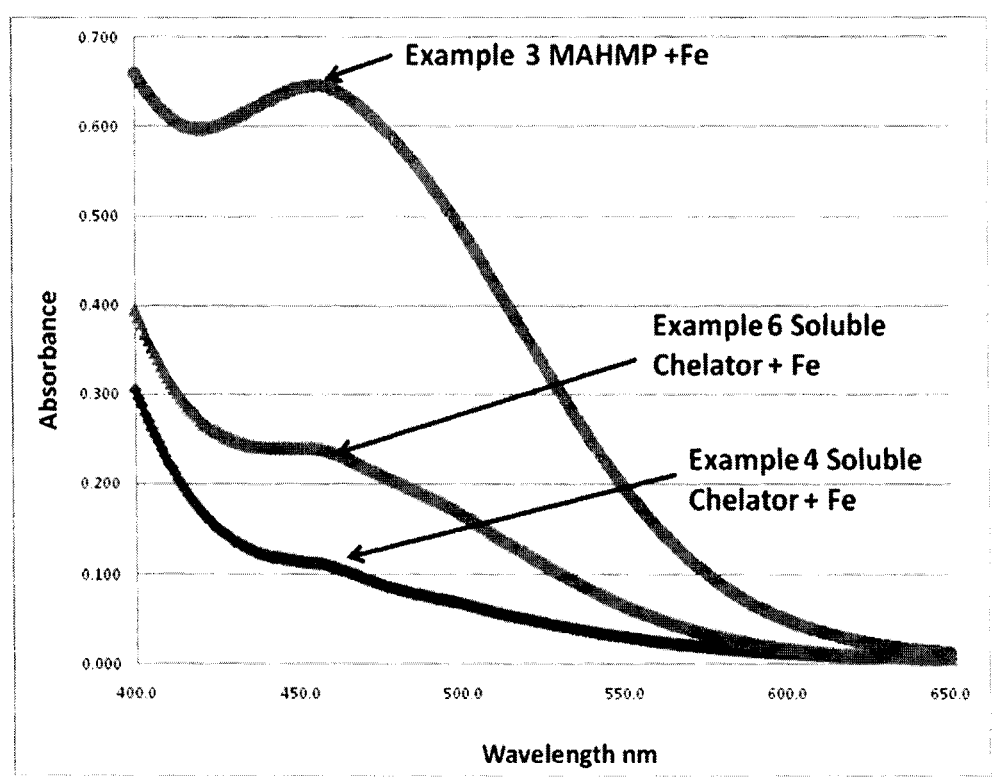

The iron binding activity of the chelating pyridinone active grouping within the soluble chelating compositions was demonstrated by reacting samples dissolved in water with iron as shown in the graph of FIG. 10 of absorption between 400-650 nm. Iron addition to MAHMP produced a red chromophore with absorption maximum at around 460 nm and a similar chromophore was also observed in the soluble chelating compositions made as co-polymers of MAHMP with either vinyl-pyrrolidone (soluble chelating composition as from Example 4) and dimethyl-acrylamide (soluble chelating composition Example 6), i.e., after they were reacted with iron.

Example 23; Demonstration of the Molecular Weight Aspect of a Soluble Chelating Composition A sample of soluble cheating composition was prepared as in Example 4 except that the synthesis was carried out using twice the amounts and volumes as were described in Example 4. One half of the volume of the freshly prepared sample was dialyzed in a dialysis tube with a molecular weight cut-off of 8,000 Daltons (Da), twice (24 hours for each step) against of 4 liters of fresh deionized water. The soluble chelating composition within the dialysis tube was then harvested and a dry sample for testing was obtained by freeze-drying. The other half volume of the freshly prepared soluble chelating composition was not dialyzed but it was size fractionated as to molecular weight of the soluble chelating composition molecules by passage through a successive series of ultrafiltration membranes each of different molecular weight exclusion sizes and with an additional one liter of water being used at each filtration stage to wash through the majority of molecules that would pass through each of the specific ultrafilter sizes and with nitrogen gas pressure to assist the filtration. The following separate fractions were obtained representing materials of the following molecular weight size ranges: >100 kDa; 10 kDa- 100 kDa and 1 kDa-10 kDa (kDa=1000 Da). Each of these separate fractions were harvested and freeze dried to yield dry samples for testing.

The relative percentage weight yields of each size fraction were determined as a function of the combined weight of the three size fractions as shown in the table below:

| Soluble Chelator Molecular Weight | Yield % |
| --- | --- |
| >100 kDa | 3.3 |
| 10 kDa-100 kDa | 38.4 |
| 1 kDa-10 kDa | 58.3 |

These yield results demonstrated the majority of the soluble chelating composition for this example preparation was of a molecular size greater than 1 kDa and up to 100 kDa with little of this particular sample being greater than 100 kDa.

The absorption spectra of each of the above size fractions, as well as the sample as prepared by direct dialysis, i.e. >8 kDa size soluble chelator, and also a reference sample of MAHMP, i.e., the chelating monomer precursor as prepared in Example 3, were compared after their reactions with iron as described for Example 22. These results are shown in the graphs of FIG. 11 (where kDa=kD).

Figure 11:
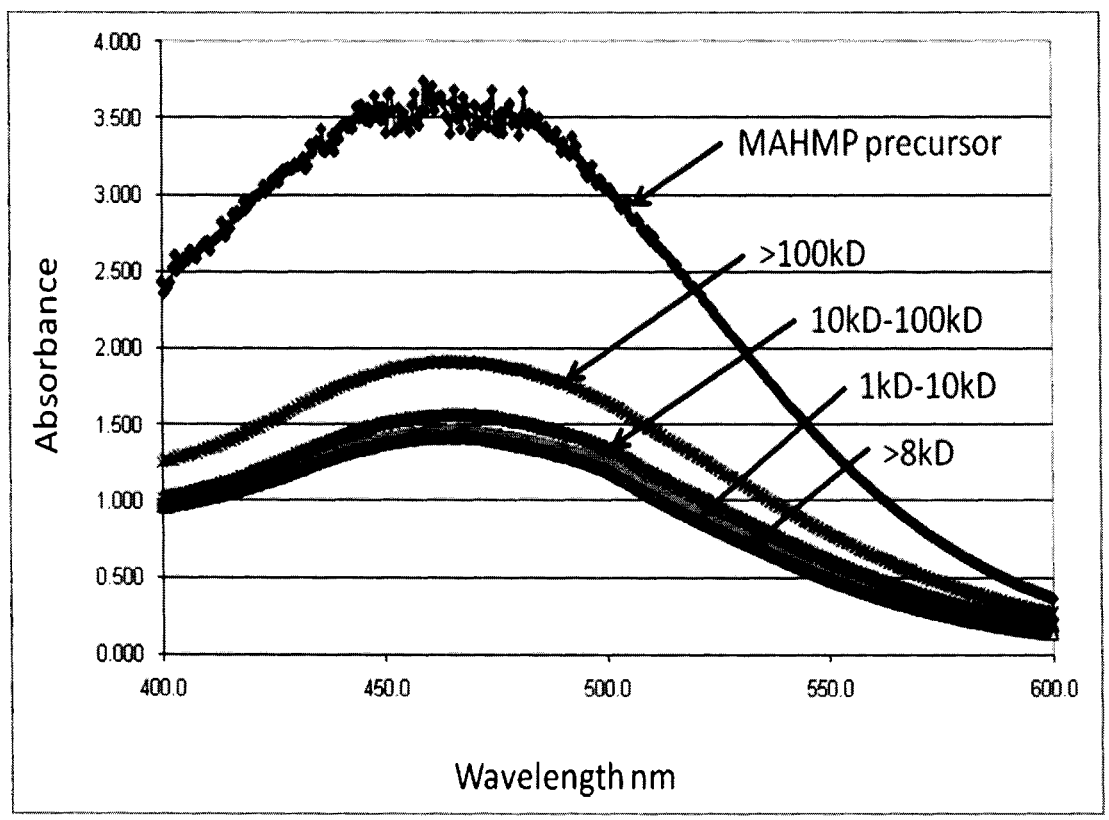
FIG. 11 is a graph of data obtained from Example 23.

The absorption spectra in the graphs of FIG. 11 demonstrate a generally similar chemical composition of these various molecular size fractions, i.e., as to relative amounts of their contents of the iron-binding chelating group within the co-polymers. The chelating monomer group MAHMP alone and this group when within the soluble chelating composition exhibited a chromophore when iron was bound to it, with an absorption maximum at around 460 nm.

Figure 12:
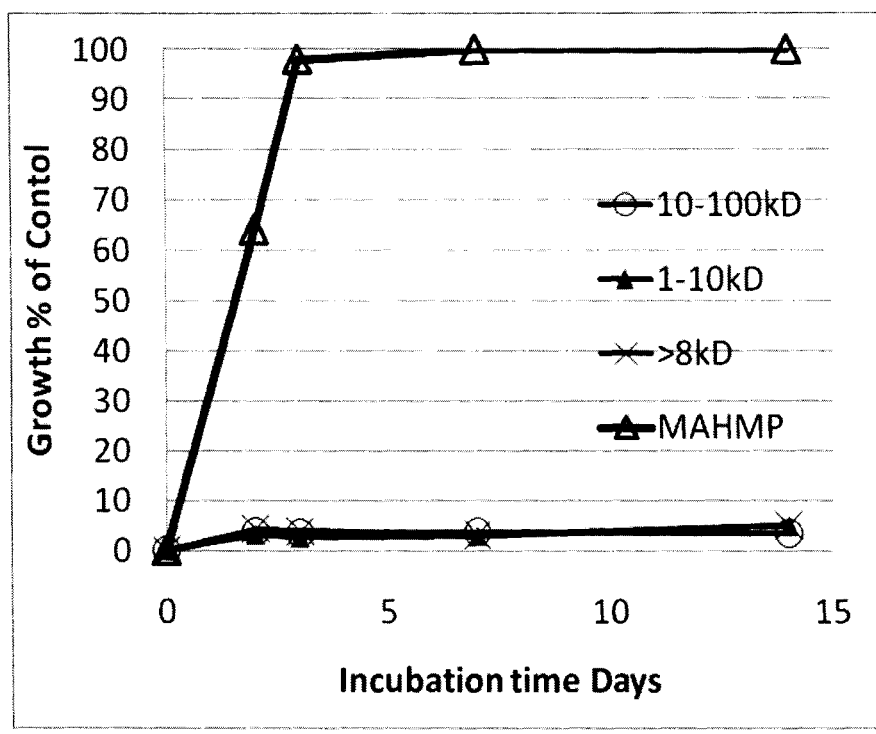
FIG. 12 is a graph of data obtained from Example 23.

Results of testing as to the relative anti-microbial inhibitory activities of these various fractions with each tested at a concentration of 0.25 mg/ml against the yeast *Candia albicans* and with testing similar to that described in Example 22 are shown in the graphs of FIG. 12. The >100 kDa fraction represented insufficient recovered material for this anti-microbial testing and therefore this was not tested. These results show similar activities of the soluble chelating composition when in a size of >1 kDa and up to a size of 100 kDa. All three molecular size fractions of the soluble chelating composition provided strong anti-microbial activity with less than 5% of control growth occurring even after an incubation period of 14 days. The MAHMP of a molecular size of <500 Da and being the precursor monomer to the soluble chelating compositions was found to readily support growth of this yeast as had also been shown with the results of Example 21.

This example therefore demonstrates that low molecular weight soluble chelators such as the MAHMP precursor as used to prepare the soluble chelating compositions of the present invention, I.e., low molecular weight chelators of a size less than approximately 1500 Da and specifically this MAHMP example of a size <500 Da are not anti-microbial in that they support growth of *Candida albicans*. The soluble chelating composition of the present invention with a molecular size of approximately >1000 Da was inhibitory for this yeast.

While the lower size limit of the soluble chelating composition tested was nominally 1000 Da, i.e., given the stated lower exclusion limit of the ultrafiltration membrane utilized, it is most likely that the predominance of the actual filtered soluble chelator fraction as obtained with this filter was of molecular weight size substantially greater than 1500 Da, i.e., a normal distribution of polymer molecular sizes with average molecular weight well above 1500 Da would be expected. MAHMP has a molecular weight of approximately 236 Da and vinylpyrrolidone has a molecular weight of approximately 111 Da. A soluble chelating composition as made from these two monomer groups would have a molecular weight above 1500 Da with a copolymer of both monomers or a homopolymer of the MAHMP monomer comprised of only approximately 4 monomer units of each material.

Example 24; Demonstration of the Anti-Microbial Activity of Iodine as Combined with the Fe Chelating Activity of a Soluble Chelating Composition Containing Pyrrolidone and/or Polypyrrolidone in its Chemical Structure

*Candida albicans* ATCC 10231, yeast cells, as grown in defined medium as for Example 18 with no additional added iron (i.e., the only but adequate Fe available for the yeast was contributed from being present along with the other added medium components) were inoculated into fresh media with added iron at either 0.5 µM or 5.0 µM and tested for their sensitivities to the soluble chelating composition as from Example 4 and with this chelating composition further treated with iodine as follows:

A sample of the soluble chelating composition prepared as in Example 4 was dissolved in water at 20 mg/ml and iodine solution (KI in water) was added to achieve a potential loading of 10% (w/w) iodine onto the composition. After addition of the iodine, the solution of soluble chelator/iodine was dialyzed (8,000 MW cut-off dialysis tubing) for 12 hours against deionized water and then the dialyzed composition was harvested and its anti-microbial activity was compared to a sample of the soluble chelating composition that had not been treated with iodine. Dialysis was performed for this example to ensure the substantial portion of the iodine available was not free iodine in solution but rather was residual iodine bound to aspects of the soluble chelating composition. Samples were compared for their anti-microbial activity with yeasts grown in low added Fe (Graph A in FIG. 13) and high added Fe (Graph B in FIG. 13).

Figure 13:
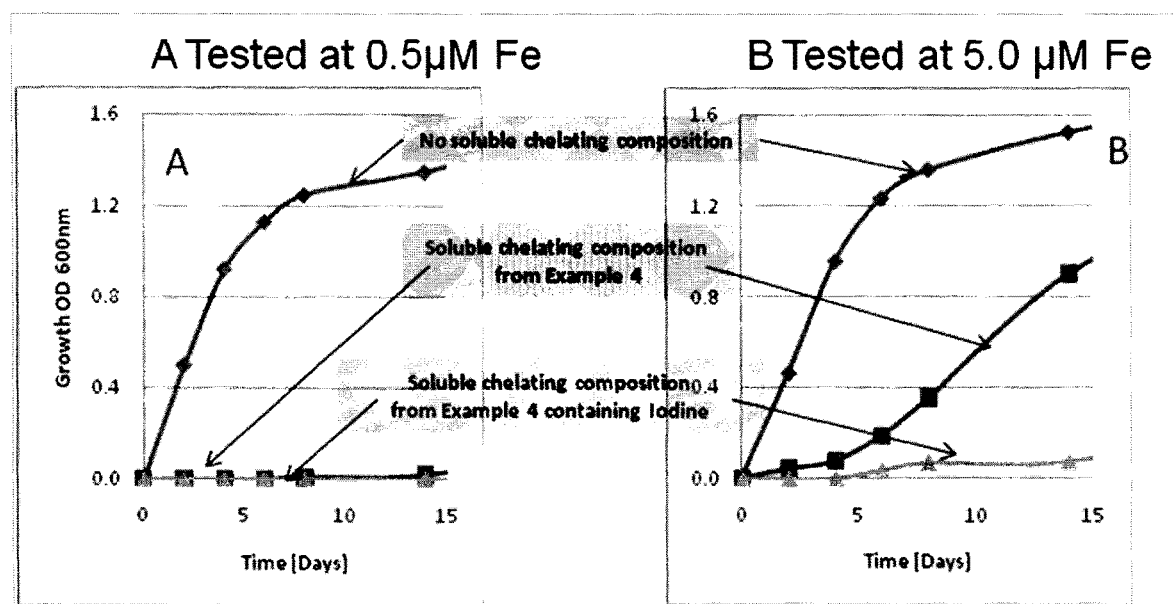
FIG. 13 are graphs of data obtained from Example 24.

The results in graphs A and B of FIG. 13 show that under low Fe conditions both the soluble chelator and the soluble chelator with bound iodine were anti-microbial in comparison to the untreated control (no added chelating composition). With high added Fe, i.e., sufficient added Fe to overcome the Fe chelating anti-microbial activity of the soluble chelating composition, the soluble chelating composition without added iodine was less active due to the presence of excess Fe but the soluble chelating composition containing iodine still retained its anti-microbial activity. This comparison demonstrates the separate anti-microbial activity of iodine as bound to the soluble chelating composition. Therefore the soluble chelating composition containing iodine had two modes of anti-microbial activity; one related to its iron sequestration activity preventing yeast growth and one related to iodine anti-fungal action on the yeast, iodine having a known anti-microbial and non-metal related action on its own.

Example 25; Blood Compatibility of Soluble Chelating Composition

These tests were performed using standard clinical laboratory procedures. Three separate samples of soluble chelating composition, prepared as in example 4, were added to human plasma samples at a concentration of 0.25 mg/ml. Prothrombin times and Partial Thromboplastin times were measured in a clinical hematology laboratory in comparison to control plasma samples using the established clinical testing procedures. All three soluble chelating composition samples and the control plasma produced Prothrombin times of 1.2 (International Normalized Ratio; INR), while Partial Thromboplastin Time was prolonged slightly by the soluble chelating composition (ave. 51.8 vs. 32.9 PTT). The soluble chelating composition was observed to have no affect on platelet aggregation. These results indicate that the soluble chelating composition has potential for blood compatibility and therefore use for systemic administration to human and other animal hosts.

Example 26; Synthesis and Characterization of AHMP and MAHMP

Figure 14:
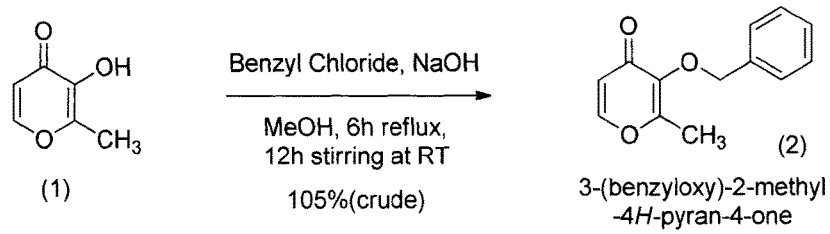
FIG. 14 is a summary of the chemical synthesis procedures for Example 26.
Figure 14:
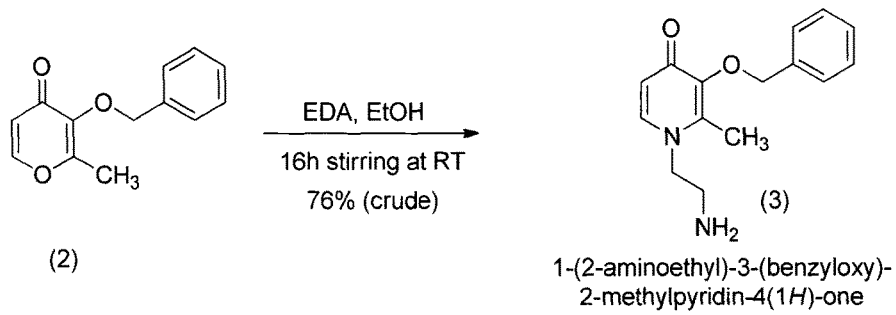
Figure 14:
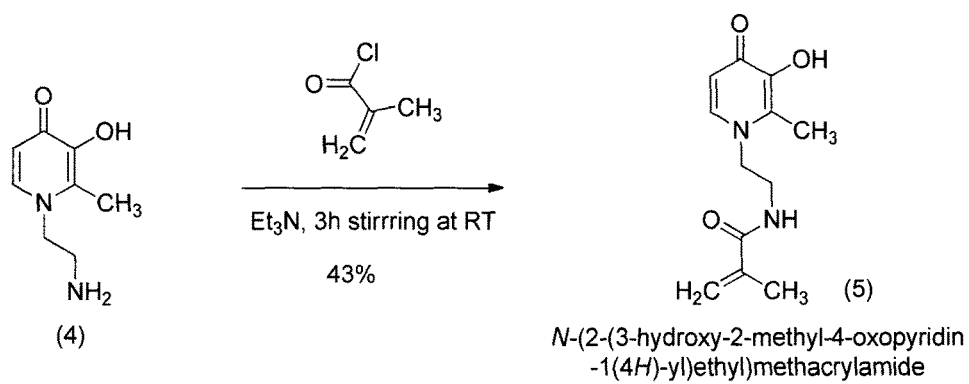

AHMP and MAHMP were synthesized according to the procedures detailed in Examples 1 and 3, respectively, but with slight modifications as to increasing yields and purity as detailed below. The overall synthesis scheme can be seen in FIG. 14

A Synthesis of 3-(benzyloxy)-2-methyl-4H-pyran-4-one

To a 20 L, 4 necked flask at room temperature was charged 3-hydroxy-2-methyl-4-pyrone (1 Kg, 7.93 mole, 1 eq) followed by methanol (10.2 L, 10.2 Vol.). Benzyl chloride (1.36 L, 11.9 mole, 1.5 eq) was then charged drop wise using an addition funnel. This was followed by the addition of a solution of sodium hydroxide (333.3 g, 8.33 mole, 1.05 eq dissolved in 1.12 L water) to give a pale yellow clear solution. The solution was refluxed for 6 h at 75-80° C. and then stirred overnight at RT. Reaction progress was monitored by TLC. Generally the reaction was complete after overnight stirring.

Once the reaction was complete, the solvent was evaporated under vacuum and the resulting yellowish orange oil was mixed with 4.5 L water and extracted with methylene chloride (DCM) (3×2.5 L). The DCM extracts were combined and washed with 5% NaOH solution (3×1.2 L) and water (3×1.2 L) respectively. The combined NaOH washings were again extracted with DCM (1.5 L). Organic fractions were combined, dried over sodium sulphate and concentrated to give yellowish orange oil.

Yield: 1.8 Kg (105% crude).

B Synthesis of 1-(2-aminoethyl)-3-benzyloxy-2-methyl-4(1H)-pyridinone 3-(benzyloxy)-2-methyl-4H-pyran-4-one (1.3 Kg, 6.01 mole, 1 eq, crude material from the previous step) was charged to a 20 L, 4 necked flask and then ethanol (8.5 L, 6.5 Vol.) was added to give a clear solution. Ethylenediamine (1.8 L, 27.95 mole, 4.65 eq) and water (34 mL, 0.03 Vol.) were then introduced. The solution was stirred overnight at RT. Reaction progress was monitored by TLC. Generally the reaction was complete after overnight stirring After the reaction was complete, the solvent and excess ethylenediamine were removed under vacuum at 65° C. to yield yellowish brown oil. The resulting oil was mixed with water (7 L) and extracted with DCM (3×3 L). The organic fractions were combined and concentrated to give yellowish brown oil.

Note: Final mixing with water prior to extraction with DCM gave a solid during small scale synthesis. When this protocol was followed on large scale, material did not solidify and was thus extracted with DCM and concentrated.

Yield: 1.175 Kg (76% crude).

Figure 15:
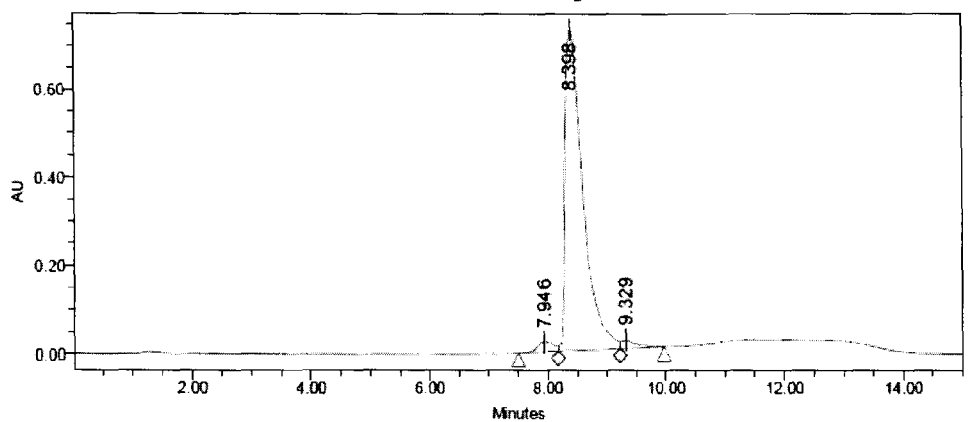
FIG. 15 is a graph of data obtained for Example 26B.

The High Pressure Liquid Chromatographic analytical results shown in FIG. 15 indicated the AHMP to have a purity of >95%.

C Synthesis of 3-Hydroxy-1-(β-methacrylamido-ethyl)-2-methyl-4(1H)-pyridinone (MAHMP)

To a 2 L flask was charged, AHMP (100 g, 0.488 mole, 1 eq) followed by water (413 mL, 4.13 Vol.) to give a clear solution. Thereafter, triethylamine (204 mL, 1.46 mole, 3 eq) and acetonitrile (826 mL, 8.26 Vol.) were added and the resulting solution was placed on ice bath and stirred at 0° C. Methacryloylchloride (47.46 mL, 0.488 mole, 1 eq) was then added drop wise using dropping funnel over 1.5 h to the reaction mixture kept at 0-5° C. The reaction mass was then brought to RT and stirred for 3 h. The reaction progress was monitored by Thin Layer Chromatography (TLC).

After the completion of reaction (3 h), solvents were removed under vacuum to yield a yellow solid. This solid was then washed with hot acetone (2 L) and filtered. Once filtration was complete, additional solids separated out from the initially clear filtrate. Thus the material was filtered once again. The filtrate was then evaporated to remove approximately 800 mL of the acetone and kept in refrigerator for 18 h at 0-5° C. after which solids that were formed were recovered by filtration to yield a light yellow solid (76 g). This was then stirred with acetone (190 mL) for 4 h and filtered to yield MAHMP (50 g) as an off-white solid.

Note: After the entire process above was carried out, NMR analyses sometimes showed the presence of triethylamine hydrochloride as an impurity in some batches. This was removed by slurrying in chloroform (2.5V, 3 h) followed by filtration.

Yield: 50 g (43.4%).

Figure 16:
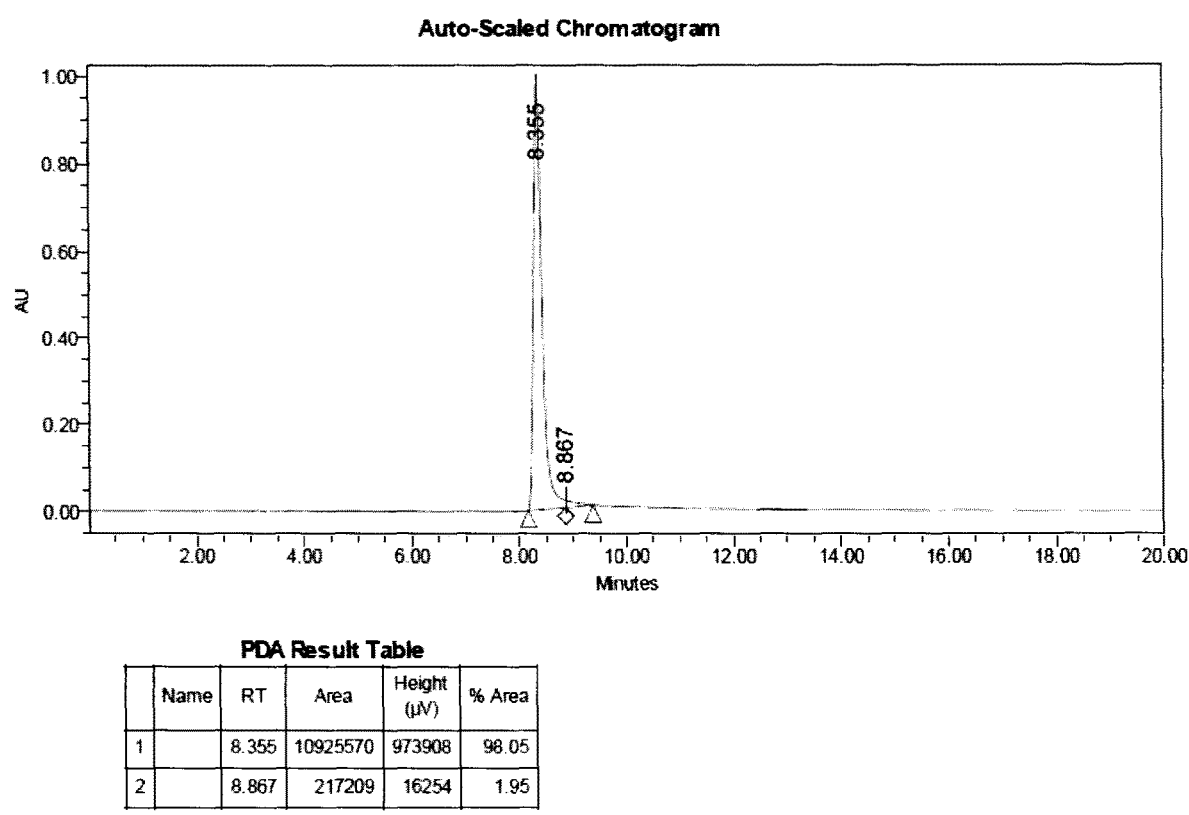
FIG. 16 is a graph of data obtained for Example 26C.

The High Pressure Liquid Chromatographic analytical results shown in FIG. 16 indicated the MAHMP to have a purity of >98%.

Figure 17:
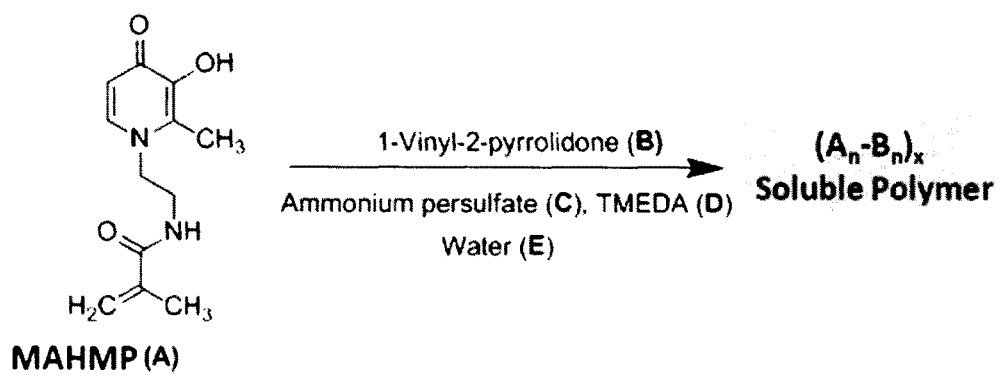
FIG. 17 is a summary of the chemical synthesis procedures for Example 27.

Example 27; Synthesis Optimization of a Soluble Chelating Composition Comprising an Active Pyridinone Chelating Agent Co-Polymerized in a Soluble Linear Polyvinylpyrolidone Polymeric Carrier The synthesis conditions for a soluble polymer chelating composition as described in Example 4 were examined by varying proportions of polymerization reactant concentrations and amounts of polymerization reactants while holding the amounts of the metal-chelating monomer MAHMP constant as shown in FIG. 17 and described in the table below. Thin Layer Chromatography (TLC) using MAHMP as reference standard was used to examine for any unreated MAHMP in the product fractions as obtained in each test.

| | | Reaction Conditions | | | | | |
|---|---|---|---|---|---|---|---|
| Test No | A (eq) | B (eq) | C (eq) | D (vol) | E (vol) | Dialysis (hrs) | Remarks/Result |
| 1 | 1 | 21.6 | 0.1 | 0.17 | 85 | 48 | Procedure as described in Example 4 Result: Unreacted MAHMP detected |
| 2 | 1 | 21.6 | 0.1 | 0.17 | 42 | 48 | Increased reactants conc. 2X Result: Unreacted MAHMP detected |
| 3 | 1 | 21.6 | 0.1 | 0.17 | 27 | 48 | Increased reactants conc. 4X Result: Unreacted MAHMP detected |
| 4 | 1 | 21.6 | 0.1 | 0.17 | 85 | 72 | Extending dialysis duration. Result: Unreacted MAHMP detected |
| 5 | 1 | 30 | 0.2 | 0.34 | 85 | 48 | Altered reagent equivalents Result: No unreacted MAHMP detected |

The above test results indicated it was possible to adjust reactant amounts so as to more fully utilize the bulk of the available MAHMP, i.e., through incorporating this into a soluble polymer product. Failure to detect unreacted MAHMP in the product samples by TLC indicated low amounts of unreacted MAHMP.

Example 28; Comparison of Molecular Weight Distributions of Soluble Chelating Compositions Comprising an Active Pyridinone Chelating Agent Co-Polymerized in a Soluble Linear Polyvinylpyrolidone Polymeric Carrier Samples of approximately 6 mg of soluble polymer material dissolved in de-ionized water were separately chromatographed by upward flow using de-ionized water through a 2.5 cm×48 cm packed column of Sepharose CL-6B (Aldrich Chemical Company) and fractions of approximately 4.5 ml each were collected during elution of a sample with approximately 300 ml of water. The individual fractions were measured as to contents of 280 nm absorbing material and for absorption at 450 nm after addition of 0.01 ml of 0.18M $FeSO_4$/0.54M sodium citrate solution (added to detect iron binding activity attributable to MAHMP content in the materials in the fractions. The following samples were compared: the soluble polymer prepared as in Example 4 with dialysis being carrying out with a membrane of nominal size exclusion of approximately 8 kDa; the soluble polymer as obtained after lyophilization of a portion of the sample prepared as in Example 27 test 5 and a sample as prepared by azeotropic water removal using toluene of a portion of the sample as obtained in Example 27 test 5 both with dialysis having been being carried out with a membrane of nominal size exclusion of approximately 8 kDaa. The Sepharose CL-6B column was separately calibrated using three different linear dextran standards (Sigma/Aldrich) of average molecular weights of 2 MD 71 kDa and 12 kDa with detection of these in column fractions using the phenol-sulphuric acid method for detection of carbohydrate and also with a sample of MAHMP prepared as in Example 26.

Figure 18:
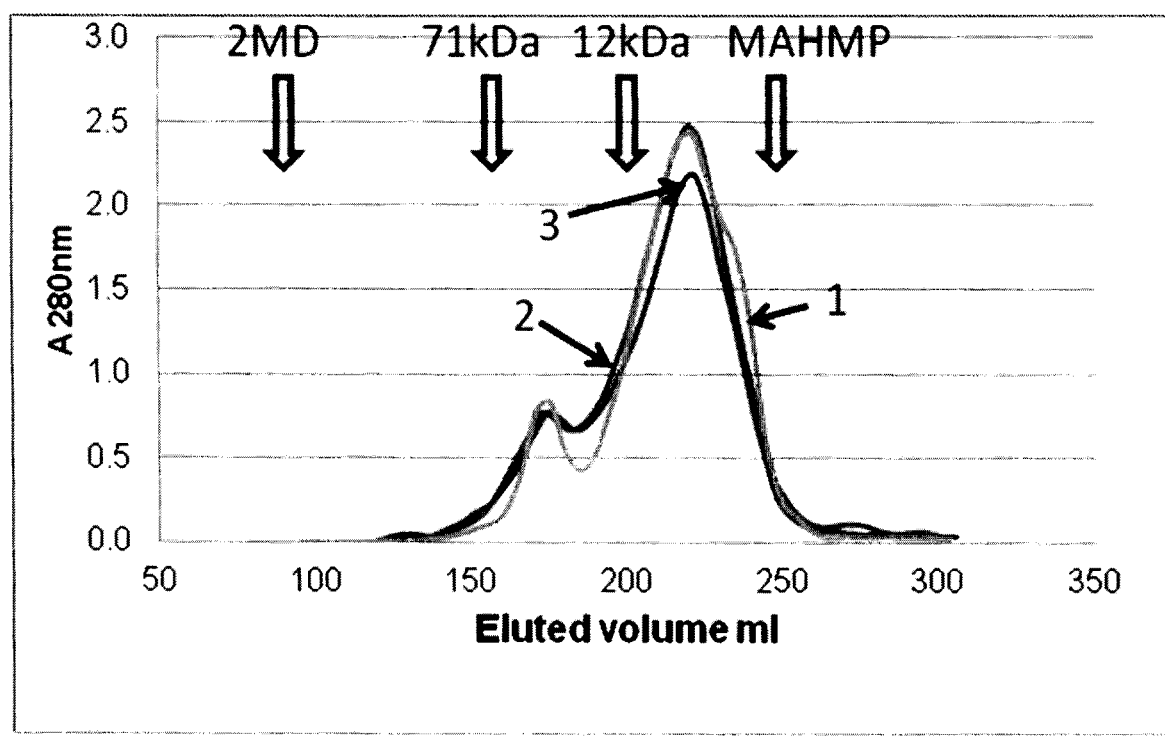
FIG. 18 is a graph of the data as obtained in Example 28.

The elution profiles of the soluble polymer samples and the relative molecular weights as determined by comparison to known dextran samples and MAHMP are shown in FIG. 18. Sample 1 was that as obtained by the procedure in Example 4 with dialysis being carrying out with a membrane of nominal size exclusion of approximately 8 kDa. Sample 2 was that obtained in Example 27 test 5 by lyophilization and sample 3 was that obtained by azeotropic drying in Example 27 test 5.

These results show that the soluble polymers as obtained were of a similar molecular size distribution with the bulk of the material in each of a molecular size (weight) of between 8 kDa and 71 kDa. There was no material in any of these samples of a size ≥2 MD (the approximate exclusion limit of the Sepharose column where materials of this size or greater would not separate but rather elute in the column void volume). Molecular weight analysis of samples by aqueous size separation chromatography versus X-ray diffraction as was used for materials in Example 4 indicated somewhat lower molecular weights. The latter are expected to be more accurate being determined for hydrated polymers in solution. The lower limit of molecular size is difficult to determine precisely but given that dialysis was carried out with membranes of nominal size exclusion characteristic of 8 kDa it can be concluded that the bulk of the soluble polymer materials obtained would be larger than a molecular weight of 1500 Da.

Figure 19:
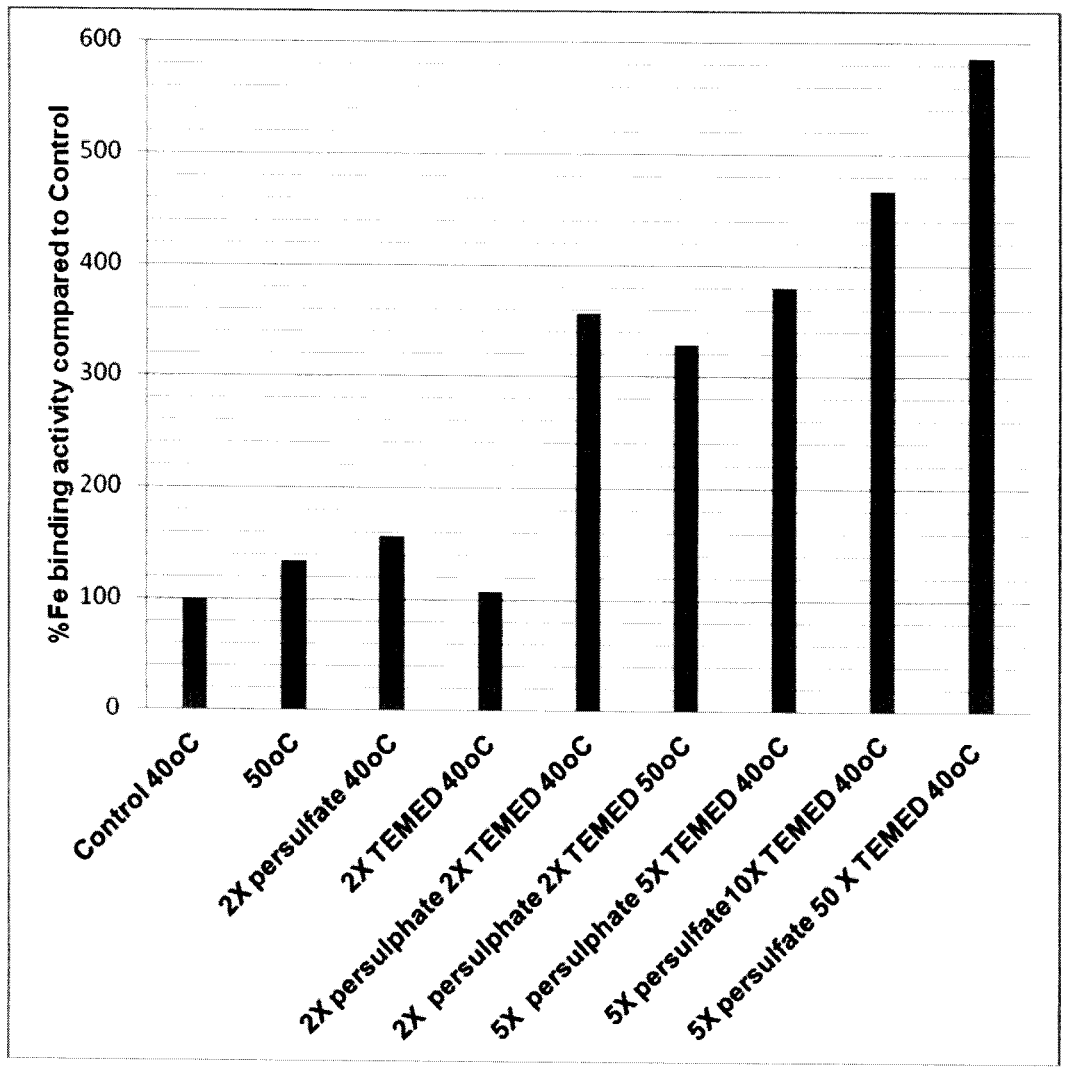
FIG. 19 is a graph of the data as obtained in Example 29.

Example 29; Synthesis Conditions Optimization for Soluble Chelating Compositions Comprising an Active Pyridinone Chelating Agent Co-Polymerized in a Soluble Linear Polyvinylpyrolidone Polymeric Carrier A sample of soluble polymer was prepared as described in Example 4 and the raw polymerized fraction was separated as follows. Sample of 2.5 ml was applied to and allowed to penetrate a rinsed/drained pre-packed PD10 desalting fractionating column containing Sephadex G25 (GE Healthcare Sciences). The sample was then eluted to provide the void volume fraction material by addition of 3.5 ml of water with collection of the eluted sample fraction into a glass test tube. Subsequently the greater than void volume fraction was obtained by addition of a further 3.5 ml water and collection of this eluted fraction. These desalting columns are reported to separate materials of ≥10 kDa as in the void volume fraction from lower molecular weight materials as would elute in the second ≤10 kDa fraction. Thus, soluble polymer material in the first fraction would be separated from unreacted MAHMP and other reagents. A 0.1 ml subsample of the void volume fraction was diluted with 0.9 ml water and then 0.02 ml 0.18M $FeSO_4$/0.54M sodium citrate was added to react with any Fe-binding activity as contributed to the polymer material by MAHMP, i.e. as incorporated into the polymer. The average absorbance at 450 nm of two such samples of this sample was determined and this absorbance value was considered to represent the reference control (100%) for comparison to similarly prepared samples but as resulting from altered polymerization conditions. Synthesis conditions that were varied included temperature (50° C. versus control 40° C.) and the amounts of polymerization reagents ammonium persulphate and tetramethylethylenediamine. The results of these tests are shown in the graph of FIG. 19. These results indicated it was possible to increase the relative incorporation of MAHMP into the soluble polyvinylpyrrolidone polymer by increasing the polymerization temperature and especially by increasing the concentrations of the persulphate and tetramethylethylenediamine polymerization reactants.

Figure 20:
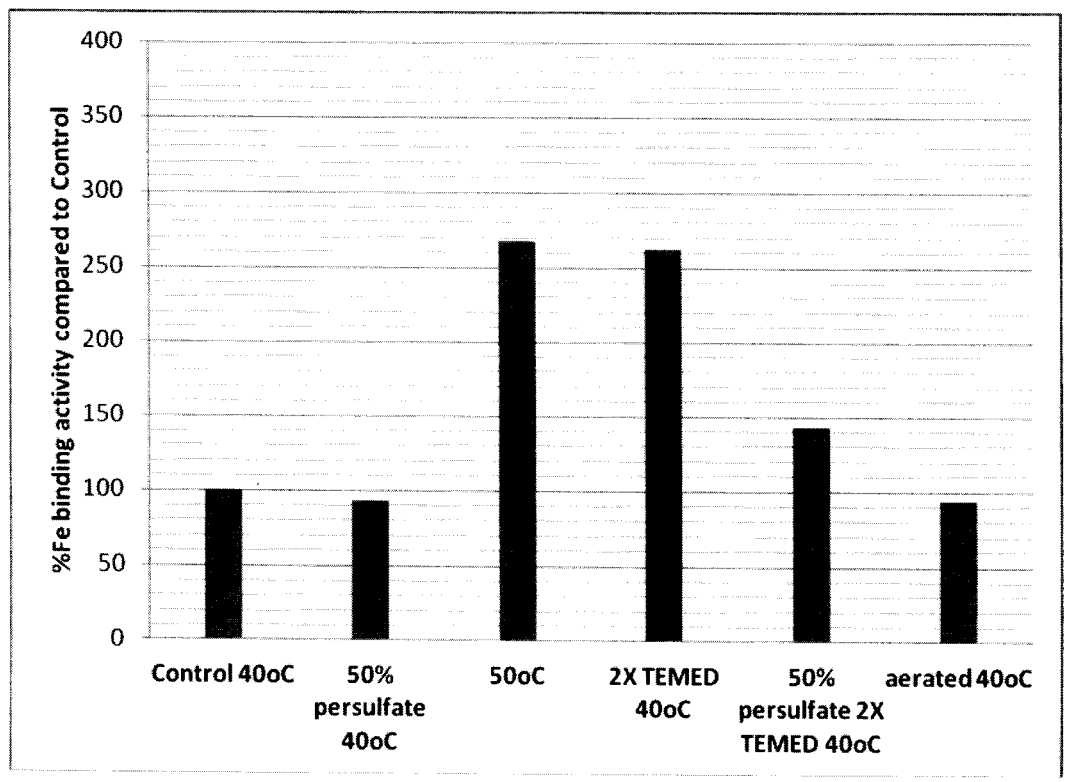
FIG. 20 is a graph of the data as obtained in Example 30.

Example 30; Synthesis Conditions Optimization for Soluble Chelating Compositions Comprising an Active Pyridinone Chelating Agent Co-Polymerized in a Soluble Linear Polyacrylamide Polymeric Carrier Chain A sample of soluble polymer was prepared as described in Example 6 and the raw polymerized fraction was separated as follows. Sample of 2.5 ml was applied to and allowed to penetrate a rinsed/drained pre-packed PD10 desalting fractionating column containing Sephadex G25 (GE Healthcare Sciences). The sample was then eluted to provide the void volume fraction material by addition of 3.5 ml of water with collection of the eluted sample fraction into a glass test tube. Subsequently the greater than void volume fraction was obtained by addition of a further 3.5 ml water and collection of this eluted fraction. These desalting columns are reported to separate materials of ≥10 kDa as in the void volume fraction from lower molecular weight materials as would elute in the second ≤10 kDa fraction. Thus, soluble polymer material in the first fraction would be separated from unreacted MAHMP and other reagents. A 0.1 ml subsample of the void volume fraction was diluted with 0.9 ml water and then 0.02 ml 0.18M $FeSO_4$/0.54M sodium citrate was added to react with any Fe-binding activity as contributed to the polymer material by MAHMP, i.e. as incorporated into the polymer. The average absorbance at 450 nm of two such samples of this sample was determined and this absorbance value was considered to represent the reference control (100%) for comparison to similarly prepared samples but as resulting from altered polymerization conditions. Synthesis conditions that were varied included temperature (50° C. versus control 40° C.) and the amounts of polymerization reagents ammonium persulphate and tetramethylethylenediamine, e.g. 50% of that used in the control or 2× that used in the control. Polymerization of this soluble polymer was much more rapid than was found for similar materials prepared with polyvinylpyrrolidone, i.e., such as those prepared as in Example 29. The aerated sample test included flushing with air versus the usual flushing with nitrogen gas as was done for the other test sample. The temperature of the reaction mixture at the start of polymerization was found to be more important such that initial temperatures in excess of 20° C. when polymerization reagents persulphate and TEMED were added often led to a gelling of the mixture or formation of very viscous polymer materials. This indicated a rapid polymerization to very high molecular weight polymers which, if of a high enough molecular weight, were no longer water soluble. An initial cooling of the reagent solution to at least 20° C. prior to TEMED addition, effective temperature control of the mixture during polymerization and slower addition of the TEMED, e.g. only 10% of the total TEMED added incrementally each 5 minute interval until all was added provided a more controlled polymerization of this soluble polymer. Results of varying the amounts of reagents and temperature during polymerization did affect the amounts of MAHMP incorporated into the polymer as based on Fe-binding activity of the materials in the void volume fraction of the PD10 separation and the results of these tests are shown in the graph of FIG. 20.

Figure 21:
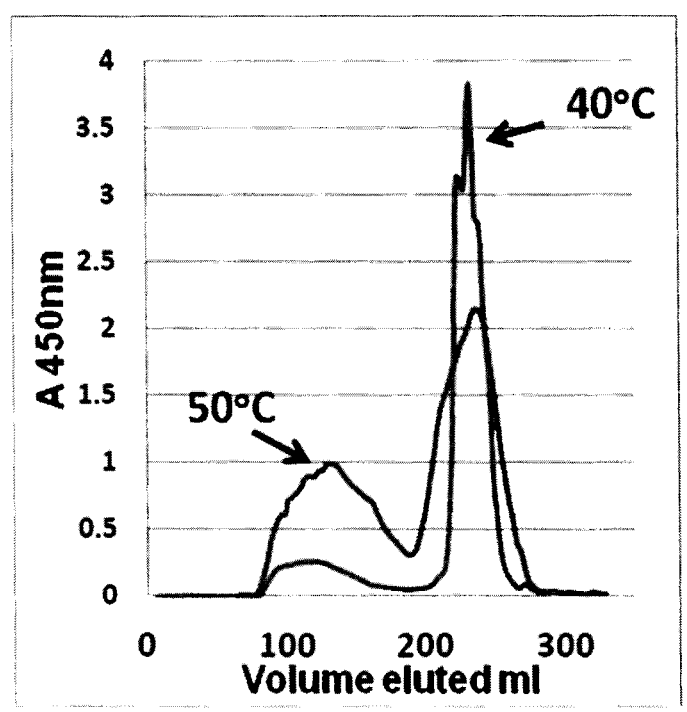
FIG. 21 is a graph of the data as obtained in Example 30.

The results graphed in FIG. 21 show the relative size distributions of the polymerized reaction mixtures without separation by dialysis or with PD10 desalting columns, i.e., samples of raw polymerization reaction mixtures after polymerization, were applied to a column of Sepharose CL-6B and eluted with water to provide various eluted fractions for analyses. These results illustrate the incorporation of increased amounts of MAHMP into higher molecular weight materials when polymerization was carried out at a higher temperature. The materials eluting at around 100 ml represent very high molecular weight polymer material of around 2 MDa near the upper size separation limit of the Sepharose (column void volume) while the materials eluting at around 200 ml or later represent much lower molecular weight materials. Unreacted MAHMP would elute last, i.e., in the highest elution volume.

Figure 22:
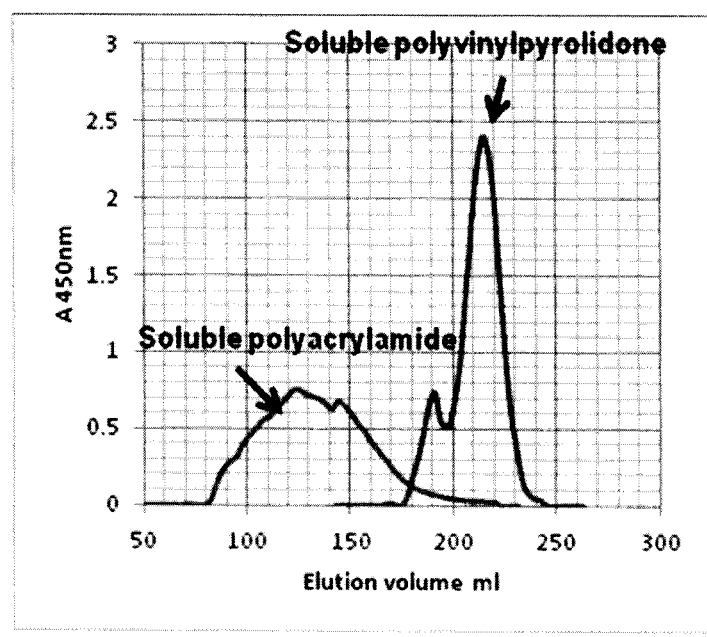
FIG. 22 is a graph of the data as obtained in Example 31.

Example 31; Comparison of Molecular Size (Weight) of Soluble Chelating Compositions Comprising an Active Pyridinone Chelating Agent Co-Polymerized in a Soluble Linear Polyvinylpyrolidone Polymeric Carrier Versus an Active Pyridinone Chelating Agent Co-Polymerized in a Soluble Linear Polyacrylamide Polymeric Carrier Chain Samples of the raw polymerization reaction mixtures as obtained from Example 29 and Example 30 were dialyzed using a dialysis tubing membrane with nominal exclusion limit of 8 kDa against water and the materials of >8 kDa as retained in the dialysis membrane were compared as to molecular size distributions or their soluble polymer materials. Samples were applied to a column of Sepharose CL-6B with elution by approximately 300 ml with water. Collected fractions of approximately 4.5 ml were treated with 0.01 ml 0.18 $MFeSO_4$/0.54M sodium citrate to detect presence of the MAHMP pyridinone chelating agent and their absorbances were measured at 450 nm. The results in FIG. 22 compare the size distributions of a soluble polymer composed of an active pyridinone chelating agent co-polymerized in a soluble linear polyvinylpyrolidone polymeric carrier prepared as in Example 29 where 2× the control amount of TEMED was utilized with polymerization at 40° C. to a soluble polymer composed of an active pyridinone chelating agent co-polymerized in a soluble linear polyacrylamide polymeric carrier chain prepared as in Example 30 where polymerization was carried out at 50° C.

These results show, together with the results in Examples 27 to Example 30, indicate that it is possible to adjust, i.e., by selection of the appropriate carrier material and by control of the polymerization conditions, the relative molecular size distribution of resultant soluble polymer chelating compositions, i.e., for example as made with polyvinylpyrolidone polymeric carrier chains or polyacrylamide polymeric carrier chains, so as to achieve a range of desired molecular sizes/weights. For example, systemic use of the soluble polymer materials in humans could benefit from the use of relatively low molecular sizes, example, below for example 30 kDa. i.e., so as to allow elimination form the body through removal in the kidneys and urinary tract, while topical application with humans, for example, in the eyes or other external sites, may benefit from the use of higher molecular weight materials which are not readily absorbed into the systemic aspects of the body.

Figure 23:
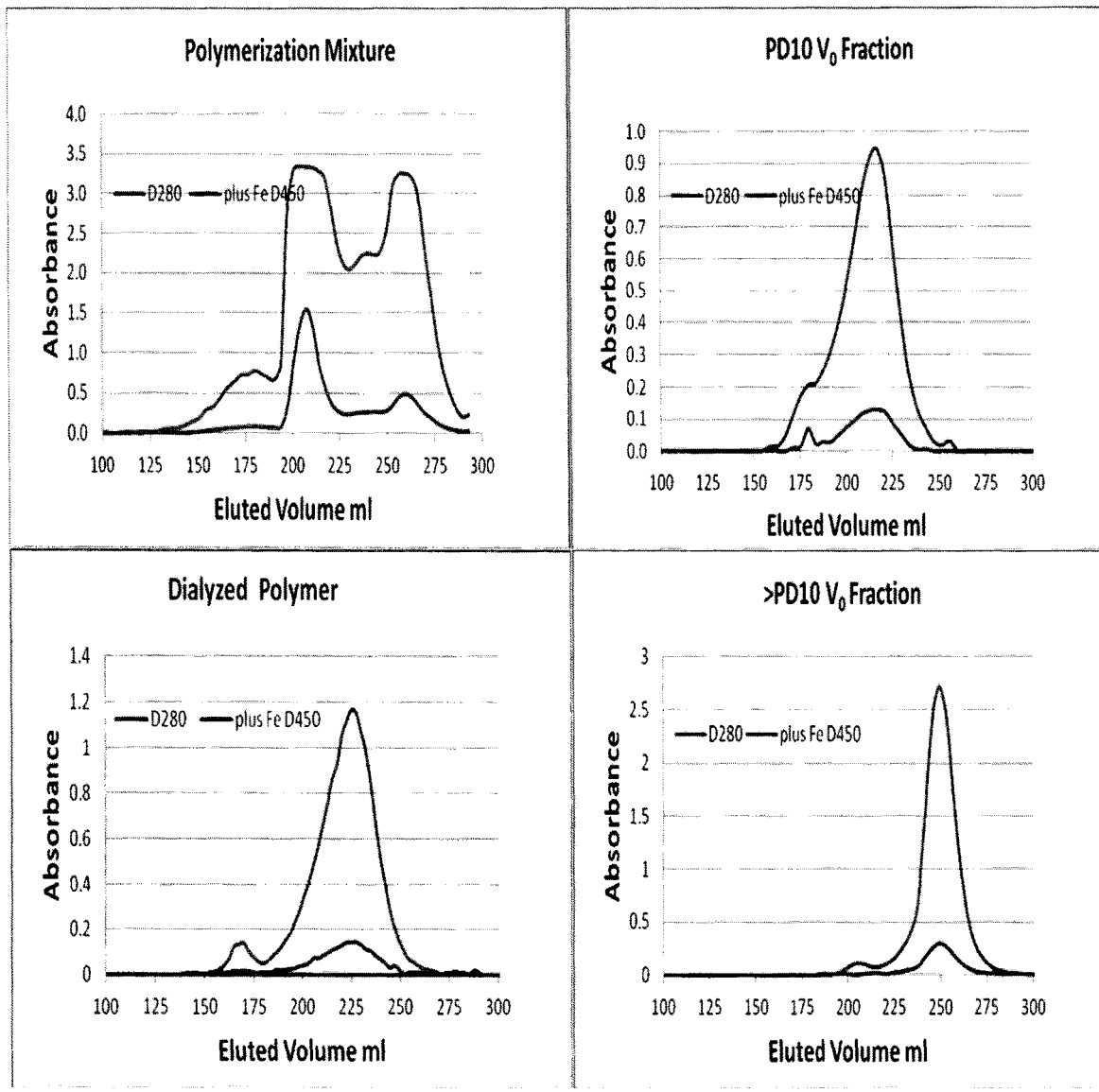
FIG. 23 is a series of graphs of the results as obtained in Example 32.

Example 32; Purification of Soluble Polymer Compositions by Size Exclusion Chromatographic Separation The raw polymerization reaction product mixture as prepared in Example 4 was treated to recover the desired higher molecular weight fraction as separate from the lower molecular weight fraction comprised of unreacted MAHMP and polymerization reagents as follows. A 2.5 ml sample of the polymerization mixture was applied to a drained column of Sephadex G-25 (PD10 separation column, GE Healthcare) and allowed to penetrate the column. A first fraction of eluted material (PD10 $V_o$) representing the higher molecular weight components was obtained by application or 3.5 ml of de-ionized water with collection of the eluted material into a single test tube. A second eluted fraction (>PD10 $V_o$) representing the lower molecular weight components was separately obtained by application of an additional 3.5 ml water with collection of the second fraction to a separate test tube. Samples of the two fractions were analyzed by application and elution with 300 ml water on a column of Sepharose Cl-6B to reveal the relative size distribution of their contained materials with eluted fractions being analyzed for both absorbances at 280 nm as untreated and at 450 nm, after addition of 0.01 ml 0.18M $FeSO_4$/0.54M sodium citrate. Samples of the raw polymerization mixture and the polymerization mixture after dialysis using a dialysis tube with a nominal exclusion limit of 8 kDa were also chromatographed and analyzed for comparison. The results for this purification are shown in FIG. 23. These results show that it is possible to separate the desired higher molecular weight soluble polymer chelator form the lower molecular weight residual reaction products by size exclusion separation chromatography using Sephadex G-25 and this separation produces similar separation and purification as to that obtained by a dialysis separation. Separation purification and recovery of the desired polymeric chelator by column separation on for example Sephadex G-25 has advantages in relation to scale up to obtain larger amounts of materials for use.

Figure 24:
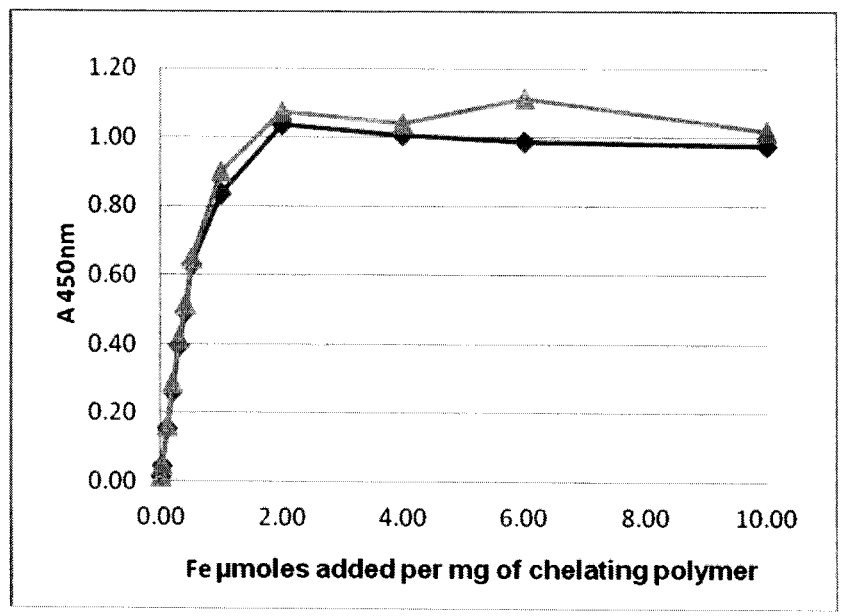
FIG. 24 is a graph of the results as obtained in Example 33.

Example 33; Iron Binding Capacity of Soluble Chelating Compositions Comprising an Active Pyridinone Chelating Agent Co-Polymerized in a Soluble Linear Polyvinylpyrolidone Polymeric Carrier Samples of 0.5 mg of soluble polymer as obtained by the method of Example 4 or by the method of Example 27 test 5, in water were placed in a series of separate test tubes to which were added varying amounts of $FeSO_4$ in 3× molar excess sodium citrate, all to a final similar volume with water. The tubes were mixed and the absorbance of each sample was measured at 450 nm. The results are shown graphically in FIG. 24 where absorbance versus amount of iron added is plotted for each polymer sample. Each tube in the test series of same chelating polymer contained the same quantity of composition with the same total potential iron binding capacity. Thus, the maximum absorbance value after which no increase in absorbance occurred with additional added iron indicated the amount of iron addition needed to saturate the iron binding capacity of the chelating composition. From these results the maximum Fe-binding capacities of both samples of the soluble chelator were similar and both approximately 2 μmoles Fe per mg of chelating polymer or approximately 10% (w/w). On the basis that both soluble chelating compositions had average molecular weights of approximately 12 kDa as was shown in FIG. 18, the specific binding capacity of the compositions was approximately 24,000 μmoles Fe per μmole of soluble composition.

This result allows a comparison to the iron binding defence protein lactoferrin where each mole of lactoferrin with a molecular weight of 80 kDa/mole binds only 2 atoms of Fe/mole. Thus the soluble chelating composition had a much larger Fe capacity, i.e., many orders of magnitude higher than lactoferrin.

Example 34; Soluble Chelating Composition Increases the Sensitivity of *Candida albicans* to the Anti-Fungal Agent Nystatin

*Candida albicans* ATCC 10231, yeast cells, as grown in defined medium with no additional added Fe as in example 18 and example 19, were tested in the same media for their sensitivities to nystatin, an antifungal agent as proto-typical of the class of polyene antibiotics that are commonly used to control fungal growth and pathogenesis in humans and with nystatin plus the soluble chelating composition, as prepared in example 4. Nystatin as typical of the polyene class of antifungal agents causes membrane damage as part of its mechanism of anti-fungal activity.

The standard NCCLS MIC procedure as utilized in example 15 was utilized and MIC concentrations providing 80% growth inhibition were determined after different lengths of contact (4 days, 10 days, and 21 days) with the agents. The results, shown in the table below, demonstrate that the yeast was much more susceptible to nystatin when in the presence of the soluble chelator, the soluble chelator provided a substantial improvement to the sensitivity of the yeast to the nystatin. It is important to note that only a low amount of the soluble chelating composition was added for these tests and this low amount of soluble chelator addition alone did not markedly affect growth of the yeast, i.e., when no nystatin was added. This example demonstrates the enhancement of the anti-cellular activity of a conventional anti-fungal antibiotic nystatin with one of the soluble chelating compositions as disclosed in this invention.

| Agent | Nystatin MIC μg/ml | | |
|---|---|---|---|
|  | 4 d | 10 d | 21 d |
| Nystatin alone | 0.23 | 3.8 | 7.5 |
| Nystatin plus 25 μg/ml soluble chelator | <0.12 | 0.12 | 0.47 |

These results show that the addition of even a small amount of a soluble chelating composition of the present invention increases the sensitivity of the yeast to the anti-cellular antibiotic agent nystatin.

Example 35; Soluble Chelating Composition Increases Cell Sensitivity to the Anti-Cellular Agent Fluorocytosine Fluorocytosine is a pyrimidine analogue drug that has anti-cellular activity against various eukaryotic cells including fungal and cancer cells. It is a pro-drug that is taken up and converted to an active form within eukaryotic cells where it interferes with nucleic acid synthesis and as such is representative a group of anti-cancer metabolite drugs. The ability of the soluble chelating compositions of the present invention to enhance its anti-cellular activity was tested using yeast cells as a typical representative eukaryotic test cell system.

*Candida albicans* ATCC 10231, yeast cells, as grown in defined medium with no additional added Fe as in example 18 and example 19, were tested in the same media for their sensitivities to 5-fluorocytosine, as a proto-typical example of the class of pyridine analogues that are commonly used to control fungal and cancer cell growth in humans and with fluorocytosine plus the soluble chelating composition, as prepared in example 4.

The standard NCCLS MIC procedure as utilized in example 15 was utilized and MIC concentrations providing 80% growth inhibition were determined after different lengths of contact (4 days, 10 days, and 21 days) with the agents. The results, shown in the table below, demonstrate that the yeast was much more susceptible to fluorocytosine when in the presence of the soluble chelator, the soluble chelator provided a substantial improvement to the sensitivity of the yeast to the fluorocytosine. It is important to note that only a low amount of the soluble chelating composition was added for these tests and this low amount of soluble chelator addition alone did not markedly affect growth of the yeast, i.e., when no fluorocytosine was added. This example demonstrates the enhancement of the anti-cellular activity of a conventional anti-cellular agent with one of the soluble chelating compositions as disclosed in this invention.

| Agent | Fluorocytosine MIC µg/ml | | |
|---|---|---|---|
| | 4 d | 10 d | 21 d |
| Fluorocytosine alone | 0.025 | 0.05 | 0.05 |
| Fluorocytosine plus 25 µg/ml soluble chelator | <0.003 | 0.012 | 0.012 |

Example 36; Demonstration of the Preservation of a Product Through Addition of a Soluble Chelating Composition as within a Semi-Permeable Device in Conjunction with Sorbate a Conventionally Used Preservation Agent

Figure 25:
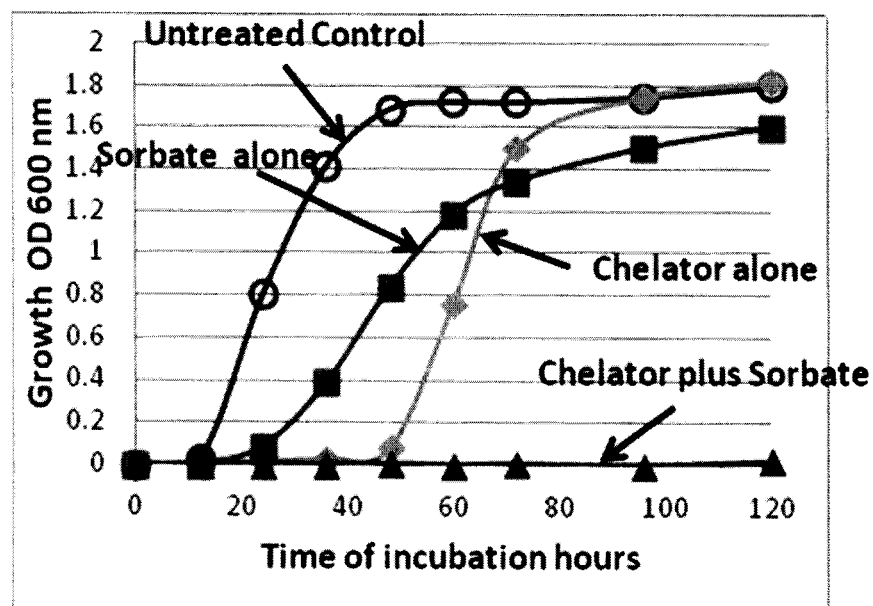
FIG. 25 is a graph of the results obtained in Example 36.

*Candida albicans* ATCC 10231, yeast cells, as grown in defined medium as for example 18 with no additional added iron (i.e., the only but adequate Fe available for the yeast was contributed from being present along with the other added medium components) was tested for its sensitivity to the preservative agent sorbate in a challenge growth test in shaken flask cultures using the same medium to which sorbate was added at 0.025 mg/ml. In one such culture, only medium was present as a control. In a second, sorbate was present in medium at 0.025 mg/ml and in a third culture, sorbate at 0.025 mg/ml was included along with 0.3 mg of a soluble chelating composition as prepared in example 4. The chelator was not added directly to the culture medium but was provided as within a dialysis membrane within the culture medium, such that only the external surfaces of the dialysis membrane device were in contact with the bulk of the culture medium, the chelator being within the membrane bag. The dialysis membrane was of the same type that had been used to prepare the soluble chelator and thus its use here ensured that the added chelator would be retained within the membrane device as in contact with the culture medium from within a semi-permeable membrane, i.e., the dialysis tubing. Thus the chelator would not be in direct physical contact with the yeast cells while any iron or sorbate or other low molecular weight media constituents or low molecular weight yeast cell products in the test milieu could diffuse in or out of the semi-permeable device. In a fourth test, 0.3 mg soluble chelator within a similar dialysis bag was added but sorbate was not added to the medium. All four test cultures were inoculated with the yeast and growth was monitored at intervals in the test cultures by optical density measurement at 600 nm over a 120 hr test period. The results of these tests are shown in the graphs in FIG. 25. These results show that the sorbate alone only delayed and slowed yeast growth while sorbate with the chelator in the semi-permeable device prevented growth completely. The chelator provided alone as within a semi-permeable device delayed growth substantially but in this test, growth eventually occurred with the chelator alone.

Example 37; Demonstration of Enhancing the Activity of an Antifungal Agent Fluconazole Through Addition of a Soluble Chelating Composition as within a Semi-Permeable Device

Figure 26:
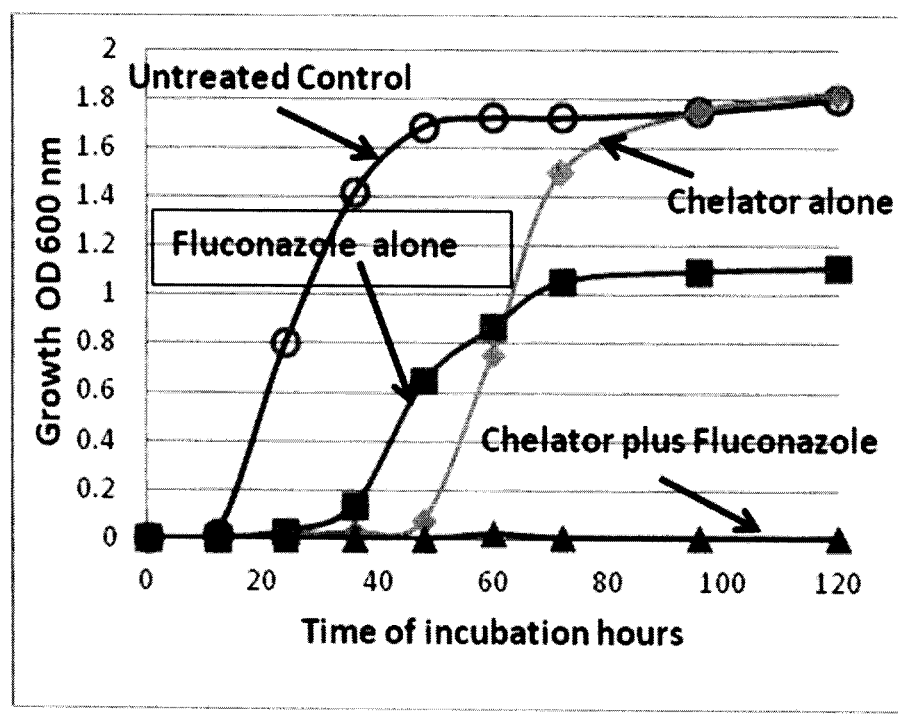
FIG. 26 is a graph of the results obtained in Example 37.

*Candida albicans* ATCC 10231, yeast cells, as grown in defined medium as for example 18 with no additional added iron (i.e., the only but adequate Fe available for the yeast was contributed from being present along with the other added medium components) was tested for its sensitivity to the anti-fungal antibiotic agent fluconazole in a challenge growth test in shaken flask cultures using the same medium to which fluconazole was added at 0.083 µg/ml. In one such culture, only medium was present as a control. In a second, fluconazole was present in medium at 0.083 µg/ml and in a third culture, fluconazole at 0.083 µg/ml was included along with 0.3 mg of a soluble chelating composition as prepared in example 4. The chelator was not added directly to the culture medium but was provided as within a dialysis membrane within the culture medium, such that only the external surfaces of the dialysis membrane device were in contact with the bulk of the culture medium, the chelator being within the membrane bag. The dialysis membrane was of the same type that had been used to prepare the soluble chelator and thus its use here ensured that the added chelator would be retained within the membrane device as in contact with the culture medium from within a semi-permeable membrane, i.e., the dialysis tubing. Thus the chelator would not be in direct physical contact with the yeast cells while any iron or sorbate or other low molecular weight growth medium constituents or low molecular weight yeast cell metabolic products in the test milieu could diffuse into or out of the semi-permeable device. In a fourth test, 0.3 mg soluble chelator within a similar dialysis bag was added but fluconazole was not added to the medium. All four test cultures were inoculated with the yeast and growth was monitored at intervals in the test cultures by optical density measurement at 600 nm over a 120 hr test period. The results of these tests are shown in the graphs in FIG. 26. These results show that the fluconazole alone only delayed and partially restricted yeast growth while fluconazole along with the chelator in the semi-permeable device prevented growth completely. The chelator provided alone as within a semi-permeable device delayed growth substantially but in this test, growth eventually occurred with the chelator alone.

Example 38; Demonstration of the Ability to Restrict Microbial Growth by Iron Removal and Establishment of Dose Dependence of Iron Supply for Microbial Growth Iron was selectivity removed from RPMI-1640 culture medium (Sigma Chemical Company) a chemically defined cell nutrient culture medium. This medium was contacted with 2 g/litre of the liquid medium with insoluble chelating, prepared as in example 5, during shaking at room temperature for 4 hours, followed by filtration to separate the insoluble chelating composition from the treated medium. This procedure provided a basal medium with partially removed Fe, i.e., to a very low residual concentration. The extracted medium was filter-sterilized for use as a basal culture medium and to which known amounts of Fe were re-added. Iron was added as a concentrated solution to achieve the desired final co0ncnetration in the medium and the iron solution made from $FeSO_4$ with a 3M excess of sodium citrate in the solution to ensure all the iron was present as a Fe-citrate complex, ensuring its stability and solubility. The treated medium was measured for its content of iron and other biologically important metals and elements by high resolution plasma emission spectrophotometry as compared to analyses for untreated medium. The data in the table below demonstrate the relatively high specificity for Fe removal from this medium. Major ions and metals needed for microbe cellular nutrition such as Mg, Ca, P etc were not removed by the insoluble chelating composition treatment. Some trace metals that are more closely chemically related to iron but important for cell nutrition to lesser extents than iron, were also partially removed by the insoluble chelating composition and these included Mn, Co and Mo. The increased concentrations seen for certain elements such as Ni and Ba as a result of the treatment are likely due to contaminant element introduction during the treatment steps. Such contaminant introduction would be avoidable through more extensive pre-cleaning washing of the insoluble composition and the filtering materials etc.

| Element | Untreated RPMI (n = 2) | Treated RPMI (n = 6) |
| --- | --- | --- |
| Na (mg/l) | 4508 | 4524 |
| Mg (mg/l) | 9 | 8.8 |
| Al (µg/l) | 12.9 | 2.7 |
| P (mg/l) | 189 | 188 |
| S (mg/l) | 5769 | 5787 |
| K (mg/l) | 212 | 209 |
| Ca (mg/l) | 18.4 | 17.4 |
| Mn (µg/l) | 0.28 | 0.04 |
| Fe (µg/l) | 6.3 | 0.79 |
| Co (µg/l) | 0.13 | 0.03 |
| Ni (µg/l) | 1.28 | 5.07 |
| Cu (µg/l) | 0.75 | 0.58 |
| Zn (µg/l) | 12.75 | 32.7 |
| Mo (µg/l) | 2.74 | 0.17 |
| Sn (µg/l) | 0.35 | 0.78 |
| Ba (µg/l) | 23.2 | 96.5 |

Figure 27:
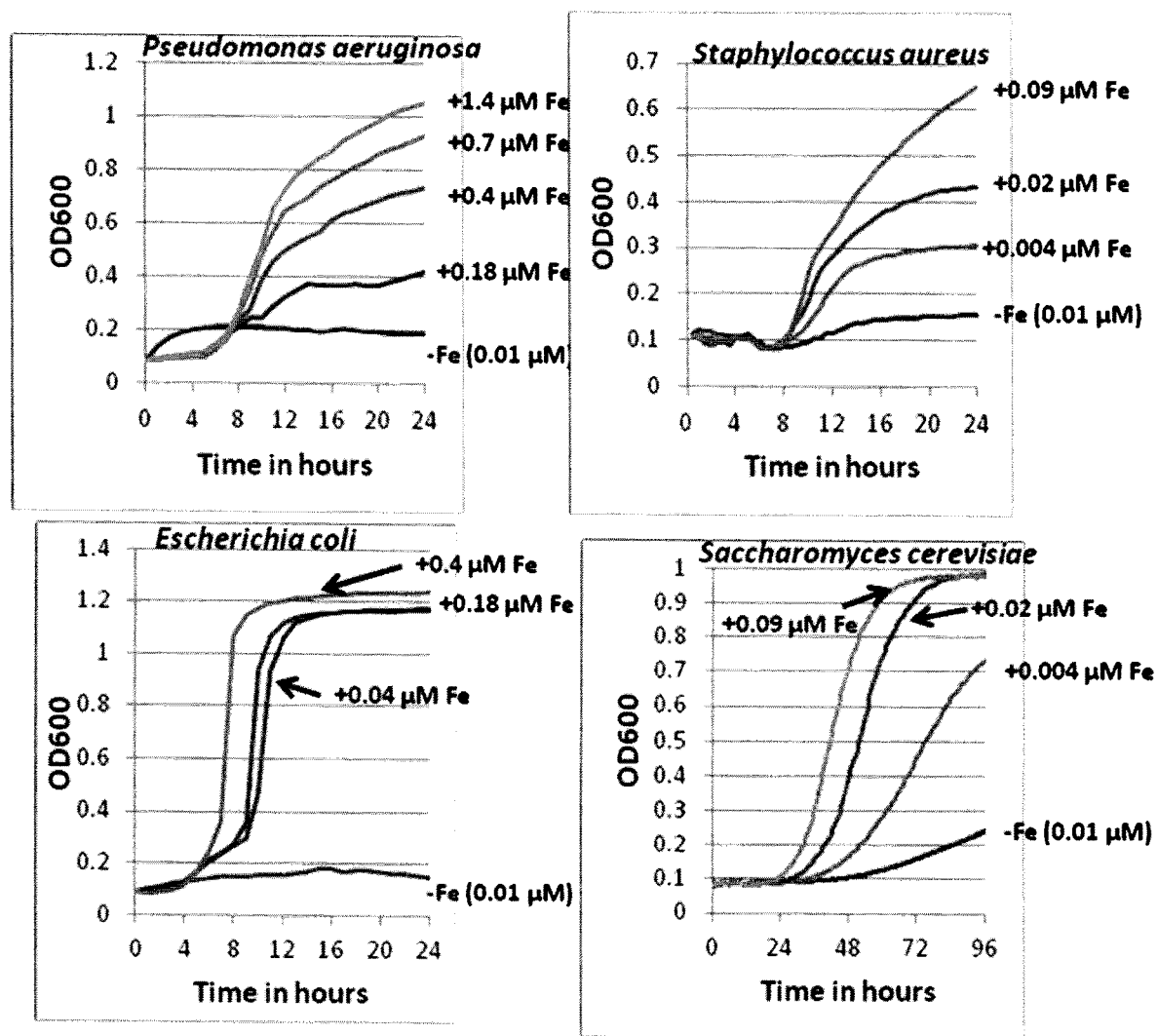
FIG. 27 is a graph of the results obtained in Example 38.

Representative bacteria (both Gram positive and Gram negative types) and fungi (yeast), selected to add to those tested as in example 13 through to example 19 were tested for growth in the basal medium and the basal medium with added iron. Test microorganisms included *Pseudomonas aeruginosa* strain PA01, *Escherichia coli* ATCC #25922, *Staphylococcus aureus* ATCC #29213 and *Saccharomyces cerevisiae* DL1. Results shown in the graphs of FIG. 27 demonstrate a greatly reduced or lack of growth for these test microorganisms in the RPMI medium with reduced iron content (residual Fe concentration of approximately 0.01 µM Fe). The three bacterial species were unable to grow to any significant extent in the treated medium with a Fe concentration of just 0.01 µM but capacity for growth was restored to the medium in a dose-dependent manner with Fe addition. Of the three bacterial strains tested, *Pseudomonas aeruginosa* appeared to have the higher Fe requirement with full growth restored by addition of 1.4 µM (even higher amounts (not shown in the graph) gave similar results). *Staphylococcus aureus* appeared to have the smallest Fe requirement with just 0.09 µM providing full growth. The yeast *Saccharomyces cerevisiae* grew slightly in the extracted RPMI and full growth capacity was restored by addition of 0.09 µM Fe.

Example 39; Affects of Soluble Chelating Compositions of the Present Invention and Conventional Small Molecule Chelators on the Growth of Microorganisms Soluble chelating compositions prepared as in example 4 and example 6 as well as the commercially clinically used low molecular weight (<1500 Da) chelators desferal (Novartis Pharmaceutical Company) and deferiprone (Apotex Pharmaceutical Company) were tested as to their MICs against representative pathogenic bacterial species in RPMI medium that had been treated as in example 38 but to which Fe was re-added to known concentrations that permitted growth of the bacteria under partially Fe restrictive conditions, i.e., so as to simulate the low Fe environmental supply available during infection by these bacteria in man or other animals. MIC testing was done in a manner similar to that described for example 15 but with test series being conducted in multi-well microtiter plates, each well providing a separate treatment test.

The results in the table below show that the soluble chelators of the present invention were inhibitory to all three bacterial pathogens at both Fe levels tested with the slight increased MIC values at the higher Fe concentration tested indicating the inhibition was related to Fe amounts in the test. For MIC values in the table shown as ≤, these showed complete inhibition at the lowest concentration tested. For MIC values in the table shown as >, these showed no inhibition at the highest concentration tested. The clinically used chelators were not inhibitory in the case of *Pseudomonas aeruginosa* with no inhibition observed at the highest concentration tested (300 µg/ml for desferal and 100 µg/ml for deferiprone). *Staphylococcus aureus* was not inhibited by desferal and was inhibited by deferiprone to a lesser extent than for the soluble compositions of the present invention. Conversely, *Escherichia coli* was not inhibited by deferiprone but was inhibited substantially by desferal. These results illustrate the generalized inhibition of growth obtainable in low Fe environments such as those that exist in the host during infection by the chelating compositions of the present invention which tightly sequester Fe in the external environment of cells and are not taken up or are not surface accessible for their Fe by the cells being targeted. This result is in direct contrast to the lack of uniform susceptibility and the variable sensitivity observed for low molecular weight (<1500 Da) chelators that can be taken up into the cells being targeted or are accessible for their Fe at the surface of the cells being targeted, owing to the low molecular weights of these conventional chelators and/or the lower efficiency of such low molecular weight chelators for sequestering Fe.

|  | MIC µg/ml | | | |
|---|---|---|---|---|
| BACTERIUM/FE µM | SOLUBLE COMPOSITION EXAMPLE 4 | SOLUBLE COMPOSITION EXAMPLE 6 | DESFERAL | DEFERIPRONE |
| E. coli/0.02 µM | 0.59 | 2.34 | 0.009 | >100 |
| E. coli/0.09 µM | 2.34 | 9.4 | 0.59 | >100 |
| P. aeruginosa/0.02 µM | ≤0.59 | ≤0.59 | >300 | >100 |
| P. aeruginosa/0.09 µM | ≤0.59 | 4.69 | >300 | >100 |
| S. aureus/0.02 µM | 0.08 | 0.15 | >300 | 12.5 |
| S. aureus/0.09 µM | 0.15 | 0.59 | >300 | 25 |

Example 40; Demonstration that Nutritional Iron Supply Affects Sensitivity of Pathogenic Microbes to Conventionally Utilized Antibiotics Representative pathogenic bacteria (both Gram positive and Gram negative types) were tested for their sensitivities to conventionally utilized antibiotic agents both in normal RPMI medium with its typical 0.11 µM Fe content and in RPMI medium that had been treated with one of the insoluble chelating compositions of the present invention as in example 38 and to which Fe was then re-added to provide a relatively low known Fe addition as typical in the iron restricted environment during infection of man or other animals. Test microorganisms included *Pseudomonas aeruginosa* strain PA01, *Escherichia coli* ATCC #25922 and *Staphylococcus aureus* ATCC #29213. The results shown in the table below demonstrate that the each of the bacteria displayed an increased sensitivity (lower MIC) for at least some of the antibiotics tested in medium of lower Fe content versus the higher Fe content in untreated RPMI medium. For MIC values in the table shown as ≤, these showed complete inhibition at the lowest concentration tested. For MIC values in the table shown as >, these showed no inhibition at the highest concentration tested. The strain of *Pseudomonas aeruginosa* tested was resistant to most of the antibiotics tested. *Staphylococcus aureus* and *Escherichia coli* both displayed increased susceptibilities to several of the antibiotics tested. These results show more generally that anti-cellular antibiotics of various chemical classes can be improved as to their activity against various pathogenic bacteria through making iron less available to the pathogenic bacterium being targeted by the anti-cellular agent.

Example 41; Affects of Soluble Chelating Compositions of the Present Invention on the Production of Flavin, an Example of Influencing Secondary Metabolite Production Activity by *Candida albicans*

Figure 28:
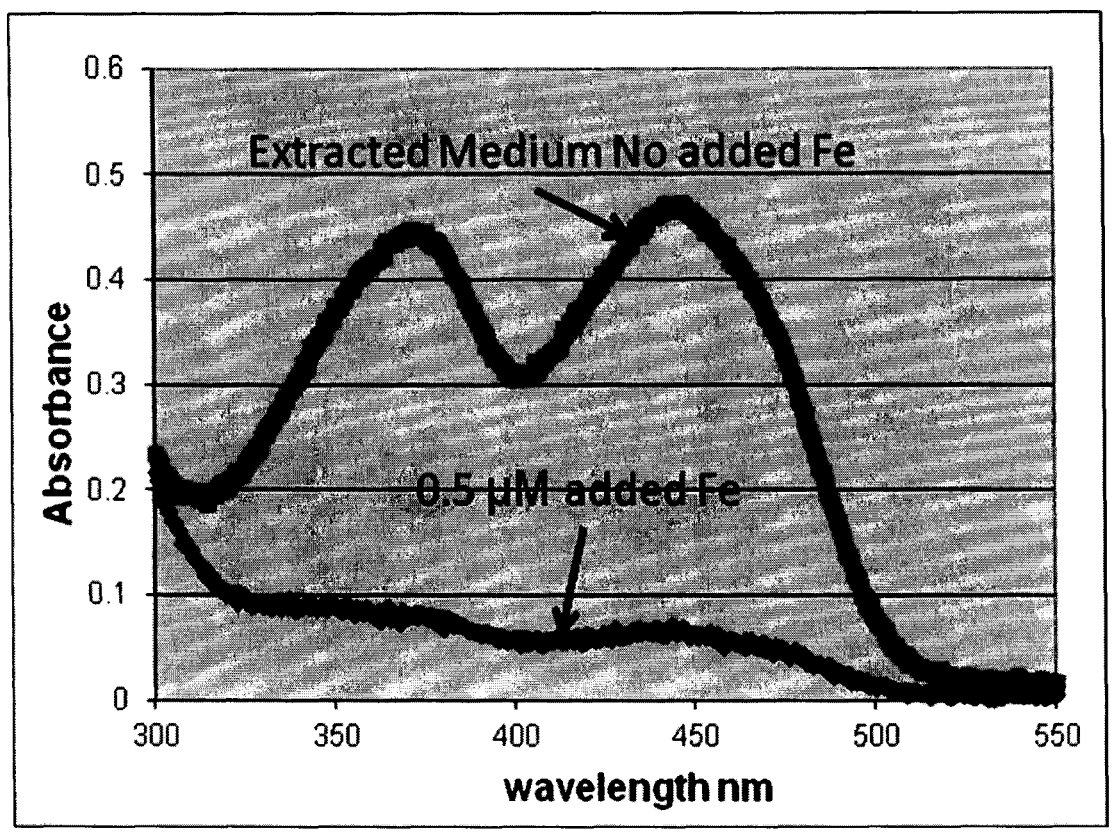
FIG. 28 is a graph of the results obtained in Example 41.
Figure 29:
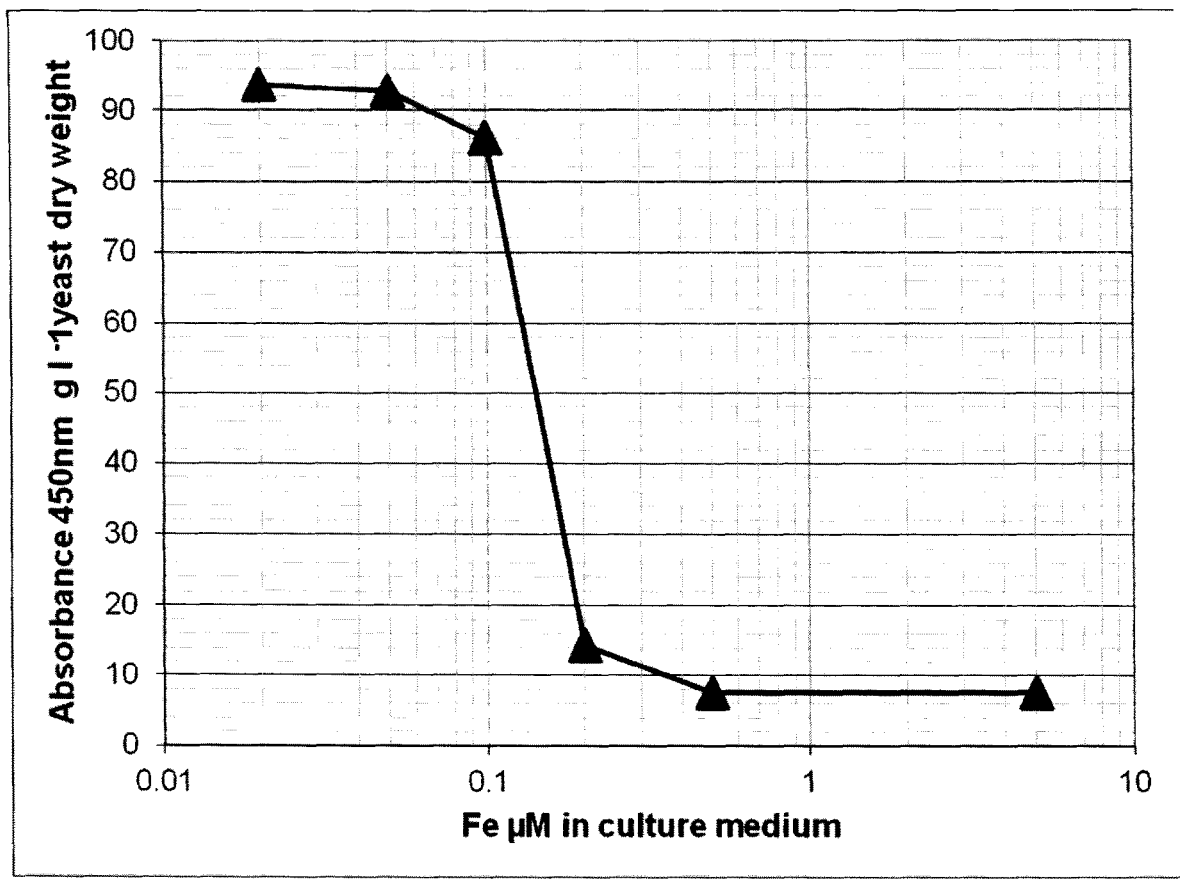
FIG. 29 is a graph of the results obtained in Example 41.

*Candida albicans* ATCC 10231 yeast cells, as grown in defined extracted medium as for example 18 as well as with this extracted medium to which known additions of supplemental iron were added (as a solution of $FeSO_4$/3M excess sodium citrate), were tested for production of flavin compounds. Flavin production as evidenced by a yellow pigmentation in the culture medium with an absorption spectrum as shown in FIG. 28 (absorption peaks at approximately 375 nm and 450 nm from produced flavins as secreted into the culture medium) was evident at low but not at higher iron concentrations during growth. Flavin production was expressed as absorption units at 450 nm per g of oven dried cell biomass at each amount of added iron with results of these tests as shown in FIG. 29. These results show that flavin production was higher when low amounts of iron were supplied to the yeast cells and with higher iron amounts of iron present, flavin production by the yeast was minimal.

Cultures prepared under conditions where flavin production would be suppressed due to the relatively high amounts of available iron were then tested for flavin production after addition of soluble chelators of the present invention as prepared in example 4 or example 6, i.e., as compared to controls where no chelator was added to the cultures. Addition of either of these soluble chelators at for example, concentrations of 0.25 mg/ml to such cultures containing otherwise flavin-repressing iron levels, enhanced flavin pro-

|  | MIC µg/ml | | | | | |
|---|---|---|---|---|---|---|
|  | *Escherichia coli* | | *Pseudomonas aeruginosa* | | *Staphylococcus aureus* | |
| Antibiotic | Untreated RPMI 0.11 µM Fe | Treated RPMI + 0.009 µM Fe | Untreated RPMI 0.11 µM Fe | Treated RPMI + 0.09 µM Fe | Untreated RPMI 0.11 µM Fe | Treated RPMI + 0.004 µM Fe |
| Ampicillin | 4 | 4 | >512 | >512 | 1 | 0.25 |
| Ciprofloxacin | 0.0078 | 0.008 | 4 | 1 | 0.5 | 0.25 |
| Clarithromycin | >512 | 16 | >512 | >512 | 1 | 0.125 |
| Clindamycin | 256 | 128 | >512 | >512 | 0.125 | 0.0156 |
| Fusidic acid | >512 | >512 | >512 | >512 | 0.25 | 0.0625 |
| Mupirocin | 128 | 64 | >512 | >512 | 0.0625 | 0.0156 |
| Neomycin | 2 | 2 | 32 | 16 | 1 | 1 |
| Tetracycline | 4 | 2 | 32 | 32 | 0.5 | 0.125 | duction by this yeast as observed by increased production of cell product materials in the culture medium that absorbed at 450 nm. Thus, the soluble chelators sequestered iron in the culture medium making it non-accessible by the yeast cells and therefore induced the production of flavins by the yeast cells.

Example 42; Synthesis of Soluble Chelating Compositions Comprising Mimosine Affixed to Hydroxyethyl Starch or Dextran Soluble hydroxyethyl starch or soluble dextran samples prepared as in example 2 were reacted with a 0.075 M solution of mimosine (β-(N-(3-Hydroxy-4-pyridone))-α-Aminopropionic Acid) at neutral to slightly alkaline pH. The Schiff bases formed between the amino groups of the mimosine and the aldehyde groups on the polymers were then reduced with excess sodium cyanoborohydride so as to stabilize the linkage, while any remaining un-reacted aldehyde groups on the starch or dextran were reduced with the excess sodium borohydride. The soluble chelating polymer composition product was purified by dialysis in a Visking dialysis bag against water over 48 hours with 5 changes of the dialysis water. The molecular weight cut-off size for the dialysis tubing used was approximately 10,000 Daltons and thus the final soluble chelating composition products retained in the dialysis bags had a molecular weight of ≥10,000 Daltons. The iron-binding ability of the resultant soluble chelating compositions was confirmed by addition of excess iron-citrate solution to a test portion of the chelating composition. The tested portion turned red indicating binding of iron to the chelator pyridinone groups as contributed by the mimosine bound to the carrier polymers. It should be appreciated that no steps other than to dialyze away materials of a size less than 10,000 Daltons were taken with these sample preparations. It should be noted that further steps to provide more refined, i.e. lower molecular weight (e.g. greater than 1500 Daltons) product or smaller product size distributions could be taken using conventional known methods such as ultrafiltration and/or chromatographic purification, i.e., in relation to obtaining a more refined product of a given molecular weight distribution. The final chelating compositions were obtained by lyophilization so as to remove the suspending water and the dry products were found to be freely soluble in water for use.

The entire contents of the references mentioned throughout this disclosure are incorporated herein by reference including U.S. Pat. Nos. 4,530,963; 5,256,676; 5,302,598; 5,573,800; 5,837,677; 5,663,201; 5,656,591; 6,165,484; 6,267,979; 6,767,741; 6,793,914; 6,825,204; 6,893,630; 6,932,960; 7,410,985; and 7,446,089.

The present invention has been described with regard to a plurality of illustrative embodiments. However, it will be apparent to persons skilled in the art that a number of variations and modifications can be made without departing from the scope of the invention as defined in the claims.

REFERENCES

The following references are also incorporated herein by reference:

Buss, J. L., F. M. Torti, S. V. Torti. 2003. The role of iron chelation in cancer therapy. Cur. Medicinal Chem. 10: 1021-1034

De Domenico. I, T. Y. Zhang, et al. 2010. Hepcidin mediates transcriptional changes that modulate acute cytokine-induced inflammatory responses in mice. J. Clin. Invest. 120: 2395-2405.

Dumitru, R., J. M. Hornby, and K. W. Nickerson. 2004. Defined anaerobic growth medium for studying Candida albicans basic biology and resistance to eight antifungal drugs. Antimicrob. Agents Chemother. 48:2350-2354

Feng, M., L van der Does and A. Bantjes. Iron (III)-chelating resins.3. Synthesis, Iron (III)-chelating properties and in vitro antibacterial activity of compounds containing 3-hydroxyxy-2-methyl-4(1H)-pyridinone ligands. J Med. Chem. 36: 2822-2827.

Feng, M, 1996. Synthesis and properties of a temperature-sensitive chelating hydrogel and its metal complexes; Polymers for Advanced Technologies Volume 7, pp. 613-618.

Grenier, D., M.-P. Huot, D. Mayrand. 2000. Iron-Chelating Activity of Tetracyclines and Its Impact on the Susceptibility of Actinobacillus actinomycetemcomitans to These Antibiotics. Antimicrob. Agents Chemotherapy 44:763-766.

Hentzer M., M. Givskov. 2003. Pharmacological inhibition of quorum sensing for the treatment of chronic bacterial infections. J. Clin. Invest. 112:1300-1307

Howard, D. H. 1999. Acquisition, Transport, and Storage of Iron by Pathogenic Fungi Clin. Microbiol. Rev. 12:394-404.

Huber, A., L., Holbein, B., E., and Kidby, D., K. 1990. Chapter 2.6, in Biosorption of Heavy Metals, B Volesky, editor, CRC Press, Boca Raton, USA Hsu, P-C, C-Y Yang, C-Y Lan. 2011. Candida albicans Hap43 is a repressor induced under low-iron conditions and is essential for iron-responsive transcriptional regulation and virulence. Eukaryotic. Cell. 10: 207-225.

Hughes, Poole. 1989, Metals in Microorganisms, Chapman and Hall, London, p 42-43.

Lalonde R. G., B. E. Holbein. 1984. Role of Iron in Trypanosoma cruzi Infection of Mice. J. Clin. Invest. 73: 470-476.

Martinez, J. L., F. Baquero. 2002. Interactions among Strategies Associated with Bacterial Infection: Pathogenicity, Epidemicity, and Antibiotic Resistance. Clin. Microbiol. Rev. 15: 647-679.

Porterfield, J., S. 1978. Section G: diets, culture media, food supplements; page 139, in Recheigl, M. CRC handbook series in nutrition and food. CRC Press, Boca Raton, USA Prasad, R. and K. Kapoor. 2005. Multidrug resistance in yeast Candida. Int. Rev. Cytol. 242:215-248.

Pradines B., C. Rogier, T. Fusai, J. Mosnier, W. Daries, E. Barret, D. Parzy. 2001. In vitro activities of antibiotics against Plasmodium falciparum are inhibited by iron Antimicrob. Agents Chemotherapy. 45: 1746-1750

Singh P. K., M. R. Parsek, E. P. Greenberg, M. J. Welsh. 2002. A component of innate immunity prevents bacterial biofilm development. Nature 417: 552-555.

Stintzi, A., C. Barnes, J. Xu, K. N. Raymond. 2000. Microbial iron transport via a siderophore shuttle: a membrane ion transport paradigm. PNAS 97: 10691-10696.

We claim:

1. A chelating composition soluble in an aqueous medium for chelating iron, said chelating composition comprising:
   a carrier material; and
   one or more suitable metal binding chemical groups having iron chelating activity affixed to or incorporated into the structure of the carrier material;
   wherein the one or more suitable metal binding chemical groups is one or more of carboxyl, hydroxyl, phenol ate, catechol ate, hydroxamate or hydroxypyridinone types;

wherein the carrier material comprises vinylpyrrolidone, styrene or acrylamide;

wherein the chelating composition is formed by a first monomer group comprising a metal binding monomer representing the metal binding chemical group copolymerized with a suitable second monomer group representing the carrier material such that the resulting co-polymer remains soluble in aqueous solution and has iron chelating activity;

wherein the chelating composition has a minimum molecular weight sufficiently large so as not to be normally taken up into the intra-cellular aspects internal to a cell membrane of a living cell and is able to bind iron; and wherein the chelating composition remains substantially soluble in the aqueous medium with its bound iron in the external cellular environment of the living cell thereby preventing uptake of the bound iron into the intra-cellular aspects internal to the cell membrane of the living cell.

2. The chelating composition of claim 1, wherein the living cell is affected in its growth or activities by having insufficient amounts of the iron available for its use.

3. The chelating composition of claim 1, wherein the chelating composition comprises metal binding chemical groups of 3-hydroxy-pyridin-4-one incorporated into the carrier material comprised of vinylpyrrolidone or acrylamide.

4. The chelating composition of claim 1, wherein said chelating composition has a molecular weight range defined by a lower molecular weight limit, as measured prior to the binding of a metal or metals, of about 1500 Daltons so as not to be normally taken up into the intra-cellular aspects internal to a cell membrane of a living cell, and a higher molecular weight limit sufficiently low so as to allow the composition to remain soluble in an aqueous medium.

5. The chelating composition of claim 1, wherein the metal binding monomer is 3-hydroxy-1-(β-methacrylamidoethyl)-2-methyl-4(1H)-pyridinone, the second monomer is 1-vinyl-2-pyrrolidone or N,N-dimethyl-acrylamide and the final chelating composition is a soluble co-polymer soluble in an aqueous medium.

6. The chelating composition of claim 1, wherein the chelating composition is an iodine-containing chelating composition wherein the carrier material is comprised of vinylpyrrolidone bound with iodine, and wherein the iodine-containing chelating composition has anti-microbial properties contributed by the iodine in addition to the metal chelating aspect of the metal chelating composition.

7. The chelating composition of claim 1, wherein the metal chelating composition is for use in treating a disease in an animal, including a fish or a human, that has a disease attributable to a cell or cells, or the activity of a cell or cells, wherein the cell or cells causing the disease are one or more of a microbial cell(s), a cancer cell(s), or a uni-cellular or multi-cellular parasitic organism(s).

8. The chelating composition of claim 1, wherein the metal chelating composition is for administration alone or in conjunction with another anti-cellular agent comprising one or more of an antimicrobial agent, an anti-metabolite agent, an anti-viral agent, an anti-parasitic agent or an anti-cancer agent for use in treating a disease in an animal, including a fish or a human, that has a disease attributable to a cell or cells, or the activity of a cell or cells, wherein the cell or cells causing the disease are one or more of a microbial cell(s), a cancer cell(s), or a uni-cellular or multi-cellular parasitic organism(s).

9. The chelating composition of claim 7, wherein said cell or cells causing the disease are those of the animal itself.

10. The chelating composition of claim 1, wherein the metal chelating composition is for use for affecting the cell or cell activities of one or more spoilage microorganisms in an aqueous based health care or consumer product wherein the metal chelating composition is used to treat the product alone or in conjunction with a chemical preservative agent such that the treatment reduces the extent of microbial growth and/or spoilage in the aqueous based product.

11. The chelating composition of claim 2, wherein the cell or its activity affected by the cell having insufficient uptake of the iron is a cell resistant to the activity of another anti-cellular agent, or an activity which is the ability to grow as a biofilm on inanimate or living tissue surfaces.

12. A pharmaceutical composition comprising the chelating composition of claim 1 and a pharmaceutically acceptable carrier, excipient or diluent.

13. The chelating composition of claim 2 for use as an excipient in a pharmaceutical composition with an anti-cellular agent comprising one or more of an antimicrobial agent, an anti-metabolite agent, an anti-viral agent, an anti-parasitic agent or an anti-cancer agent.

14. The chelating composition of claim 1, wherein the metal chelating composition is for administration alone or in conjunction with another anti-cellular agent comprising one or more of an antimicrobial agent, an anti-metabolite agent, an anti-viral agent, an anti-parasitic agent or an anti-cancer agent for use in treating a disease in an animal, including a fish or a human, that has a disease attributable to a cell or cells, or the activity of a cell or cells, wherein the cell or cells causing the disease are one or more of a microbial cell(s), a cancer cell(s), or a uni-cellular or multi-cellular parasitic organism(s).

15. The chelating composition of claim 1 for use as an excipient in a pharmaceutical composition with an anti-cellular agent comprising one or more of an antimicrobial agent, an anti-metabolite agent, an anti-viral agent, an anti-parasitic agent or an anti-cancer agent.

16. The chelating composition of claim 2, wherein the metal chelating composition is for use for affecting the cell or cell activities of one or more spoilage microorganisms in an aqueous based health care or consumer product wherein the metal chelating composition is used to treat the product alone or in conjunction with a chemical preservative agent such that the treatment reduces the extent of microbial growth and/or spoilage in the aqueous based product.

17. A pharmaceutical composition comprising (a) one or more of an antimicrobial agent, an anti-metabolite agent, an anti-viral agent, an anti-parasitic agent or an anti-cancer agent, and (b) the chelating composition of claim 1.

* * * * *

UNITED STATES PATENT AND TRADEMARK OFFICE
CERTIFICATE OF CORRECTION

| | | |
|---|---|---|
| PATENT NO. | : 10,709,784 B2 | Page 1 of 1 |
| APPLICATION NO. | : 14/124619 | |
| DATED | : July 14, 2020 | |
| INVENTOR(S) | : Holbein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 931 days.

Signed and Sealed this
Seventh Day of February, 2023

Katherine Kelly Vidal
*Director of the United States Patent and Trademark Office*